(12) United States Patent
Chigaev et al.

(10) Patent No.: US 9,314,460 B1
(45) Date of Patent: Apr. 19, 2016

(54) METHOD FOR CANCER CELL REPROGRAMMING

(71) Applicants: Alexandre Chigaev, Santa Fe, NM (US); Larry A. Sklar, Albuquerque, NM (US); Dominique Perez, Albuquerque, NM (US)

(72) Inventors: Alexandre Chigaev, Santa Fe, NM (US); Larry A. Sklar, Albuquerque, NM (US); Dominique Perez, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 14/249,150

(22) Filed: Apr. 9, 2014

Related U.S. Application Data

(60) Provisional application No. 61/810,060, filed on Apr. 9, 2013.

(51) Int. Cl.
| | |
|---|---|
| C07D 309/00 | (2006.01) |
| A61K 31/47 | (2006.01) |
| A61K 31/122 | (2006.01) |
| G01N 33/50 | (2006.01) |
| A61K 31/4425 | (2006.01) |
| A61K 31/357 | (2006.01) |
| A61K 31/343 | (2006.01) |
| A61K 31/35 | (2006.01) |
| A61K 31/437 | (2006.01) |

(52) U.S. Cl.
CPC .............. *A61K 31/47* (2013.01); *A61K 31/122* (2013.01); *A61K 31/343* (2013.01); *A61K 31/35* (2013.01); *A61K 31/357* (2013.01); *A61K 31/437* (2013.01); *A61K 31/4425* (2013.01); *G01N 33/5011* (2013.01); *G01N 2500/10* (2013.01)

(58) Field of Classification Search
CPC . C07D 215/28; A61K 31/4375; A61K 31/47; A61K 31/122; A61K 31/343; A61K 31/35; A61K 31/437; A61K 31/4425; G01N 33/5011
USPC ...................... 546/7; 514/19.4–19.8; 549/358
See application file for complete search history.

(56) References Cited

PUBLICATIONS

Lee J. et al. Dihydroartemisinin downregulates vascular endothelial growth factor expression and induces apoptosis in chronic myeloid leukemia K562 cells. Cancer Chemother Pharmacol, 2006;57:213-220.

Wang Z, et al. Dihydroartemisinin induces autophagy and inhibits the growth of iron-loaded human myeloid leukemia K562 cells vio ROS toxicity. FEBS Open Bio, 2012;2:103-112.

Zhour HJ, et al. Dihydroartemisinin induces apoptosis in human leukemia cells HL60 via downregulation of transferring receptor expression. Anti-Cancer Drugs, 2008;19:247-255.

Wang SJ, et al. Dihydroartemisinin inactivates NF-kB and potentiates the anti-tumor effect of gemcitabine on pancreatic cancer both in vitro and in vivo, Cancer Letters, 2010;293:99-108.

Gao N, et al. Interruption of the MEK/ERK signaling cascade promotes dihydroarternisinin-induced apoptosis in vitro and in vivo. Apoptosis, 2011;16:511-523.

Chen HH, et al. Antimalarial dihydroartemisinin also inhibits angiogenesis. Cancer Chemother Pharmacol, 2004;53:423-432.

(Continued)

*Primary Examiner* — T. Victor Oh
(74) *Attorney, Agent, or Firm* — Henry D. Coleman; R. Neil Sudol

(57) ABSTRACT

In one embodiment, the invention provides a method of inhibiting cAMP efflux and increasing intracellular cAMP in a subject who suffers from, or who is at risk of developing, a cancer by administering to the subject a therapeutically-effective amount of a cAMP efflux inhibitor. Novel compounds, pharmaceutical compositions, diagnostics and screening methods are also provided.

27 Claims, 14 Drawing Sheets

(56) References Cited

PUBLICATIONS

Wang SJ, et al. Dihydroartemisinin inhibits angiogenesis in pancreatic cancer by targeting the NF-kB pathway. Cancer Chemother Pharmacol 2011;68:1421-1430.

Wu XH, et al. Dihydroartemisinin inhibits angiogenesis induced by multiple myeloma RPMI8226 cells under hypoxic conditions via downregulation of vascular endothelial growth factor expression and suppression of vascular endothelial growth factor secretion. Anti-Cancer Drugs, 2006;17:839-648.

Zhou HJ, et al. Dihydroartemisinin improves the efficiency of chemotherapeutics in lung carcinomas in vivo and inhibits murine Lewis lung carcinoma cell line growth in vitro. Cancer Chemother Pharmacol, 2010:66:21-29.

Chen M. et al. Dihydroarteminsin-Induced Apoptosis is not Dependent on the Translocation of Bim to the Endoplasmic Reticulum in Human Lung Adenocarcinoma Cells. Pathol Oncol Res, 2012;18:809-816.

Puel O, et al. Biosynthesis and Toxicological Effects of Patulin. Toxins, 2010;2:613-631.

De Melo FT, et al. DNA damage in organs of mice treated acutely with patulin, a known mycotoxin. Food and Chemical Toxicology, 2012;50:3548-3555.

Wu TS, et al. Activation of ERK mitogen-activated protein kinase in human cells by the mycotoxin patulin. Toxicology and Applied Pharmacology, 2005;207:103-111.

Lai L, Tan Tmc. Role of glutathione in the multidrug resistance protein 4 (MRP4/ABCC4)-mediated efflux of cAMP and resistance to purine analogues. Biochem J, 2002;361:497-503.

Ferrer E, et al. Reactive oxygen species induced by beauvericin, patulin and zearalenone in CHO-K1 cells. Toxicology in Vitro, 2009;23:1504-1509.

Fribley AM, et al. Complementary Cell-Based High Throughput Screens Identify Novel Modulators of the Unfolded Protein Response. J Biomol Screen, 2011;16(8):825-835.

Kawauchiya T, et al. Correlation between the destruction of tight juncfion by patulin treatment and Increase of phosphorylation of ZO-1 in Caco-2 human colon cancer cells. Toxicology Letters, 2011;205:198-202.

Guo X, et al. Patulin induces pro-survival functions via autophagy inhibition and p62 accumulation. Cell Death and Disease, 2013,4:e822.

Kwon O, et al. Patulin induces colorectal cancer cells apoptosis through EGR-1 dependent ATF3 up-regulation. Cell Signal, 2012,24(4):943-950.

Liu BH, et al. Induction of Oxidative Stress Response by the Mycotoxin Patulin in Mammalian Cells. Toxicological Sciences, 2007-95(2):340-347.

Ge Y, et al. Ciyptotanshirione induces cell cycle arrest and apoptosis of multidrug resistant human chronic myeloid leukemia cells by inhibiting the activity of eukaryotic initiation factor 4E. Mol Cell Biochem, 2012;368:17-25.

Kai-Wing A, et al. The Herbal Compound Cryptotanshinone Restores Sensitivity in Cancer Cells That are Resistant to the Tumor Necrosis Factor-related Apoptosis-inducing Ligand. J Biol Chem; 2013;288:29923-29933.

Chen L, et al. Cryptotanshinone has diverse effects on cell cycle events in melanoma cell lines with different metastatic capacity. Cancer Chemother Pharmacol, 2011;68:17-27.

Wu Cy, et al. Cryptotanshinone down-regulates androgen receptor gnalino by modulating lysine-specific demethylase 1 function. Int. J Cancer, 2011:1-12.

Chen W, et al. Cryptotanshinone Inhibits Cancer Cell Proliferation by Suppressing Mammalian target of Rapamycin-Mediated Cyclin D1 Expression and Rb Phosphorylation. Cancer Prey Res, 2010;3:1015-1025.

Jung JH, et l. Apoptosis Induced by Tanshinone IIA and Cryptotanshinone is Mediated by Distinct JAK/STAT3/5 and SHP1/2 Signaling in Chronic Myeloid Leukemia K562 Cells. Hindawi Publishing Corporation, vol. 2013, Article ID 805639, 10 pages. http://dx.doi.org/10.1155/2013/805639.

Nizzmutdinova IT, et al. Tanshinone I effectively induces apoptosis in estrogen receptor-positive (MCF-7) and estrogen receptor-negative (MDA-MB-231) breast cancer cells. International Journal of Oncology, 2008;33:485-491.

Shin DS, et al. Cryptotanshirione Inhibits Constitutive Signal Transducer and Activator of Transcription 3 Function through Blocking the Dimerization in DU145 Prostate Cancer Cells. Cancer Res, 2009;69:193-202.

Dai H, et al. Coexisted components of Salvia miltiorrhiza enhance intestine absorption of cryptotanshinone via inhibition of the intestinal P-gp. Phytomedicine, 2012;19:1256-1262.

Cao B, et al. The Antiparasitic Clioquinol Induces Apoptosis in Leukemia and Myeloma Cells by Inhibiting Histone Deacetylase Activity. J Biol Chern, 2013,288:34181-34189.

Ding WQ, et al. Anticancer Activity of the Antibiotic Clioquinol. Cancer Res, 2005;65:3389-3395.

Yu H, et al. Clioquinol targets zinc to lysosomes in human cancer cells. Biochem J, 2009;417:133-139.

Yu H, et al. Clioquinol Independently Targets NF-kB and Lysosome Pathways in Human Cancer Cells. Anticancer Research, 2010;30:2087-2092.

Zheng J, et al. Clioquinol Suppresses Cyclin D1 Gene Expression through Transcriptional and Post-transcriptional Mechanisms. Anticancer Research, 2011;31:2739-2748.

Daniel KG, et al. Clioquinol and pyrrolidine dithiocarbamate complex with copper to form proteasome inhibitors and apoptosis inducers in human breast cancer cells. Breast Cancer Research, 2005;7:R897-R908.

Mao X, et al. Clioquinol inhibits the proteasome and displays preclinical activity in leukemia and myeloma. Leukemia, 2009;23:585-590.

Chen D, et al. Clioquinol, a Therapeutic Agent for Alzheimer's Disease, Has Proteasome-Inhibitory, Androgen Receptor—Suppressing, Apoptosis-Inducing, and Antitumor Activities in Human Prostate Cancer Cells and Xenografts. Cancer Res, 2007;67:1636-1644.

Du T, et al. Clioquinol Promotes Cancer Cell Toxicity through Tumor Necrosis Factor alpha Release from Macrophages. The Journal of Pharmacology and Experimental Therapeutics, 2008.

Schimmer AD, et al. A Phase I Study of the Metal Ionophore Clioquinol in Patients With Advanced Hematologic Malignancies. Clinical Lymphoma, Myeloma & Leukemia, 2012;12(5):330-336.

Zhou J. et al. Cancer stem/progenitor cell active compound 8-quinolinol in combination with paclitaxel achieves and improved cure of breast cancer in the mouse model. Breast Cancer Res Treat, 2009;115:269-277.

Naderi EH, et al. Activation of cAMP Signaling Interferes with Stress-Induced p53 Accumulation in All-Derived Cells by Promoting the Interaction between p53 and HDM2(1,2). Neoplasia, 2011;13:653-663.

Gerlo S, et al. Cyclic AMP: a selective modulator of NF-kB action. Cell Mol Life Sci, 2011;68:3823-3841.

Guzman ML, et al. Nuclear factor-kB is constitutively activated in primitive human acute myelogenous leukemia cells. Blood, 2011;98(8):2301-2307.

Kloster MM, et al. Hyperactivaton of NF-kB via the MEK signaling is indispensable for the inhibitory effect of cAMP on DNA damage-induced cell death. Molecular Cancer, 2011;10:45.

Ollivier V, et al. Elevated Cyclic AMP Inhibits NF-kB-mediatecl Transcription in Human Monocytic Cella and Endothelial Cells. J Biol Chem; 1996;271:20828-20805.

Shaw TJ, et al. Cyclic AMP in Ovarian Cancer Cells Both Inhibits Proliferation and Increases c-KIT Expression. Experimental Cell Research, 2002;273:95-106.

Stork PJS, Schmitt JM. Crosstalk between cAMP and MAP kinase signaling in the regulation of cell proliferation. Trends in Cell Biology, 2002;12(6)258-266.

Alers S, et al. Role of AMPK-mTOR-Ulk1/2 in the Regulation of Autophagy. Cross Talk, Shortcuts, and Feedbacks. Molecular and Cellular Biology, 2012;32(1):2-12.

Rocha AS, et al. Cyclic AMP Inhibits the Proliferation of Thyroid Carcinoma Cell Lines through Regulation of CDK4 Phosphorylation. Molecular Biology of the Cell, 2008;19:4818-4825.

(56) References Cited

OTHER PUBLICATIONS

Murray F, Insel PA. Targeting cAMP in chronic lymphocytic leukemia: a pathway-dependent approach for the treatment of leukemia and lymphoma. Expert Opin Ther Targets, 2013;17(8):931-949.

Hanahan D, Weinberg RA. Hallmarks cf Cancer: The Next Generation. Cell, 144;2011:646-674.

Dou AX, Wang X. Cyclic adenosine monophosphate signal pathway in targeted therapy of lymphoma. Chinese Medical Journal, 2010;123(1):95-99.

Francis SH, et al. Mammalian Cyclic Nucleotide Phosphodiesterases: Molecular Mechanisms and Physiological Function. Physiol Rev, 2011;91:651-690.

Cheepala S, et al. Cyclic Nucleotide Compartmentalization: Contributions of Phosphodiesterases and ATP-Binding Cassette Transporters. Annu Rev Pharmacol toxicol, 2013;53:231-253.

Zambon AC, et al. Increased Expression of the Pro-apoptotic Protein BIM, a Mechanism for cAMP/Protein Kinase A (PKA)-induced Apoptosis of Immature T Cells. J Biol Chem, 2011,286:33260-33267.

Coffino P. et al. Mechanism of Cell Death Induced by Cyclic AMP. American Journal of Pathology, 1075,81:199-204.

Follin-Arbelet V, et al. Cyclic AMP induces apoptosis in multiple myeloma cells and inhibits tumor development in a mouse myeloma model. BMC Cancer, 2011;11:301.

Carlson CC, et al. 8-Cl-Adenosine-Induced Inhibition of Colorectal cancer Growth In Vitro and In Vivo. Neoplasia, 2000;2(5):441-449.

Insel PA, et al. Cyclic AMP is both a pro-apoptotic and anti-apoptotio second messenger. Acta Physiol, 2012;204 (2):277-287.

Shayo C, et al. The time-course of cyclic AMP signaling is critical for leukemia U-937 cell differentiation. Biochemical and Biophysical Research Communication, 2004;314:798-804.

Copsel S, et al. Multidrug Resistance Protein 4 (MRP4/ABCC4) Regulates cAMP Cellular Levels and Controls Human Leukemia Cell Proliferation and Differentiation. J Biol Chem, 2011;286:6979-6988.

Oevermann L, et al. Hematopoietic stem cell differentiation affects expression and function of MRP4 (ABCC4), a transport protein for signaling molecules and drugs. Int J Cancer. 2009;124:2313-2311.

Zhou S, et al. The ABC transporter Bcrp1/ABCG2 is expressed in a wide variety of stem cells and is a molecular determinant of the side-population phenotype. Nature Medicine, 2001:7(9):1028-1034.

Conley JM, et al. Development of a High-Throughput Screening Paradigm for the Discovery of Small-Molecule Modulators of Adenylyl Cyclase: Identification of an Adenylyl Cyclase 2 Inhibitor, J Pharmacol Exp Ther, 2013;347:276-287.

Lerner A, Epstein PM. Cyclic nucleotide phosphodiesterases as targets for treatment of haematological malignancies. Biochem J., 2006;393:21-41.

Meyers JA, et al. Chronic Lymphocytic Leukemia and B and T Cells Differ in Their Response to Cyclic Nucleotide Phosphodiesterase Inhibitors. The Journal of Immunology, 2009;182:5400-5411.

Scavennec J, et al. Relationship between the Levels of Cyclic chytidine 3'/:5'-Monophosphate, Cyclic Guanosine 3':5'-Monophosphate, and Cyclic Adenosine 3':5'-Monophosphate in Urines and Leukocytes and the Type of Human Leukemias. Cancer Res, 1981;41:3222-3227.

Peracchi M, et al. Plasma and urine cyclic nucleotide levels in patients with acute and chronic leukemia. Blood, 1983:61 429-434.

Okada CY, Rechsteiner M. Introduction of Macromolecules into Cultured Mammalian Cells by Osmotic Lysis of Piniocytic Vesicles. Cell, 1982;29:33-41.

Chandler CJ, Segel IH, Mechanism of the Antimicrobial Action of Pyrithione: Effects on Membrane Transport, ATP Levels, and Protein Synthesis. Antimicrob Agents Chemother, 1978:14(1):60-68.

Lamore SD, Cabello CM. The topical antimicrobial zinc pyrithione is a heat shock response inducer that causes DNA damage and PARP-dependent energy crisis in human skin cells. Cell Stress and Chaperones, 2010;15:309-322.

Morrissey KM, et al. The UCSF-FDA TransPortal: A Public Drug Transporter Database. Clinical Pharmacology & Therapeutics, 2012;92(5):545-546.

Borst P, et al. Multidrug resistance-associated proteins 3, 4, and 5. Eur J Physiol, 2007;453:661-673.

Guillemin MC, et al. In Vivo Activation of cAMP Signaling Induces Growth Arrest and Differentiation in Acute Promyelocytic Leukemia. J Exp Med, 2002;196(10):1373-1380.

Kumar S, et al. Soluble Adenylyl Cyclase Controls Mitochondria-dependent Apoptosis in Coronary Endothelial Cells. J Biol Chem, 2009;284(22):14760-14768.

Xie J, et al. cAMP inhibits mammalian target of rapamycin complex-1 and -2 (mTORC1 and 9) by promoting complex dissociation and inhibiting mTOR kinase activity, Cell Signal, 2011;23(12):1927-1935.

Czyz M, et al. Cell context-dependent actiyites of parthenolide in primary and metastatic melanoma cells. British Journal of Pharmacology, 2010;160:1144-1157.

Saadane A, et al. Parthenolide Inhibits IkB Kinase, NF-kB Activation, and Inflammatory Response in Cystic Fibrosis Cells and Mice. Am J Respir Cell Mol Biol, 2007;36:728-736.

Hehner SP, et al. The Antiinflammatory Sesquiterpene Lactone Parthenolide Inhibits NF-kB by targeting the I kB Kinase Complex, J Immunol, 1999;163:5617-5623.

Kwok BHB, et al. The anti-inflammatory natural product parthenolide from the medicinal herb Feverfew directly binds to and inhibits IkB kinase. Chemistry and Biology, 2001;8:759-766.

Saadane A, et al. Parthenolide inhibits ERK and AP-1 which are dysregulated and contribute to excessive IL-8 expression and secretion in cystic fibrosis cells. Journal of Inflammation, 2011;8:26.

Dai Y, et al. The NF (Nuclear Factor)-kB inhibitor parthenolide interacts with histone deacetylase inhibitors to induce MKK7/JNK1-dependent apoptosis in human acute myeloid leukaemia cells. British Journal of Haematology, 2010;151:70-83.

Zhou J, et al. NF-kB pathway inhibitors preferentially inhibit breast cancer stem-like cells. Breast Cancer Res Treat, 2008,111(3):419-427.

Guzman ML, et al. An orally bioavailable parthenolide analog selectively eradicates acute myelogenous leukemia stem and progenitor cells. Blood, 2007;110(13):4427-4435.

Steele AJ, et al. The sesquiterpene lactone parthenolide induces selective apoptosis of B-chronic lymphocytic leukemia cells in vitro. Leukemia, 2006;20:1073-1079.

Czyz M. et al. Parthenolide reduces the frequency of ABCB5-positive cells and clonogenic capacity of melanoma cells from anchorage independent melanospheres. Cancer Biology & Therapy, 2013;14(2):135-145.

Chen T, et al. Dihydroartemisinin induces apoptosis and sensitizes human ovarian cancer cells to carboplatin therapy. J Cell Mol Med, 2009;13(7):1358-1370.

Cabello CM, et al. The redox antimalarial dihydroartemisinin targets human metastatic melanoma cells but not primary melanocytes with induction of NOXA-dependent apoptosis. Invest New Drugs, 2012;30(4):1289-1301.

Disbrow GL, et al. Dihydroartemisinin is Cytotoxic to Papillomavirus-Expressing Epithelial Cells In vitro and In vivo. Cancer Res, 2005:65:10854-10861.

He Q, et al. Dihydroartemisinin upregulates death receptor 5 expression and cooperates with TRAIL to induce apoptosis in human prostate cancer cells, Cancer Blology & Therapy, 2010;9(10:819-824.

Huang XJ, et al. Dihydroartemisinin exerts cytotoxic effects and inhibits hypoxia inducible factor-1alpha activation in C6 glioma cells. Journal of Pharmacy and Pharmacology, 2007;59:849-856.

Jiao Y, et al. Dihydroartemisinin is an inhibitor of ovarian cancer cell growth. Acta Pharmacol Sin 2007;28(7):1045-1056.

Chen H, et al. Growth inhibitory effects of dihydroartemisinin on pancreatic cancer cells: involvement of cell cycle arrest and inactivation of nuclear factor-kB. J Cancer Res Clin Onvol, 2010;136:897-903.

Handrick R, et al. Dihydroartemisinin Induces Apoptosis by a Bak-Dependent Intrinsic Pathway. Mol Cancer Ther, 2010;9:2497-2510.

(56) References Cited

OTHER PUBLICATIONS

Zhang CZ, et al. Dihydroartemisinin exhibits antitumor activity toward hepatocellular carcinoma in vitro and in vivo. Biochemical Pharmacology, 2012;83:1278-1289.

Ji Y, et al. Anti-tumor effects of dihydroartemisinin on human osteosarcoma. Mol Cell Biochem, 2011,351:99-108.

Lu JJ, et al. Di hydroartemisinin induces apoptosis in HL-60 leukemia cells dependent of iron and p38 mitogen-activated protein kinase activation but independent of reactive oxygen species. Cancer Biology & Therapy, 2008;7(7):1017-1023.

Lu YY, et al. Single-cell analyses of dihydroartemisinin-induced apoptosis through reactive oxygen species-mediated caspase-8 activation and mitochondrial pathway in ASTC-a-1 cells using fluorescence imaging techniques. Journal of Biomedical optics, 2010:15(4):046028.

Kong R, et al. Dihydroartemisinin Enhances Apo2L/TRAIL-Mediated Apoptosis in Pancreatic Cancer Cells vis ROS-Mediated Up-Regulation of Death Receptor 5. PLoS ONE, 2012,7(5):e37222.

Ba Q. et al. Dihydroartemisinin Exerts Its Anticancer Activity through Depleting Cellular Iron via Transferrin Receptor-1. PLoS ONE, 2012;7(8):e42703.

Naviglio S, et al. Protein kinase A as a biological target in cancer therapy. Expert Opin Ther Targets, 2009;13(1):83-92.

Savai R, et al. Targeting cancer with phosphodiesterase inhibitors. Expert Opin Investig Drugs, 2010;19(1):117-131.

Belinsky MG, et al. Multidrug Resistance Protein 4 Protects Bone Marrow, Thymus, Spleen, and Intestine from Nucleotide Analogue-Induced Damage. Cancer Res, 2007;67:262-268.

Takeuchi K et al. Expression levels of multidrug resistance-associated protein 4 (MRP4) in human leukemia and lymphoma cell lines, and the inhibitory effects of the MRP-specfic inhibitor MK-571 on methotrexate distribution in rats. Experimental and Therapeutic Medicine, 2012;4:524-532.

Baumann K. A metabolic switch. Nature Reviews: Molecular Cell Biology, 2013;14:Research Highlights.

Chen ZS, Tiwari AK. Multidrug resistance protein (MRPs/ABCCs) in cancer chemotherapy and genetic diseases. FEBS Journal, 2011;278:3226-3245.

Van Aubel Ramh, et al. The MRP4/ABCC4 Gene Encodes a Novel Apical Organic Anion Transporter in Human Kidney Proximal Tubules: Putative Efflux Pump for Urinary cAMP and cGMP. J Am Soc Nephrol, 2002;13:595-603.

Ding XW, et al. ABCG2: A potential marker of stem cells and novel target in stem cell and cacner therapy. Life Sciences, 2010,86:631-637.

Rico JF, et al. Acute myelogenous leukemia stem cells: From Bench to Bedside. Cancer Letters, 2013:338:4-9.

Shi Z, et al. Roles for Sildenafil in Enhancing Drug Sensitivity in Cancer. Cance Res, 2011;71(11):3735-3738.

Hothip, et al. High-Throughput Chemical Screens Identify Disulfiram as an Inhibitor of Human Glioblastoma Stem Cells. Oncotarget, 2012;3:1124-1136.

Chen H, et al. Dihydroartemisinin inhibits growth of pancreatic cancer cells in vitro and in vivo. Anti-Cancer Drugs, 2009;20:131-140.

Andersson A, al. Gene expression profiling of leukemic cell lines reveals conserved molecular signatures among subtypes with specific genetic aberrations. Leukemia, 2005;19:1042-1050.

Akiyama T, et al. Bim targeted cancer therapy: A link between drug action and underlying molecular changes. Mol Cancer Ther, 2009;8:3173-3180.

Amin HM, et al. Having a higher blast percentage in circulation than bone marrow: clinical implications in myelodysplastic syndrome and acute lymphoid and myeloid leukemias. Leukemia, 2005;19:1567-1512.

Chigaev A, et al. Nitric oxide/cGMP pathway signaling actively down-regulates alpha4beta1-integrin affinity: an unexpected mechanism for inducing cell de-adhesion. BMC Immunology, 2011;12:28.

Gausdal G, et al. Cyclic AMP can promote APL progression and protect myeloid leukemia cells against anthracycline-inclused apoptosis. Cell Death and Disease, 2013;4:e516.

Insel PA, et al. Cyclic: AMP is both a pro-apoptotic and anti-apoptotic second messenger. Acta Physiol, 2012;204 (2):271-287.

Jiao B et al. 8-CPT-cAMP/all-trans relinoic acid targets t(11:17) acute promyelocytic leukemia through enhanced cell differentiation and PLZF/RARalpha degradation. PNAS, 2013;110(9):3495-3500.

Kato JV, et al. Cyclic AMP-Induced G1 Phase Arrest Mediated by an Inhibitor (p27Kip1) of Cyclin-Dependent Kinase 4 Activation. Cell, 1994;79:487-496.

Lapidot T, et al. How do stem cells find their way home? Blood, 2005;106(6):1901-1910.

Lerner A, Epstein PM. Cyclic nudleotido phosphodiesterases as targets for treatment of haematological malignancies. Biochem J, 2006;393:21-41.

Moon EY, Lerner A. PDE4 inhibitors activate a mitochondrial apoptotic pathway in chronic lymphocytic leukemia cells that is regulated by protein phosphatase 2A. Blood, 2003;101(10):4122-4130.

Nguyen E, et al. Activation of Both Protein Kinase A (PKA) Type I and PKA Type II Isozymes is Required for Retinoid-Induced Maturation of Acute Promyelocytic Leukemia Cells. Mol Pharmacol, 2013;83:1057-1065.

Oevermann L, et al. Hematopoietic stern cell differentiaton affects expression and function of MRP4 (ABCC4), a transport protein for signaling molecules and drugs. Int J Cancer, 2009;124:2303-2311.

Okada CY, Rechsteiner M. Introduction of Macromolecules into Cultured Mammalian Cells by Osmotic Lysis of Pinocytic Vesicles. Cell, 1982;29:33-41.

Peracchi M, et al. Patterns Cyclic Nucleotides in Normal and Leukaemic Human Leucocytes. Br J Cancer, 1980;41:360-311.

Peracchi M, et al. Patterns of Cyclic Nucleotides in Normal and Leukaemic Human Leucocytes. Br J Cancer, 1980;41:360-371.

Petrie K, et al. Differentiation therapy of acute myeloid leukemia: past, present and future. Current Opinion in Hematology, 2009,16:84-91.

Quenech'du, N, et al. A sustained increase in the endogenous level of cAMP reduces the retinoid concentration required for APL cell maturation to near physioiogical levels. Leukemia, 1998;12:1829-1833.

Ruchaud S, et al. Two distinctly regulated events, priming and triggering, during retinoid-induce, maturation and resistance of NB4 promyelocytic leukemia cell line. Proc Natl Acad Sci USA, 1994;91:8428-8432.

Savai R, et al. Targeting cancer with phosphodiesterase inhibitors. Expert Opin Investig Drugs,2010;19(1):117-131.

Scavennec J, et al. Relationship between the Levels of Cyclic cytidine 3':5'-Monophosphate, Cyclic Guanosine 3':5'- Monophosphate, and Cyclic Adenosine 3':5'-Monophosphate in Urines and Leukocytes and the Type of Human Leukemias. Cancer Res, 1981;41:3222-3227.

Shayo C, et al. Histamine Modulates the Expression of c-fos through Cyclic AMP Production via the H2 Receptor in the Human Promonocytic Cell Line U937. Molecular Pharmacology; 1997;51:983-990.

Shayo C, et al. The time-course of cyclic AMP signaling is critical for leukemia U-937 cell differentiation. Biochemical and Biophysical Research Communications, 2004;314:798-804.

Shen ZX, et al. All-trans retinoic acid/As2O3 combination yields a high quality remission and survival in newly diagnoses acute promyelocytic leukemia. PNAS, 2004;101(15):5328-5335.

Wang ZY, Chen Z. Acute promyelocytic leukemia: from highly fatal to highly curable. Blood, 2008;111(5):2505-2515.

Zambon AC, Wilderman A. Increased Expression of the Pro-apoptotic Protein BIM, a Mechanism for cAMP/Protein Kinase A (PKA)-induced Apoptosis of Immature T Cells. J Biol Chem, 2011;286:33260-33267.

Zhao Q, et al. Rapid induction of cAMP/PKA pathway during retinoic acid-induced acute promyelocytic leukemia cell differentiation. Leukemia, 2004,18:285-292.

Zhu Q, et al. Synergic effects of arsenic trioxide and cAMP during acute promyelocytic leukemia cell maturation subtends a novel signaling cross-talk. Blood, 2002;99(3):1014-1022.

Chigaev A, et al. Galpha(s)-coupled receptor signaling actively down-regulates alpha4beta1-integrin affinity: A possible mechanism for cell de-adhesion. BMC Immunology, 2008;9:26.

Alexa Fluor® 488 8-(6-Aminohexyl)
aminoadenosine 3´,5´-Cyclicmonophosphate

Figure 8

| Calculated ABCC4-specific binding sites from antibody binding assay | |
|---|---|
| MHH Call 3 | 133.71 |
| Nalm 6 | 5109.23 |
| RS4;11 | 9539.45 |
| Reh | 529.34 |
| 697 | 4358.00 |
| Sup B15 | 3888.98 | a cAMP accumulation of tested cell types after overnight incubation with hit compounds, in dose response b

METHOD FOR CANCER CELL REPROGRAMMING

CROSS REFERENCE TO RELATED APPLICATIONS

This application claims priority from U.S. Provisional Patent Application No. 61/810,060, entitled "Method for Cancer Cell Reprogramming", filed Apr. 9, 2013. The complete contents of this provisional application are hereby incorporated by reference in their entirety.

STATEMENT REGARDING FEDERAL FUNDING

To date, this invention has not been developed through use of federal funding.

FIELD OF THE INVENTION

In one embodiment, the invention provides a method of inhibiting cAMP efflux and increasing intracellular cAMP in a subject who suffers from, or who is at risk of developing, a cancer by administering to the subject a therapeutically-effective amount of a cAMP efflux inhibitor. Novel compounds, pharmaceutical compositions, diagnostics and screening methods are also provided.

BACKGROUND OF THE INVENTION

One of the breakthroughs in the treatment of leukemia was the discovery that one of the AML subtypes can be induced to undergo terminal differentiation (18). This led to the discovery of all-trans-retinoic acid (ATRA), and the first ATRA-based treatments resulted in complete remission in a large number of cases (26). Consequently, studies aimed at identifying novel approaches that can be employed for differentiation therapy of AML are considered indispensable (18).

3'-5'-cyclic adenosine monophosphate (cAMP) is implicated in apoptosis, adhesion and differentiation. Multiple hematological malignancies are associated with a deficiency in apoptosis, and cAMP, the first described second messenger, is implicated in the induction of apoptosis and cell differentiation(6). A number of researchers have suggested utilization of the cAMP-related pathways to increase programmed cell death in hematological malignancies(10-12). The pro-apoptotic pathway, promoted by cAMP, depends upon PKA and involves an intrinsic mitochondria-dependent mechanism. Multiple (Bcl)-related family proteins that include pro-apoptotic Bax, Bak, Bad, Bim and anti-apoptotic (such as Bcl-2) proteins are implicated in the release of cytochrome c and Smac (second mitochondria-derived activator of caspases/DIABLO (direct IAP-binding protein with low pI). An increased expression of the Bim protein in response to cAMP/PKA-induced apoptosis was required for induction of G1 phase cell cycle arrest and apoptosis(27). However, the signaling pathway leading from the elevation of cAMP to apoptotic cell death is still under active investigation, and the exact therapeutic targets can be cell-type specific and may vary from patient to patient.

The loss of integrin-dependent adhesion is one of the early hallmarks in the development of precancerous lesions. In solid tumors, such as breast or ovarian cancer, integrins provide a signal that maintains cell attachment to the basal membrane, and supports cell polarization. Loss of beta 1 integrin-dependent adhesion results in a perturbation of normal cell morphology, and can play a role in tumor development. Furthermore, mobilization of hematopoietic progenitors/blasts into the peripheral blood, which is dependent on the alpha 4 beta 1 integrin (VLA-4)(9), can correlate with more aggressive disease in certain leukemias(2). Our recent discovery that cyclic nucleotides (cAMP(4), and 3'-5'-cyclic guanosine monophosphate (cGMP)(3)) can actively down regulate VLA-4 integrin ligand-binding affinity, rapidly down-modulate cell adhesion, and possibly, induce mobilization of hematopoietic progenitors suggested a specific role of these cyclic nucleotides in hematological malignancies.

Furthermore, cAMP is shown to play an important role in leukemic cell differentiation. The cell-permeable analog of cAMP induces differentiation in the human promonocytic U937 cell line(23; 24). The cytoplasmic level of cAMP in this cell line was modulated through the H2 histamine receptor, which at the same time can induce VLA-4 integrin de-activation and cell de-adhesion(4). Thus, it is plausible that modulation of the cAMP level, rather than targeting individual proteins downstream of the cAMP signal, can be utilized as a tool for cell differentiation therapy.

cAMP is synthesized by the family of enzymes termed adenylate cyclases (adenylyl cyclases, ACs). Enzyme activity is controlled by two classes of GPCRs: GalphaS-coupled stimulate cyclase activity, and GalphaI-coupled inhibit the enzyme. Next, cAMP can be hydrolyzed by the superfamily of enzymes called 3',5'-cyclic nucleotide phosphodiesterases (PDEs), which can have different specificities (cAMP vs. cGMP), localization, and regulation. PDEs are accepted targets for treatment of hematological malignancies, and a number of PDE inhibitors are being tested in different model systems (10).

Another underappreciated mechanism is the removal of the cyclic nucleotides from the cytoplasm by the ATP-binding cassette transporter (ABC-transporter) family of proteins. According to the UCSF-FDA TransPortal database only two transporters, MRP4 and MRP5 are implicated in the active removal of cAMP. Moreover, MRP4 is expressed on the plasma membrane of CD34+ cells, exhibits higher binding affinity for cAMP (vs. cGMP), and the expression of MRP4 (but not MRP5) significantly decreases during leukocyte differentiation (14). This suggests that un-differentiated cell phenotypes can have an increased ability to remove cAMP from the cytoplasm. We recognize that other transporters may participate in this process.

Several clinical studies point toward a specific role of cyclic nucleotides in patients with leukemia. In the urine of patients with four types of leukemia (AML, CML, ALL, and CLL) the concentration and urinary excretion of cyclic nucleotides was higher than in healthy volunteers, with the largest difference between acute leukemia patients and control groups (22). In addition, the plasma level of cyclic nucleotides correlated with the stage of the disease, and it was different in patients who attained remission vs. relapsed individuals (17). At the same time, in WBCs, the cAMP concentration in leukemic cells was lower than in normal cells (16; 22). Based on these and other data we proposed that certain leukemic cells have developed a mechanism that actively removes the pro-apoptotic second messenger (cAMP) from cells into the blood, thus protecting the cell from apoptosis. Since cAMP is excreted through the kidneys, this mechanism explains the lower intracellular cAMP content in leukemic cells (cAMP is continuously removed), the higher plasma and urine concentrations, and the correlation between cAMP concentration and disease progression.

Several recent reviews discuss cyclic nucleotide modulation as a possible option for cancer therapy. Because overexpression of PDE isoforms has been described in several cancers, PDE inhibitors are envisioned as a viable option to restore normal nucleotide metabolism (10; 21). Downstream effectors of the cAMP/PKA-induced apoptotic pathway (such as the Bim protein) are also under investigation for targeting in cancer (1). The interest in cAMP and cGMP efflux in the cancer field was stimulated mainly by the fact that cyclic nucleotides represent natural substrates for multi-drug resistance proteins (MRPs/ABCCs), implicated in the efflux of anti-cancer drugs, and not usually envisioned as a mechanism for modulating the signaling for cell reprogramming.

The idea that cell "maturation", resistant to ATRA-induced differentiation, can be promoted by cAMP-elevating agents, or by using cAMP analogs, is nearly twenty years old (20). An increase in cellular cAMP reduces the effective concentration of ATRA required to achieve maturation(19). The role of the cAMP pathway in t(15;17) APL has been studied for many years. They uncovered cross-talk between arsenic trioxide and cAMP signaling (29), described the rapid increase in cAMP and PKA expression after ATRA treatment (28), and showed the benefits of the ATRA/arsenic trioxide combination for therapy of APL (25). Several recent reports highlight the role of cAMP/PKA-signaling for cell differentiation. The cAMP analog/ATRA combination is shown to improve the differentiation of t(11;17)(q23;q21) APL cells, the subset carrying PLZF/RARa fusion that poorly responds to ATRA (7). The activation of the two PKA isozymes is required for ATRA-induced maturation of APL cells (13). Thus, our attention to the mechanisms, modulating cAMP levels is well justified. A seemingly surprising result that the treatment of blasts with cAMP-elevating agents protects cell from cytotoxic drugs (5), can be also interpreted according to our hypothesis: the same class of proteins, which is implicated in the cAMP regulation, can also mediate drug resistance.

SUMMARY OF THE INVENTION

The present invention is directed to the unexpected discovery that cancer cells can be reprogrammed by initiating apoptotic escape by blocking the removal of the second messenger in a cancer cell. To that end, a number of compounds have been identified which show activity as inhibitors of cAMP efflux. These compounds show activity as inhibitors of cAMP efflux and consequently, are identified as inhibitors of cancer cell apoptotic escape, one of the principal mechanisms which enable tumors to grow and elaborate. Further, the compounds are effective anticancer agents which find use as inhibitors of the removal of the second messenger in cancer cells, resulting in restoration of the apoptosis of cancer cells as well as treatment and prevention of cancer, especially including metastasis of cancer, through a novel mechanism. The compounds may be used alone or in combination with other anticancer agents to treat and/or reduce the likelihood of cancer, including especially metastatic cancer.

Compounds according to the present invention may also be used as ligands in assays which are used to identify compounds which exhibit activity as inhibitors of cAMP efflux and as agents to restore apoptosis in cancer cells.

In one aspect of our invention, we have discovered novel small-molecule-based methods of reprogramming a population of cancer cells to reestablish an apoptotic escape. In one aspect of our invention, compounds which exhibit activity as inhibitors of cAMP efflux reprogram cancer cells, thereby restoring an anti-apoptotic mechanism and inhibiting and treating cancer, including metastatic cancer.

Exemplary compounds which find use in the present invention include the following compounds (most of which are also set forth in FIG. 1, attached hereto):

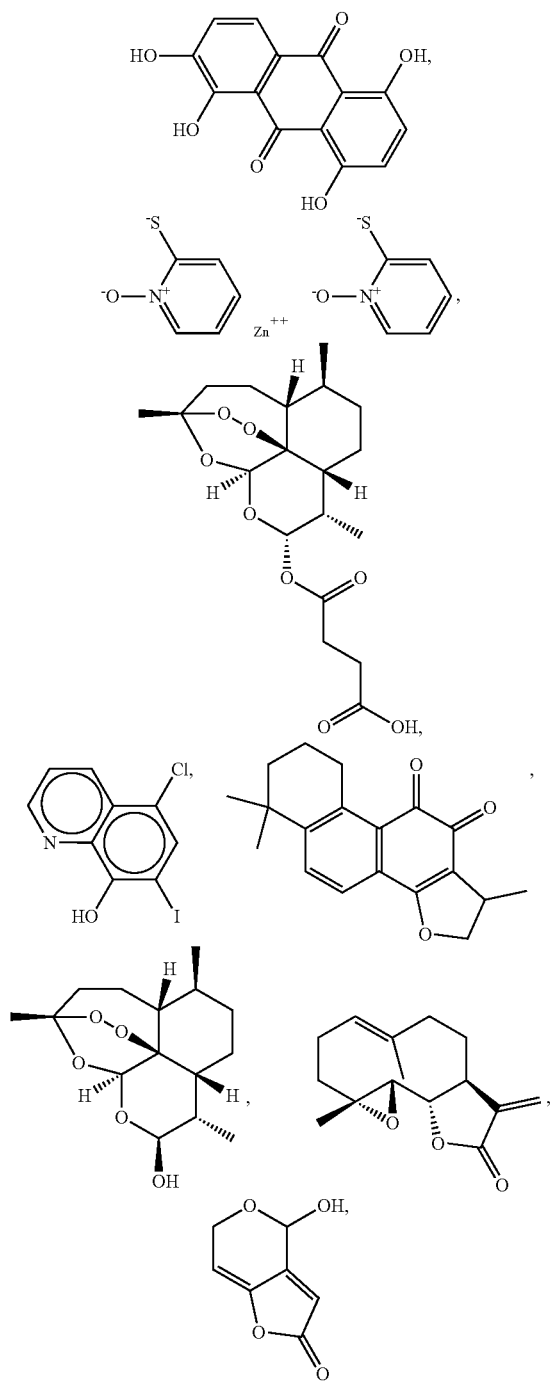

harmalol, artenisinin and artemether or a pharmaceutically acceptable salt, stereoisomer (including diastereomers and/or enantiomers), solvate or polymorph thereof.

In further embodiments, the present invention also relates to methods for treating or reducing the likelihood of cancer or reducing the likelihood of metastasis in a patient in need, comprising administering a therapeutically-effective amount of one or more inhibitors of cAMP efflux, e.g. at least one compound selected from the group consisting of

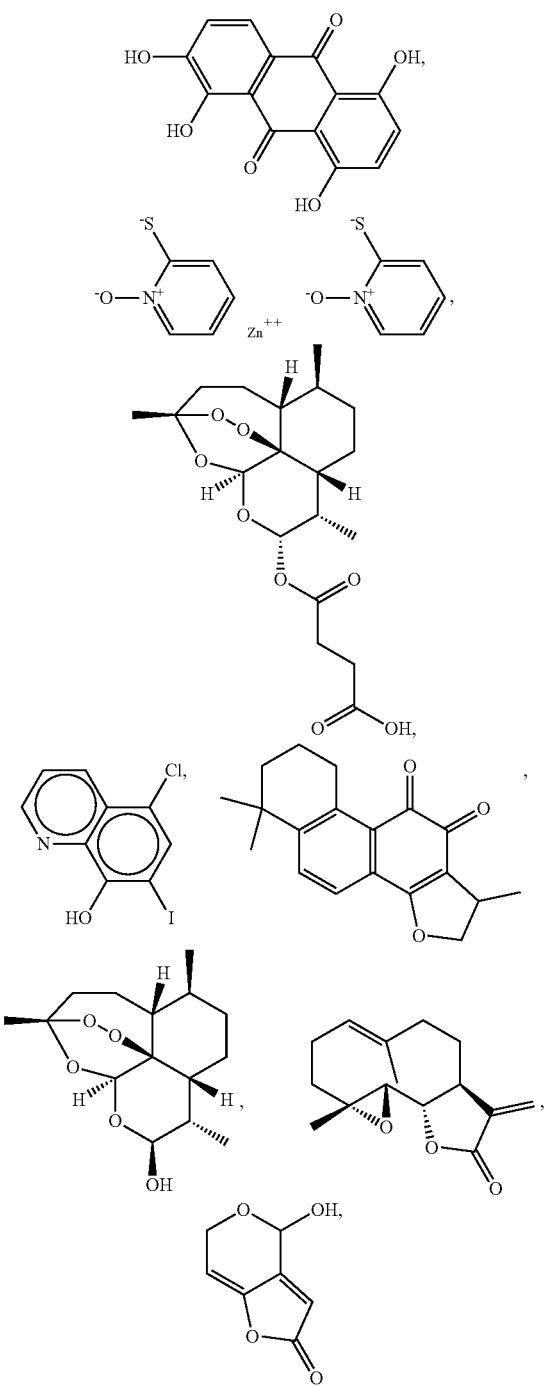
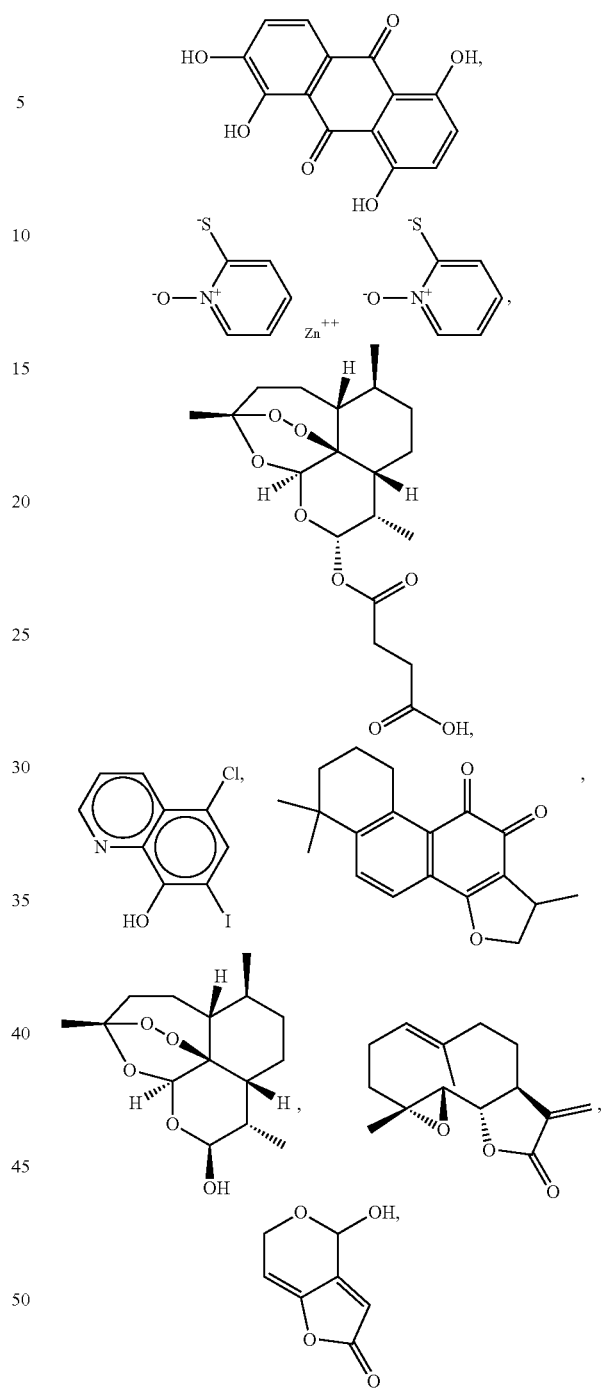

harmalol, artenisinin and artemether or a pharmaceutically acceptable salt, stereoisomer (which term includes diastereomers and enantiomers), solvate or polymorph thereof, in combination with a pharmaceutically acceptable carrier, additive and/or excipient and optionally, at least one additional anticancer agent.

In still additional embodiments, the present invention relates to methods of reprogramming cancer cells to reestablish an apoptotic mechanism comprising exposing said cancer cells to a therapeutically-effective amount of one or more inhibitors of cAMP efflux, e.g. at least one compound selected from the group consisting of harmalol, artenisinin and artemether or a pharmaceutically acceptable salt, stereoisomer, solvate or polymorph thereof, in combination with a pharmaceutically acceptable carrier, additive and/or excipient and optionally, at least one additional anticancer agent.

One embodiment of our invention provides a method of inhibiting cAMP efflux and increasing intracellular cAMP in a subject who suffers from, or who is at risk of developing, a cancer, the method comprising administering to the subject a therapeutically-effective amount of a cAMP efflux inhibitor, preferably a compound selected from the group consisting of artemisinin, artemether, artesunate, dihydroartemisinin, patulin, pyrithione zinc, parthenolide, quinalizarin, clioquinol, cryptotanshinone and harmalol, and the pharmaceutically-acceptable salts, stereoisomers, solvates and polymorphs thereof.

In a preferred embodiment, the subject suffers from one or more cancers selected from the group consisting of kidney cancer, oral squamous cell carcinoma, glioblastoma, colon cancer, colorectal cancer and hematological cancer and is administered a therapeutically-effective amount of patulin or a pharmaceutically-acceptable salt, stereoisomer, solvate or polymorph thereof.

In another preferred embodiment, the subject suffers from one or more cancers selected from the group consisting of melanoma, cervical cancer, hematological cancer, breast cancer and cystic fibrosis and is administered a therapeutically-effective amount of parthenolide or a pharmaceutically-acceptable salt, stereoisomer, solvate or polymorph thereof.

In another preferred embodiment, the subject suffers from one or more cancers selected from the group consisting of ovarian cancer, cervical cancer, breast cancer, liver cancer, melanoma, pancreatic cancer, lung cancer, hematological cancer, prostate cancer, gioma and osteosacoma and is administered a therapeutically-effective amount of artesunate and/or dihydroartemisinin, or a pharmaceutically-acceptable salt, stereoisomer, solvate or polymorph thereof.

In another preferred embodiment, the subject suffers from one or more cancers selected from the group consisting of hematological cancer, breast cancer HeLa, prostate cancer, hematological cancer, melanoma, lung cancer and rhabodomyosarcoma and is administered a therapeutically-effective amount of clioquinol and/or cryptotanshinone or a pharmaceutically-acceptable salt, stereoisomer, solvate or polymorph thereof.

In another embodiment, the invention provides a pharmaceutical compound that inhibits cAMP efflux and increases intracellular cAMP, the composition comprising:
(a) a therapeutically-effective amount of a cAMP efflux inhibitor selected from the group consisting of artemisinin, artemether, artesunate, dihydroartemisinin, patulin, pyrithione zinc, parthenolide, quinalizarin, clioquinol, cryptotanshinone and harmalol, and the pharmaceutically-acceptable salts, stereoisomers, solvates and polymorphs thereof; and, optionally
(b) one or more additional anti-cancer agents and/or a pharmaceutically-acceptable excipient.

In other embodiments, the subject who suffers from one or more of the aforementioned cancers is treated concomitantly by a cAMP efflux inhibitor, one or more additional anti-cancer agents as described herein and, optionally, radiotherapy.

In another embodiment, the invention provides a diagnostic method for determining whether a subject suffers from one or more cancers, the method comprising:
(a) assaying a sample obtained from the subject for levels of cAMP efflux and intracellular cAMP; and
(b) predicting an increased likelihood that the subject suffers from one or more cancers upon detection of elevated levels of cAMP efflux and intracellular cAMP.

In another embodiment, the invention provides a method of determining whether a composition is effective in the treatment of one or more cancers, the method comprising contacting a eukaryotic cell sample with the composition, measuring cellular cAMP efflux, and comparing measured cellular cAMP efflux with levels of cAMP efflux in a control eukaryotic cell sample, wherein reduced expression levels of cAMP efflux when compared to control expression levels indicates that the composition is effective in the treatment of one or more cancers.

In a preferred embodiment, the invention provides a diagnostic method for determining whether a subject suffers from one or more cancers, the method comprising:
(a) assaying a sample obtained from the subject for levels of cAMP efflux and intracellular cAMP by contacting the sample with a fluorescent cAMP analog (F-cAMP) in a flow cytometric assay to monitor cAMP efflux; and
(b) predicting an increased likelihood that the subject suffers from one or more cancers upon detection of elevated levels of cAMP efflux and intracellular cAMP.

The methods and formulations described herein prove particularly effective in treating a wide variety of cancers that have been previously been associated with high rates of remission and poor long-term survival.

These and other aspects of the invention are described further in the Detailed Description of the Invention.

BRIEF DESCRIPTION OF THE FIGURES

FIG. 8. Determination of ATP-binding cassette transporter ABCC4 (ABCC4)-specific binding sites on B-lineage ALL cell lines. ABCC4 is a membrane transporter implicated in cAMP efflux. Specific binding sites were deduced by binding of primary ABCC4 antibody and fluorescent secondary antibody, and analyzed by flow cytometry. Calibration beads allowed mean channel intensity (MCI) values to be converted into non-specific binding sites. Binding site values from IgG primary antibody-bound isotype control cells were subtracted from the ABCC4 non-specific binding site data to calculate the number of ABCC4-specific binding sites per cell.

DETAILED DESCRIPTION OF THE INVENTION

Figure 1:
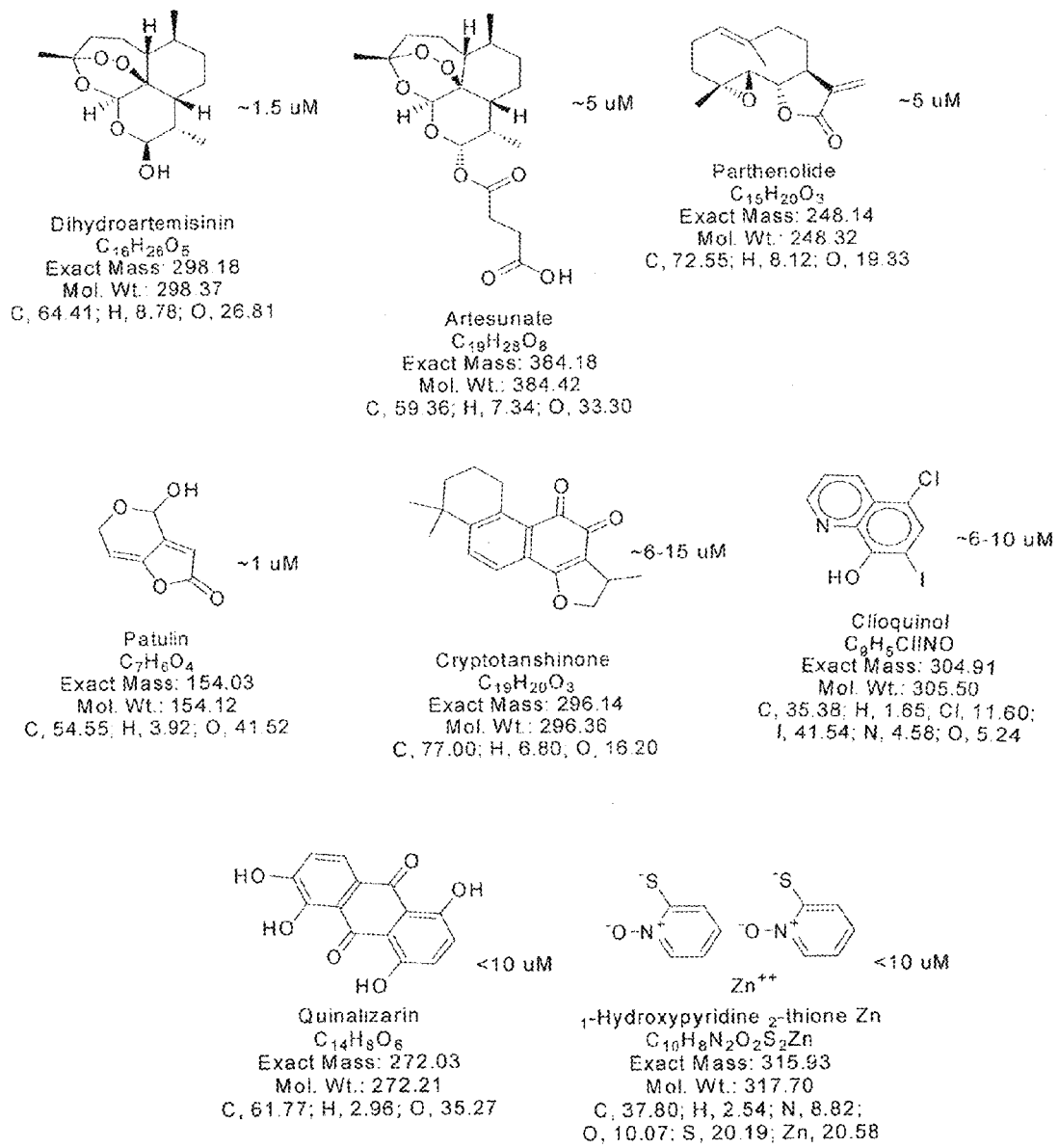
FIG. 1 shows compounds which exhibit activity as inhibitors of cAMP efflux and are useful in the present invention for reprogramming cancer cells, restoring an anti-apoptotic mechanism and in inhibiting and treating cancer, including metastatic cancer.

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

It is noted that, as used in this specification and the appended claims, the singular forms "a," "an," and "the," include plural referents unless expressly and unequivocally limited to one referent. Thus, for example, reference to "a compound" includes two or more different compounds. As used herein, the term "include" and its grammatical variants are intended to be non-limiting, such that recitation of items in a list is not to the exclusion of other like items that can be substituted or other items that can be added to the listed items.

The term "patient" or "subject" is used throughout the specification to describe an animal, preferably a human, to whom treatment, including prophylactic treatment, with the compositions according to the present invention is provided (a patient or subject in need). For treatment of those infections, conditions or disease states which are specific for a specific animal such as a human patient, the term patient refers to that specific animal. In many instances, methods are applied to patients or subjects who are suspected of having cancer, or who have cancer and are suspected of having the cancer metastasize.

The term "compound" is used herein to refer to any specific chemical compound disclosed herein. Within its use in context, the term generally refers to a single small molecule as disclosed herein, but in certain instances may also refer to other forms of the compound, including pharmaceutically acceptable salts, stereoisomers, including diastereomers and enantiomers, solvates and polymorphs. The term compound includes active metabolites of compounds and/or pharmaceutically acceptable salts thereof.

The term "effective amount" is used throughout the specification to describe concentrations or amounts of formulations or other components which are used in amounts, within the context of their use, to produce an intended effect according to the present invention, in this case to reprogram cancer cells by inhibiting efflux of cAMP or to otherwise increase cAMP in cancer cells and restore an apoptotic mechanism to the cell. The formulations or component may be used to produce a favorable change in a disease or condition treated, whether that change is a remission of effects of a disease state or condition, a favorable physiological result, a reversal or attenuation of a disease state or condition treated, the prevention or the reduction in the likelihood of a condition or disease-state occurring, depending upon the disease or condition treated, especially cancer and metastatic cancer. Where formulations are used in combination, each of the formulations is used in an effective amount, wherein an effective amount may include a synergistic amount. The amount of formulation used in the present invention may vary according to the nature of the formulation, the age and weight of the patient and numerous other factors which may influence the bioavailability and pharmacokinetics of the formulation, the amount of formulation which is administered to a patient generally ranges from about 0.001 mg/kg to about 50 mg/kg or more, about 0.5 mg/kg to about 25 mg/kg, about 0.1 to about 15 mg/kg, about 1 mg to about 10 mg/kg per day and otherwise described herein. The person of ordinary skill may easily recognize variations in dosage schedules or amounts to be made during the course of therapy.

The term "prophylactic" is used to describe the use of a formulation described herein which reduces the likelihood of an occurrence of a condition or disease state in a patient or subject. The term "reducing the likelihood" refers to the fact that in a given population of patients, the present invention may be used to reduce the likelihood of an occurrence, recurrence or metastasis of disease in one or more patients within that population of all patients, rather than prevent, in all patients, the occurrence, recurrence or metastasis of a disease state, in this case cancer. In preferred aspects of the invention, compounds according to the present invention may be used to reduce the likelihood of cancer, including metastasis of cancer.

The term "pharmaceutically acceptable" refers to a salt form or other derivative (such as an active metabolite or prodrug form) of the present compounds or a carrier, additive or excipient which is not unacceptably toxic to the subject to which it is administered.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc. Treatment, as used herein, encompasses both prophylactic and therapeutic treatment.

The term "neoplasia" refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis.

As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991.

The term "additional anticancer agent" shall mean chemotherapeutic agents such as an agent selected from the group consisting of microtubule-stabilizing agents, microtubule-disruptor agents, alkylating agents, antimetabolites, epidophyllotoxins, antineoplastic enzymes, topoisomerase inhibitors, inhibitors of cell cycle progression, and platinum coordination complexes. These may be selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, NO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

A "pharmaceutically acceptable salt" of the present compound generally refers to pharmaceutically acceptable salts form of a compound which can form a salt, because of the existence of for example, amine groups, carboxylic acid groups or other groups which can be ionized in a sample acid-base reaction. A pharmaceutically acceptable salt of an amine compound, such as those contemplated in the current invention, include, for example, ammonium salts having as counterion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like. Certain compounds according to the present invention which have carboxylic acid groups or other acidic groups which may form pharmaceutically acceptable salts, for example, as carboxylate salts (sodium, potassium, magnesium, zinc, etc.), are also contemplated by the present invention.

Formulations of the invention may include a pharmaceutically acceptable diluent, carrier, solubilizer, emulsifier, preservative and/or adjuvant. Acceptable formulation materials preferably are nontoxic to recipients at the dosages and concentrations employed. The pharmaceutical formulations may contain materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, 18.sup.th Edition, (A. R. Gennaro, ed.), 1990, Mack Publishing Company.

Optimal pharmaceutical formulations can be determined by one skilled in the art depending upon, for example, the intended route of administration, delivery format and desired dosage. See, for example, REMINGTON'S PHARMACEUTICAL SCIENCES, Id. Such formulations may influence the physical state, stability, rate of in vivo release and rate of in vivo clearance of the antibodies of the invention.

Primary vehicles or carriers in a pharmaceutical formulation can include, but are not limited to, water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical formulations can comprise Tris buffer of about pH 7.0-8.5, or acetate buffer of about pH 4.0-5.5, which may further include sorbitol or a suitable substitute. Pharmaceutical formulations of the invention may be prepared for storage by mixing the selected composition having the desired degree of purity with optional formulation agents (REMINGTON'S PHARMACEUTICAL SCIENCES, Id.) in the form of a lyophilized cake or an aqueous solution. Further, the formulations may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical formulations of the invention can be delivered parenterally. When parenteral administration is contemplated, the therapeutic formulations for use in this invention may be in the form of a pyrogen-free, parenterally acceptable aqueous solution. Preparation involves the formulation of the desired immunomicelle, which may provide controlled or sustained release of the product which may then be delivered via a depot injection. Formulation with hyaluronic acid has the effect of promoting sustained duration in the circulation.

Formulations may be formulated for inhalation. In these embodiments, a stealth immunomicelle formulation is formulated as a dry powder for inhalation, or inhalation solutions may also be formulated with a propellant for aerosol delivery, such as by nebulization. Pulmonary administration is further described in PCT Application No. PCT/US94/001875, which describes pulmonary delivery of chemically modified proteins and is incorporated by reference.

Formulations of the invention can be delivered through the digestive tract, such as orally. The preparation of such pharmaceutically acceptable compositions is within the skill of the art. Formulations disclosed herein that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized Additional agents can be included to facilitate absorption. Diluents, flavorings, low melting point waxes, vegetable oils, lubricants, suspending agents, tablet disintegrating agents, and binders may also be employed.

A formulation may involve an effective quantity of a microparticle containing formulation as disclosed herein in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once the formulation of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

Administration routes for formulations of the invention include orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. The pharmaceutical formulations may be administered by bolus injection or continuously by infusion, or by implantation device. The pharmaceutical formulations also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

A "control" as used herein may be a positive or negative control as known in the art and can refer to a HLTF agonist or antagonist composition (e.g. small molecule), or a control cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. For instance, as can be appreciated by a skilled artisan, a control may comprise data from one or more control subjects that is stored in a reference database. The control may be a subject who is similar to the test subject (for instance, may be of the same gender, same race, same general age and/or same general health) but who is known to not have a fibrotic disease. As can be appreciated by a skilled artisan, the methods of the invention can also be modified to compare a test subject to a control subject who is similar to the test subject (for instance, may be of the same gender, same race, same general age and/or same general health) but who is known to express symptoms of a disease. In this embodiment, a diagnosis of a disease or staging of a disease can be made by determining whether protein or gene expression levels as described herein are statistically similar between the test and control subjects.

As described in U.S. Pat. No. 7,908,091, "the term "profile" includes any set of data that represents the distinctive features or characteristics associated with a tumor, tumor cell, and/or cancer. The term encompasses a "nucleic acid profile" that analyzes one or more genetic markers, a "protein profile" that analyzes one or more biochemical or serological markers, and combinations thereof. Examples of nucleic acid profiles include, but are not limited to, a genotypic profile, gene copy number profile, gene expression profile, DNA methylation profile, and combinations thereof. Non-limiting examples of protein profiles include a protein expression profile, protein activation profile, and combinations thereof. For example, a "genotypic profile" includes a set of genotypic data that represents the genotype of one or more genes associated with a tumor, tumor cell, and/or cancer. Similarly, a "gene copy number profile" includes a set of gene copy number data that represents the amplification of one or more genes associated with a tumor, tumor cell, and/or cancer. Likewise, a "gene expression profile" includes a set of gene expression data that represents the mRNA levels of one or more genes associated with a tumor, tumor cell, and/or cancer. In addition, a "DNA methylation profile" includes a set of methylation data that represents the DNA methylation levels (e.g., methylation status) of one or more genes associated with a tumor, tumor cell, and/or cancer. Furthermore, a "protein expression profile" includes a set of protein expression data that represents the levels of one or more proteins associated with a tumor, tumor cell, and/or cancer. Moreover, a "protein activation profile" includes a set of data that represents the activation (e.g., phosphorylation status) of one or more proteins associated with a tumor, tumor cell, and/or cancer."

The terms "level" and/or "activity" as used herein further refer to gene and protein expression levels or gene or protein activity. For example, gene expression can be defined as the utilization of the information contained in a gene by transcription and translation leading to the production of a gene product.

In certain non-limiting embodiments, an increase or a decrease in a subject or test sample of the level of measured biomarkers (e.g. proteins or gene expression) as compared to a comparable level of measured proteins or gene expression in a control subject or sample can be an increase or decrease in the magnitude of approximately ±5,000-10,000%, or approximately ±2,500-5,000%, or approximately ±1,000-2,500%, or approximately ±500-1,000%, or approximately ±250-500%, or approximately ±100-250%, or approximately ±50-100%, or approximately ±25-50%, or approximately ±10-25%, or approximately ±10-20%, or approximately ±10-15%, or approximately ±5-10%, or approximately ±1-5%, or approximately ±0.5-1%, or approximately ±0.1-0.5%, or approximately ±0.01-0.1%, or approximately ±0.001-0.01%, or approximately ±0.0001-0.001%.

The values obtained from controls are reference values representing a known health status and the values obtained from test samples or subjects are reference values representing a known disease status. The term "control", as used herein, can mean a sample of preferably the same source (e.g. blood, serum, tissue etc.) which is obtained from at least one healthy subject to be compared to the sample to be analyzed. In order to receive comparable results the control as well as the sample should be obtained, handled and treated in the same way. In certain examples, the number of healthy individuals used to obtain a control value may be at least one, preferably at least two, more preferably at least five, most preferably at least ten, in particular at least twenty. However, the values may also be obtained from at least one hundred, one thousand or ten thousand individuals.

A level and/or an activity and/or expression of a translation product of a gene and/or of a fragment, or derivative, or variant of said translation product, and/or the level or activity of said translation product, and/or of a fragment, or derivative, or variant thereof, can be detected using an immunoassay, an activity assay, and/or a binding assay. These assays can measure the amount of binding between said protein molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots and other techniques known to those of ordinary skill in the art (see Harlow and Lane, Antibodies: A Laboratory Manual, Cold Spring Harbor Laboratory Press, Cold Spring Harbor, N.Y., 1999 and Edwards R, Immunodiagnostics: A Practical Approach, Oxford University Press, Oxford; England, 1999). All these detection techniques may also be employed in the format of microarrays, protein-arrays, antibody microarrays, tissue microarrays, electronic biochip or protein-chip based technologies (see Schena M., Microarray Biochip Technology, Eaton Publishing, Natick, Mass., 2000).

Certain diagnostic and screening methods of the present invention utilize an antibody, preferably, a monoclonal antibody, capable of specifically binding to a protein as described herein or active fragments thereof. The method of utilizing an antibody to measure the levels of protein allows for non-invasive diagnosis of the pathological states of kidney diseases. In a preferred embodiment of the present invention, the antibody is human or is humanized. The preferred antibodies may be used, for example, in standard radioimmunoassays or enzyme-linked immunosorbent assays or other assays which utilize antibodies for measurement of levels of protein in sample. In a particular embodiment, the antibodies of the present invention are used to detect and to measure the levels of protein present in a renal cell or urine sample.

Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a disease related protein is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

In order to identify small molecules and other agents useful in the present methods for treating or preventing a renal disorder by modulating the activity and expression of a disease-related protein and biologically active fragments thereof can be used for screening therapeutic compounds in any of a variety of screening techniques. Fragments employed in such screening tests may be free in solution, affixed to a solid support, borne on a cell surface, or located intracellularly. The blocking or reduction of biological activity or the formation of binding complexes between the disease-related protein and the agent being tested can be measured by methods available in the art.

Other techniques for drug screening which provide for a high throughput screening of compounds having suitable binding affinity to a protein, or to another target polypeptide useful in modulating, regulating, or inhibiting the expression and/or activity of a disease, are known in the art. For example, microarrays carrying test compounds can be prepared, used, and analyzed using methods available in the art. See, e.g., Shalon, D. et al., 1995, International Publication No. WO95/35505, Baldeschweiler et al., 1995, International Publication No. WO95/251116; Brennan et al., 1995, U.S. Pat. No. 5,474,796; Heller et al., 1997, U.S. Pat. No. 5,605,662.

Identifying small molecules that modulate protein activity can also be conducted by various other screening techniques, which can also serve to identify antibodies and other compounds that interact with proteins identified herein and can be used as drugs and therapeutics in the present methods. See, e.g., Enna et al., eds., 1998, Current Protocols in Pharmacology, John Wiley & Sons, Inc., New York N.Y. Assays will typically provide for detectable signals associated with the binding of the compound to a protein or cellular target. Binding can be detected by, for example, fluorophores, enzyme conjugates, and other detectable labels well known in the art. The results may be qualitative or quantitative.

For screening the compounds for specific binding, various immunoassays may be employed for detecting, for example, human or primate antibodies bound to the cells. Thus, one may use labeled anti-hIg, e.g., anti-hIgM, hIgG or combinations thereof to detect specifically bound human antibody. Various labels can be used such as radioisotopes, enzymes, fluorescers, chemiluminescers, particles, etc. There are numerous commercially available kits providing labeled anti-hIg, which may be employed in accordance with the manufacturer's protocol.

By way of a mechanism of the present invention and without being limited by way of theory, the inventors of the present application postulate that in certain malignancies, the apoptotic escape can be initiated at the level of the second messenger (3'-5'-cyclic adenosine monophosphate (cAMP), for example). The tumor cells develop the mechanism that removes the second messenger from the cytoplasm, and as a consequence, promotes an apoptotic escape, resulting in malignancies. The present invention is based upon the concept that it is possible to reprogram cancer cells by blocking the second messenger removal using drugs or drug-like compounds, which are presented herein. This approach can be applied to the treatment of malignancies on an individualized or patient by patient basis, where second messenger removal represents a part of an anti-apoptotic pathway. Methods of inhibiting, reducing the likelihood or treating cancer, especially including metastatic cancer are important embodiments of the present invention.

Pursuant to the present invention, the inventors propose the following mechanisms for the prevention and/or treating of cancer, including metastatic cancer using compounds according to the present invention:

The inventors propose that accumulation of cAMP represents part of the normal mechanism responsible for the elimination of damaged, precancerous cells.

The inventors further propose that the mechanisms of apoptotic escape, employed by a cancer cell, can be related to a decrease in the cytoplasmic cAMP concentration. This can be achieved by removing cAMP from the cytoplasm by transporters.

The inventors further propose that targeting cAMP efflux using specific blockers as described herein in certain malignancies will overcome apoptotic escape, and thus, provide a novel therapeutic option, particularly effective when combined with additional anticancer agents, which exhibit biological activity separate from the restoration of apoptotic mechanism by compounds according to the present invention.

The inventors also propose that cAMP efflux can be targeted on an individualized (patient by patient) basis with respect to the overexpression of efflux activity, as well as the reprogramming of phenotypic responses including viability, proliferation, apoptosis, cell cycle, and phosphoprotein levels.

The inventors propose that the use of F-cAMP may represent a diagnostic biomarker to predict the responsive of patient cells ex vivo and that the loss of F-cAMP efflux from patient samples may represent a measure of the effectiveness of the proposed treatment.

The inventors propose that a reduction of cAMP in the urine of patients treated with the proposed compounds may represent a measure of the effectiveness of the proposed treatment.

These and other aspects of the invention are illustrated further in the following non-limiting examples.

Example 1

Effect of cAMP Efflux Blockers

To test the basic hypothesis, the inventors developed an assay for the detection of the efflux of the cAMP fluorescent analog, and screened the Prestwick Chemical Library and the SPECTRUM Collection for blockers of cAMP efflux. These libraries are composed of FDA approved drugs and drug-like compounds, and therefore, represent a valuable source for drug repurposing. We identified:

1) A number of structurally related compounds that blocked cAMP-analog efflux in a dose-dependent manner.
2) In secondary assays these compounds when used alone rapidly decreased cell viability, induced cell cycle arrest, and promoted apoptosis. EC50s for cell cycle arrest and apoptosis were comparable with IC50s for cAMP efflux.
3) The normal (non-malignant) human peripheral blood cells were less sensitive to the second messenger blockers, suggesting that removal of the second messenger from the cytoplasm represents a cancer cell-specific mechanism.

Results

Assay for the Detection of Cyclic AMP Efflux

To study the efflux of cAMP from cells we used the Alexa Fluor 488 conjugated cAMP analog (FIG. 2, hereof), commercially available from Life Technologies. U937 cell were loaded with the analog by a method relying on osmotic lysis of pinocytic vesicles (15). After incubation, cell fluorescence decreased to a level that was close to cell autofluorescence. MK-571 is a compound reported to block cAMP efflux in a dose-dependent manner.

High Throughput Flow Cytometry Screen

Using the above-described assay, the inventors screened the Prestwick Chemical Library (Prestwick Chemical) and the SPECTRUM Collection (Microsource Discovery Systems, Inc.) at the University of New Mexico Center for Molecular Discovery (UNMCMD, http://nmmlsc.health.unm.edu/). We have identified four commercially available drugs and several structurally related compounds that blocked cAMP-analog efflux in a dose-dependent manner.

According to the inventors' hypothesis, blocking cAMP efflux should result in the loss of cell viability, cell cycle arrest, and apoptosis. To test this, the inventors performed a number of secondary assays.

Secondary Assays: Cell Viability, Cell Cycle, Proliferation, and Apoptosis

Figure 2:
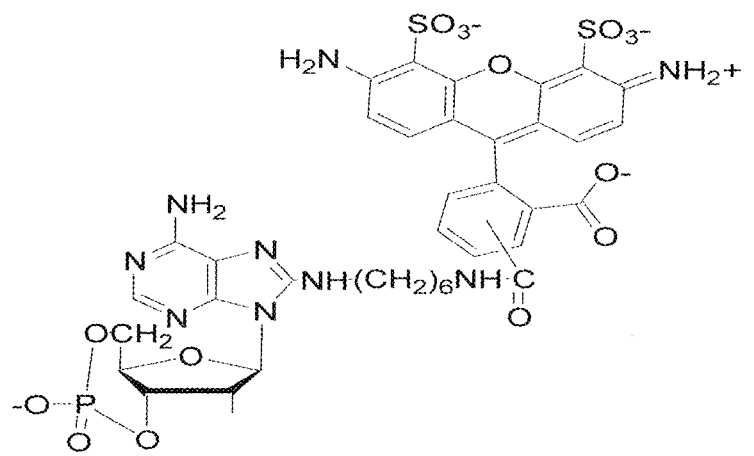
FIG. 2 shows the results of an assay for detecting cyclic AMP efflux. Cells were loaded with the Alexa488-cAMP analog (top). After incubation (16 hours) green fluorescence was measured using a flow cytometer. MK-571 was previously shown to block cAMP efflux, and it has been used as control (bottom).
Figure 2:
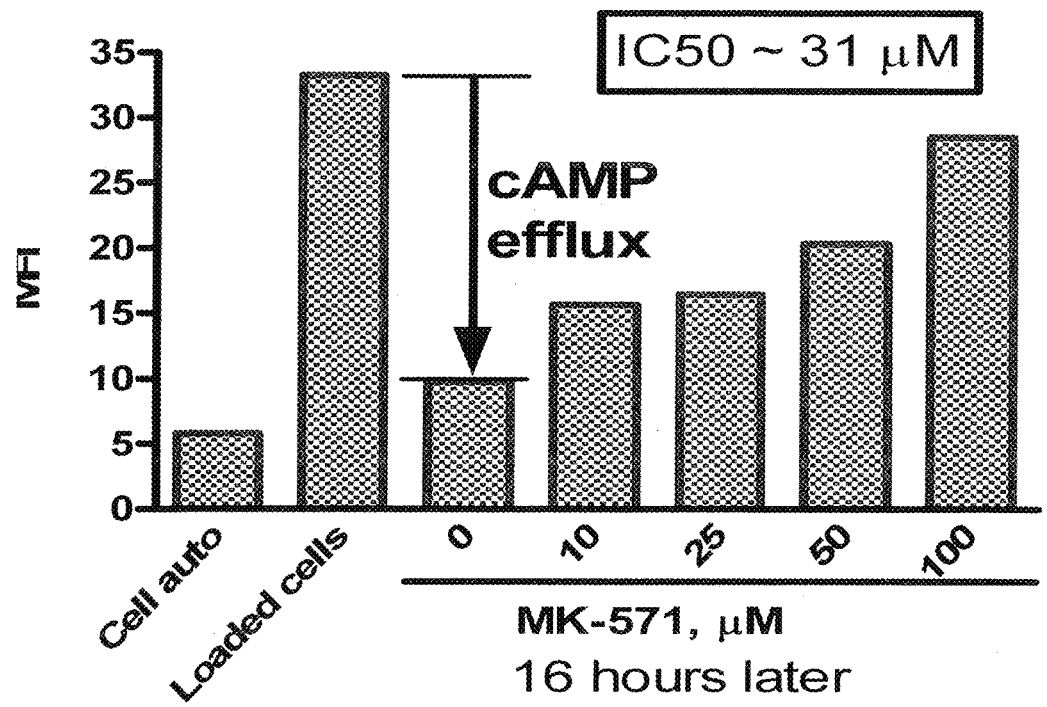
Figure 2A:
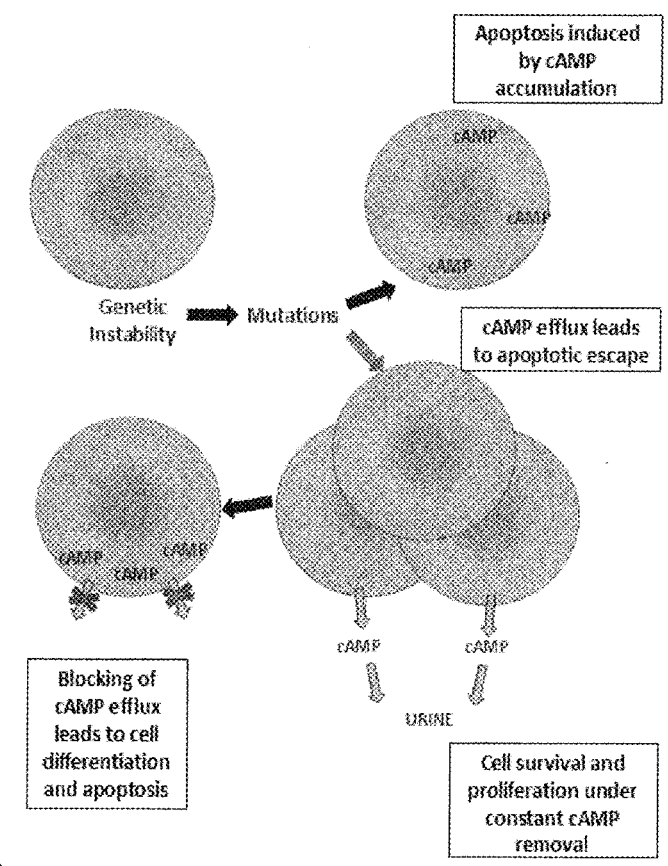
FIG. 2A shows a proposed model for the experiments described in the Examples herein. Somatic cells experience genetic instability, which generates mutations, thus increasing intracellular cAMP. To evade the intrinsic apoptosis induced by elevated intracellular cAMP, cancer cells efflux cAMP, releasing the second messenger into the blood and urine.
Figure 3:
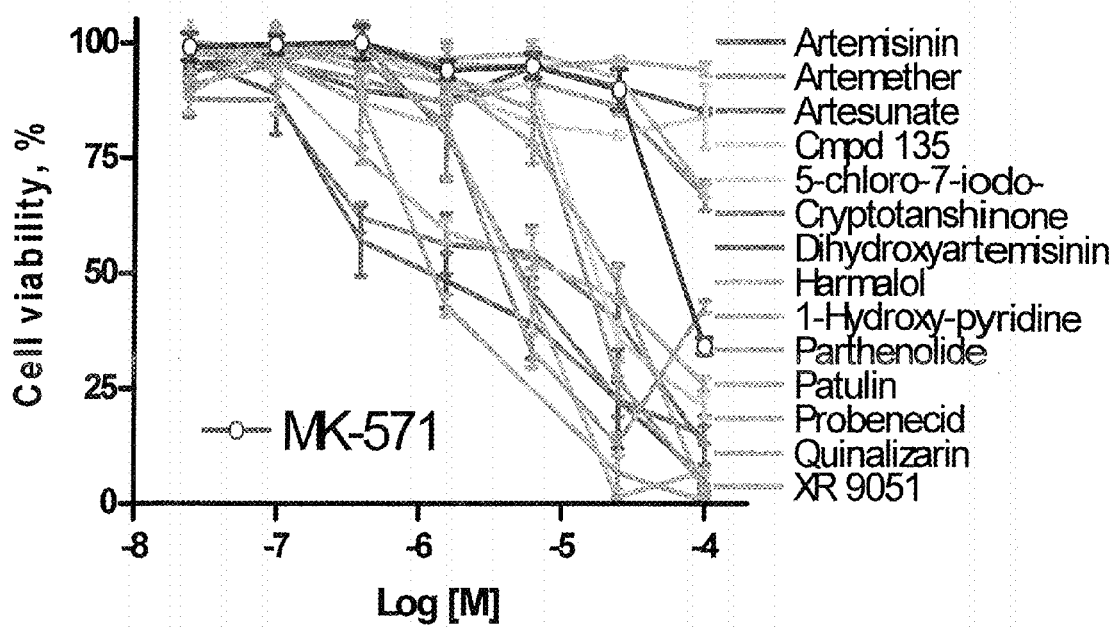
FIG. 3 shows the cell viability as determined using CellTiter-Glo® assay. Cells were incubated for 24 hours with increasing concentrations of compounds identified in the cAMP efflux assay (FIG. 1).

Cell viability. The CellTiter-Glo® luminescent cell viability assay is based on quantification of intracellular ATP and serves as an indicator of metabolically active "viable" cells. Overnight incubation with different concentrations of the screening hits showed a significant decrease in cell viability (FIG. 2). For several compounds, the IC50s were significantly lower as compared to the MK-571 (control). Thus, a number of compounds identified as cAMP efflux blockers were able to rapidly decrease cellular ATP content.

Cell cycle. The inventors used propidium iodide for DNA staining to detect the phases of the cell cycle. Several identified compounds induced cell cycle arrest in the G0/G1 phase, decreasing the percentage of cells in G2/M and S phases in a dose-dependent manner. G1 arrest in monocytes is reported to be controlled by a cAMP/p27/Kip1-related mechanism (8). Seven compounds also exhibited a dose dependent increase in the number of cells with DNA content less than the G0/G1 phase (dead/apoptotic cells). Thus, selected compounds identified as cAMP efflux blockers were able to induce cell cycle arrest/apoptosis when used alone in a dose-dependent manner.

Cell Proliferation. To assess cell proliferation, the inventors used the CellTrace™ CFSE Cell Proliferation Kit. Cells were stained with carboxyfluorescein diacetate succinimidyl ester (CFSE). This dye forms dye-protein adducts that are retained during cell division, and the fluorescent dye was used to quantify cell proliferation. We found that a number of compounds when used at 3-6 µM concentration stopped cell proliferation 48 hours after compound addition. These data were consistent with the results of the cell cycle assay.

Figure 4:
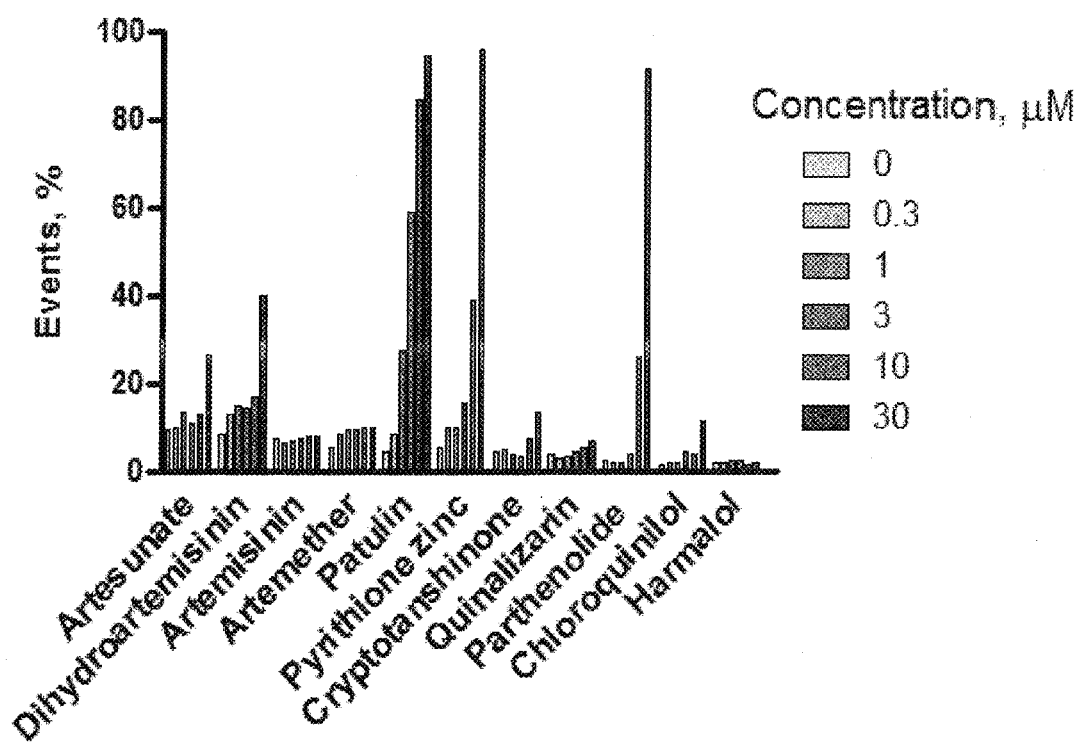
FIG. 4 shows the percent of Annexin V and 7-AAD double positive events plotted vs. the concentration of cAMP efflux blockers. Cells were incubated with increasing concentrations of compounds identified in cAMP efflux assay, and assayed for binding of Annexin V and 7-AAD.

Apoptosis. To detect apoptosis we used an Annexin V and 7-amino-actinomycin D (7-AAD) based assay. Annexin V is a protein that has high binding affinity to phosphatidylserine, which is translocated from the inner to the outer leaflet of the membrane during early apoptosis. 7-AAD is a DNA dye that stains cells only when the cell membranes are permeable. Thus, double positive events are considered to represent end stage apoptosis and dead cells. This assay does not discriminate between cells that have undergone apoptotic death versus a necrotic pathway. Our data indicated that a number of compounds identified as blockers of cAMP efflux induced rapid dose-dependent cell death (FIG. 4). The results obtained using this assay correlated well with the results of other assays:

| Calculated $EC_{50}$ values from Annexin V,7-AAD double positive events, µM | |
| --- | --- |
| Artemisinin | 248.89 |
| Artemether | 106.41 |
| Artesunate | 99.08 |
| Dihydroartemisinin | 55.72 |
| Patulin | 3.29 |
| Pyrithione zinc | 11.22 |
| Parthenolide | 13.52 |
| Quinalizarin | 172.19 |
| Clioquinol | 76.56 |
| Cryptotanshinone | 53.46 |
| Harmalol | 283.14 |

Figure 4A:
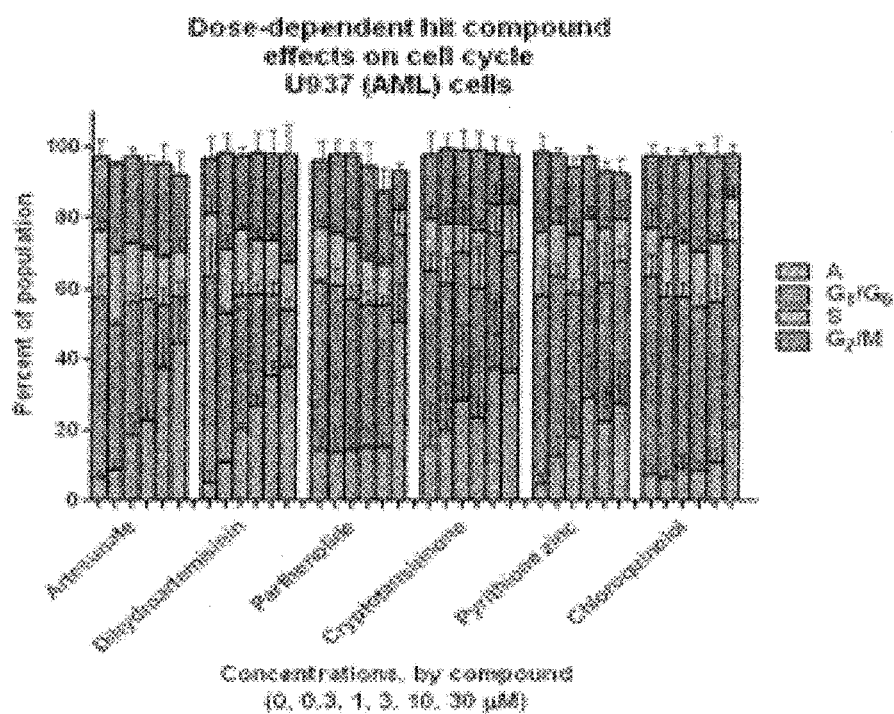
FIG. 4A shows the effects of identified cAMP efflux inhibitors on U937 cell cycle after overnight incubation. B) Bar graph indicating percentages of cells gated in each phase of the cell cycle after dose-dependent treatment with cAMP efflux inhibitors. Gating was done as follows: G1/G0: DNA=2n, S: 2n<DNA<4n, G2/M: DNA=4n, Apoptosis (A): DNA<2n. C) Calculated EC50 concentrations of hit compounds for apoptotic events shown in (B). EC50 values were determined by variable slope log (agonist) vs response fits with the following constraints: top=100, bottom=0.

See also FIG. 4A

Thus, secondary assays confirmed that selected cAMP efflux blockers, when used alone: 1) rapidly induced a decrease in cell viability; 2) induced cell cycle arrest in G0/G1 phase, as consistent with the effect of cAMP(8); 3) rapidly stopped cell proliferation; and 4) induced apoptosis/cell death as measured by Annexin V and 7-Aminoactinomycin D, and DNA fragmentation. EC50s for cell cycle arrest and apoptosis were comparable with IC50s for cAMP efflux. None of the identified compounds were chemotherapeutic drugs.

Another prediction that can be made according to the present invention is that cells that do not possess the cAMP efflux mechanism (for example normal non-cancerous cells) should exhibit less sensitivity to cAMP blockers. This is postulated because normal cells do not require cAMP removal to sustain cell survival. To test this prediction the present inventors compared the effect of cAMP efflux blockers on the viability of peripheral blood mononuclear cells (PBMCs) side by side with U937 cells.

Effect of cAMP Efflux Blockers on Human PBMCs

Figure 5:
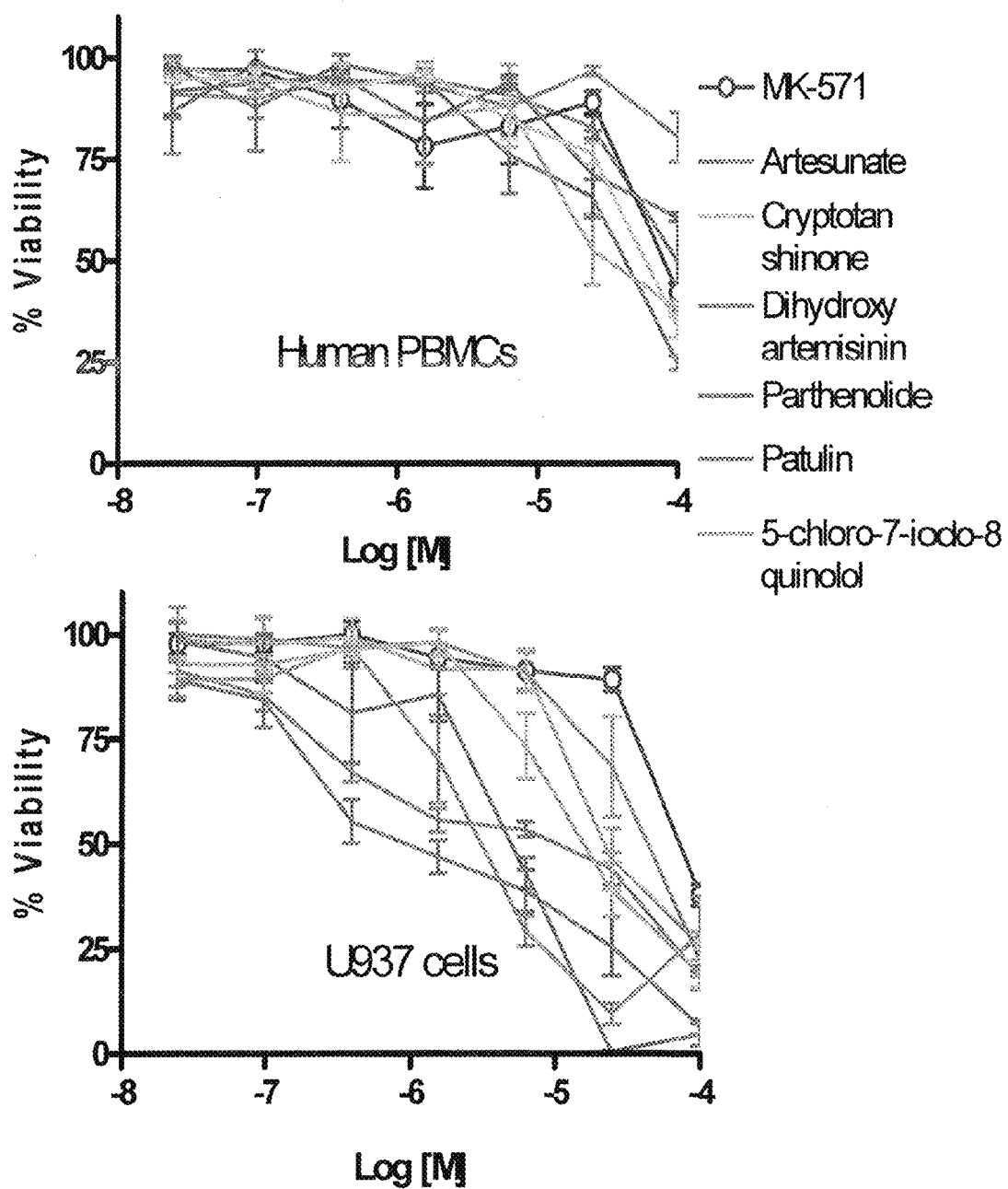
FIG. 5 shows the viability of human PBMCs (top) and U937 cells (bottom) treated side by side with different concentrations of the cAMP efflux blocking compounds determined using the CellTiter-Glo® assay.

The viability curves for human PBMCs, treated with the array of identified compounds showed a significant shift to the right as compared to U937 cells (FIG. 5). This indicates that normal peripheral blood cells were less sensitive to the effect of cAMP blockers.

Figure 5A:
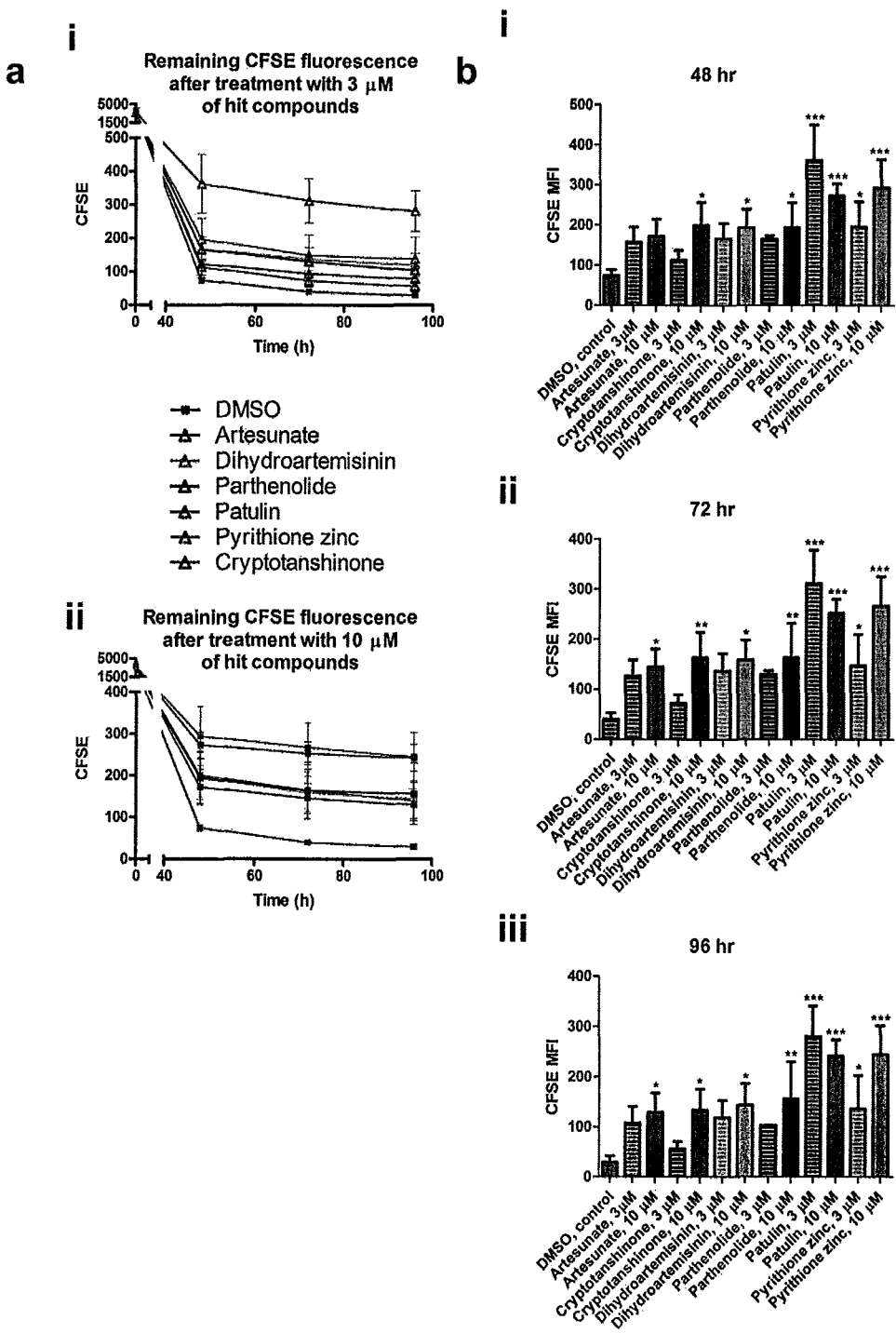
FIG. 5A. Effects of identified cAMP efflux inhibitors on U937 proliferation. Cells were stained with CFSE in bulk, and then separated into cultures containing either solvent, 3 µM, or 10 µM compounds. Samples were taken from cultures after 48, 72, and 96 hours after initial culture time. A and B) Raw data of CFSE MFI in cells remaining after treatment with hit compounds, as measured by flow cytometry. Decreases in CFSE MFI over time indicate cell proliferation. Data in (B) were analyzed by one-way ANOVA with repeated measures with a Dunnett post test to compare treated samples to DMSO control values (n=3, *p<0.05, p<0.01, *p<0.001). Data shown are the result of 3 independent experiments.

FIG. 5A shows the effects of the identified cAMP efflux inhibitors on U937 proliferation. Cells were stained with CFSE in bulk, and then separated into cultures containing either solvent, 3 µM, or 10 µM compounds. Samples were taken from cultures after 48, 72, and 96 hours after initial culture time. A and B) Raw data of CFSE MFI in cells remaining after treatment with hit compounds, as measured by flow cytometry. Decreases in CFSE MFI over time indicate cell proliferation. Data in (B) were analyzed by one-way ANOVA with repeated measures with a Dunnett post test to compare treated samples to DMSO control values (n=3, *p<0.05, p<0.01, *p<0.001). Data shown are the result of 3 independent experiments.

Additionally, the inventors tested the ability of human PBMCs to efflux the Alexa488-cAMP analog in the primary assay, as shown in FIG. 2. The results suggest that U937 cells have a greater ability to remove Alexa488-cAMP analog from the cytoplasm than PBMCs.

Thus, a number of compounds (FIG. 1) identified as blockers of cAMP efflux when used alone stopped cell proliferation, induced the loss of cell viability and cell apoptosis. Normal human peripheral blood mononuclear cells where less sensitive to the effects of the compounds presumably because of the lack of the cAMP removal system that is unnecessary for normal (non-cancerous cell survival).

Example 2

Assessing cAMP-Concentrations after Treatment with Drugs

To test our central hypothesis, we developed a novel assay, and screened the Prestwick Chemical Library (Prestwick Chemical) and the SPECTRUM Collection (Microsource Discovery Systems, Inc.) at the University of New Mexico Center for Molecular Discovery. We found that four commercially available drugs and several structurally related compounds blocked cAMP efflux in a dose dependent manner. Secondary assays confirmed that the compounds identified, when used alone: 1) induced cell cycle arrest in the G1 phase, as consistent with the effect of cAMP; 2) induced apoptosis as measured by Annexin V and 7-Aminoactinomycin D, and DNA fragmentation; 3) rapidly induced a decrease in cell viability. EC50s for cell cycle arrest and apoptosis were comparable with IC50s for the cAMP efflux. Thus, our data provide a proof of concept, and support the central hypothesis. These data have been disclosed as a patent application ("Method for Cancer Cell Reprogramming" (STC ref. 2013-097)).

Next, because several types of genetic rearrangements contribute to cancer cell phenotypes, we studied heterogeneity of cAMP removal systems in a set of genetically diverse cell lines. Two cell lines were shown to have identical genetic rearrangement and a fusion gene (Table 1) (21). The set of proof of principle data disclosed in the patent application was obtained using U937 cell line (AML, t(10;11)(p12;q14), PICALM/MLLT10(AF10)).

TABLE 1

The human cell lines included in the study, their subtype and genetic rearrangements (21)

| Cell line | Subtype | Genetic rearrangement | Fusion gene |
|---|---|---|---|
| 697 (EU-3) | B-lineage ALL | t(1;19)(q23;p13) | TCF3(E2A)/PBX1[1] |
| Nalm-6 | B-lineage ALL | t(5;12)(q33;p13) | |
| Sup-B15 | B-lineage ALL | t(9;22)(q34;q11) | P190 BCR/ABL1 |
| REH | B-lineage ALL | t(12;21)(q13;q22) | ETV6(TEL)/RUNX1(AML1) |
| RS4:11 | B-lineage ALL | t(4;11)(q21;q23) | MLL/MLLT2(AF4) |
| Mhh-Call 3 | B-lineage ALL | t(1;19)(q23;p13) | TCF3(E2A)/PBX1[1] |

[1]Two cell lines have identical genetic rearrangement and a fusion gene.

To study the differences in cAMP-removal, cells were loaded with a fluorescent cAMP-analog, and incubated under different conditions: low temperature (4° C.) used to estimate the passive probe "leakage", and physiological temperature (37° C.) used to assess active removal of the probe. MK-571, a previously reported inhibitor of cAMP efflux, was used to estimate the "pump-dependent" component of the process (19).

Figure 6:
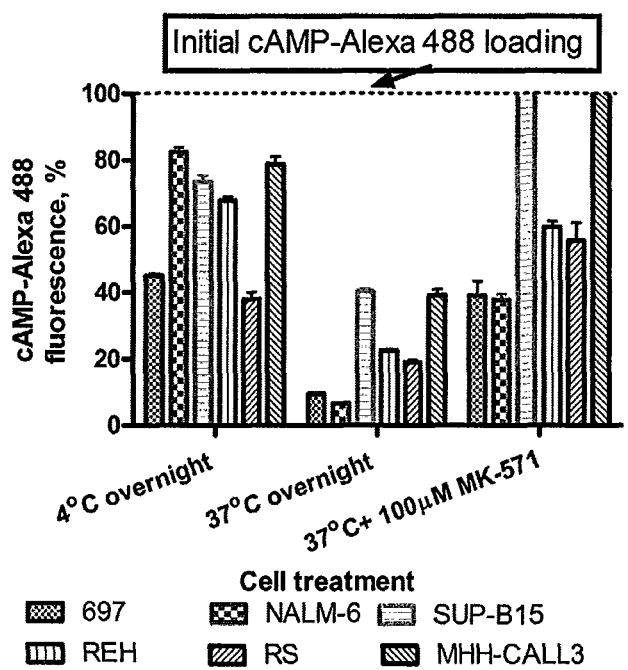
FIG. 6. Removal of cAMP-Alexa 488 probe from different hematopoietic cell lines. Cell autofluorescence was subtracted. The data were normalized to the initial cAMP-fluorescence value. The graph shows remaining fluorescent probe. Therefore, the lowest signal corresponds to the higher probe removal activity.

The cAMP-removal system in cancer cell lines exhibited dramatically diverse behavior (FIG. 6). Because cells loaded with the fluorescent probe were subsequently washed, the resulting concentration gradient can cause a "passive leak" of the probe. After incubation at 4° C., cell lines have lost 20-60% of the initial stain. Incubation at 37° C. resulted in removal of the probe from ~60% for SUP-B15 and MHH-CALL3 cells, down to ~90% for 697 and Nalm-6 cells with no apparent correlation between 4° C. and 37° C. samples. Cell lines also exhibited different sensitivity to the effect of MK-571, a known cAMP-blocker. The response ranged from 0-60%, where "0" corresponds to the absence of efflux. For two cell lines, SUP-B15, and MHH-CALL3, the inhibitor completely blocked cAMP probe efflux. For these cell lines MK-571 blocked not only active probe removal at 37° C., but also efflux at 4° C., and therefore the fluorescent signal was equal to the initial cAMP probe loading value (FIG. 6). Thus, the cAMP removal system exhibited a large degree of variability. Moreover, these effects were not directly related to the type of genetic rearrangement. For the two lines (697 and Mhh-Call3) with an analogous fusion protein (Table 1), the cAMP-removal was drastically different (FIG. 6). This suggests that the genomics/sequencing approaches will not be sufficient for cAMP-efflux prediction.

Figure 7:
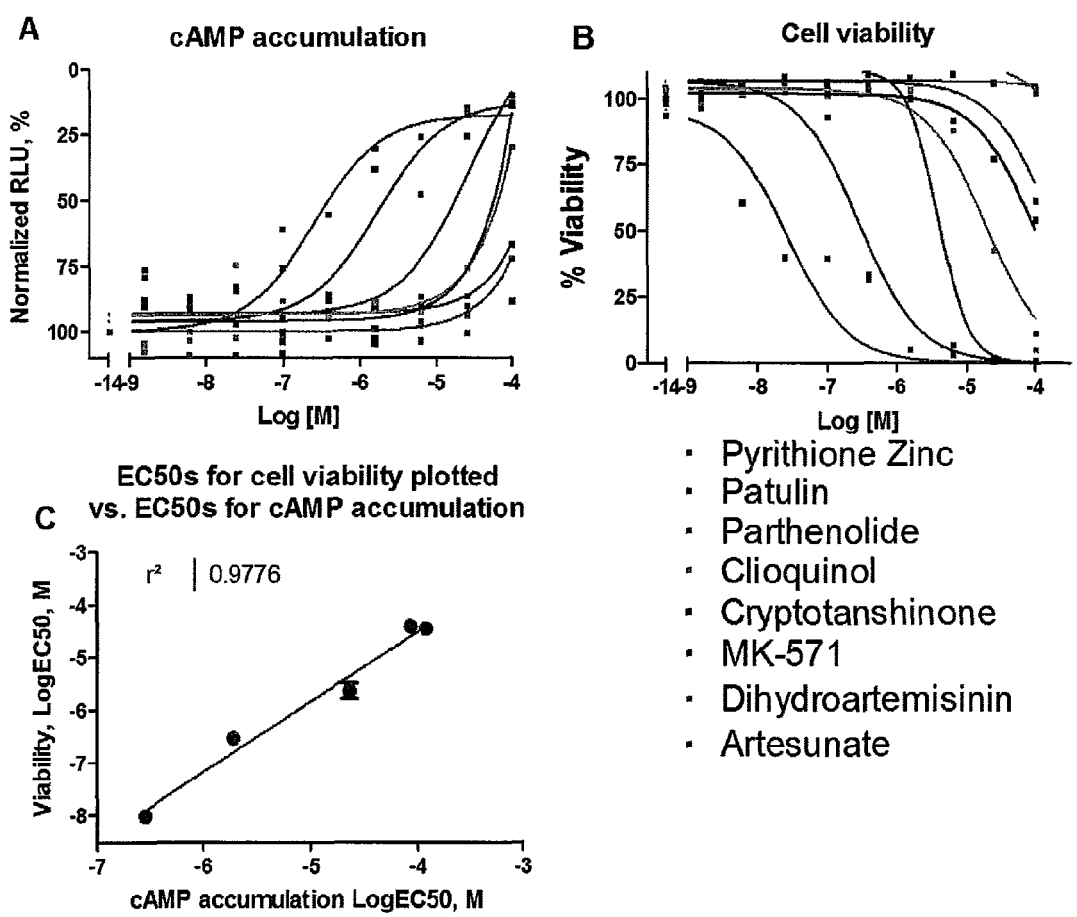
FIG. 7. cAMP accumulation (A), cell viability (B), and a cross correlation between EC50s for cAMP accumulation and cell viability for REH cells. Cells were treated with different concentrations of compound hits. Dose response curves were generated using Graphpad Prism software.

Finally, to establish whether the effects of identified cAMP-efflux blocker compounds on cell viability can be directly linked to the accumulation of cAMP, we studied the dose responses for cAMP accumulation and cell viability (FIG. 7). We observed a correlation between cAMP accumulation and a decrease in the cell viability for seven molecules that were identified in a screen as inhibitors of cAMP-efflux. Quantitatively, the coefficient of determination ($r^2$) for the correlation between EC50s for the drug-induced loss of cell viability plotted versus EC50s for the drug-induced accumulation of cAMP in the cytoplasm was ~0.98 (FIG. 2C), suggesting a very strong correlation.

Taken together, these data support our prediction that assessing cAMP-concentrations after treatment with drugs can serve as a predictor for the efficacy of a particular drug in patient samples. Patient samples will be analyzed in a manner identical to the cell lines (as detailed in Research design and Methods), and samples exhibiting the highest sensitivity to cAMP blocking therapy will be validated for further therapeutic options.

Example 3

Identification of Cyclic AMP Efflux Inhibitors as Potential Therapeutic Agents for Hematological Malignancies Here, we used a fluorescent cAMP analog (F-cAMP) in a flow cytometric assay to monitor cAMP efflux in leukemic cells. Next, to identify compounds and drugs that could inhibit cAMP efflux, we miniaturized the assay into a high throughput screening (HTS) format and screened two small molecule libraries composed of biologically active substances and off-patent drugs in U937 acute myeloid leukemia (AML) cells. The "hits" were validated by secondary assays, which assessed the effect of the compounds on viability, proliferation, cell cycle, and apoptosis. Next, these compounds were tested for effects on cAMP efflux inhibition and viability in B-lineage acute lymphoblastic leukemia (ALL) cells, an AML patient sample, and healthy human primary blood mononuclear cells (PBMCs). Our hypothesis was further supported by measurements of endogenous cAMP accumulation in B-lineage ALL cells after exposure to the hit compounds. Because several of the compounds identified are FDA approved drugs, our studies provide a path for clinical trials of these compounds for drug repurposing [repositioning] against blood cancers.

Materials and Methods

Cells

U937 cells were obtained from ATCC. They were grown in RPMI 1640 medium (supplemented with 2 mM L-glutamine, 100 units/mL penicillin, 100 μg/mL streptomycin, 10 mM HEPES, and 10% heat-inactivated fetal bovine serum (FBS), hereafter referred to as cRPMI), and kept at 37° C. and 5% $CO_2$/95% air.

cAMP Efflux Assay

This method of loading U937 cells with a fluorescent analog of cAMP is based on a procedure described by Okada, et al. 1982[19]. Briefly, cells were concentrated and washed, with resuspension NF-RPMI (cRPMI without FBS). Cells were then resuspended in an NF-RPMI hypertonic solution containing poly(ethylene glycol) 1,000 (PEG), sucrose, and Alexa Fluor® 488 8-(6-aminohexyl) aminoadenosine 3',5'-cyclicmonophosphate, bis(triethylammonium) salt, hereafter referred to as F-cAMP, to give a final concentration of 4.76 mM F-cAMP. Cells were incubated for 10 min, room temperature, then centrifuged and resuspended in hypotonic solution (60% cRPMI, 40% sterile water) for 2 min at room temperature to complete the F-cAMP loading. The cells were then washed and resuspended in cRPMI at a final concentration of 4×10⁵ cells/mL, and allowed to equilibrate for 2 hours in a 37° C., 5% $CO_2$/95% air incubator.

For general testing of cAMP efflux, a small sample of the stained cells was retained and kept at 4° C. overnight to serve as a control. The remainder of the cells was incubated (37° C., 5% $CO_2$/95% air) in the presence of dimethyl sulfoxide (DMSO) vehicle or compounds overnight. Flow cytometry was used to measure samples, and unstained U937 cells were used to create a gate to mark viable cells. Control and experimental samples were excited with a 488 nm laser and analyzed for FL-1 median fluorescence intensity (MFI) within that gate.

High Throughput Screening

For the high throughput screening assay (HTS), U937 cells were loaded with F-cAMP as described above. Solutions were added to 384-well plates (Greiner 784201) with a Biomek FX Multichannel system (Beckman-Coulter) and/or MicroFlo as follows: 1) 5 μL cRPMI; 2) 100 nL compounds from the Prestwick Chemical Library or Spectrum 2000 Library in DMSO were delivered by pintool (V&P Scientific, San Diego, Calif.), final DMSO concentration=1%; 3) 5 µL F-cAMP cells. Negative control wells contained stained cells with 1% DMSO only. For positive controls, F-cAMP cells were treated with 200 µM MK-571. The final concentration for all conditions was 2000 cells/well. The plates were sealed with foil, and incubated (37° C., 5% $CO_2$/95% air) inverted overnight.

After incubation, the 384-well sample plates were analyzed by CyAn flow cytometers (Beckman-Coulter) configured with HyperCyt high throughput auto-sampler systems (IntelliCyt Albuquerque, N. Mex.). The samples were interrogated with 488 nm lasers to assess FL-1 MCI levels.

HTS Data Analysis and Hit Compound Validation

Data from the HTS were analyzed with HyperView software (IntelliCyt, Albuquerque, N. Mex.) and gated on untreated, live cell populations and then time-gated to separate data per well. FL-1 MCI values for the samples were analyzed per plate. Those samples which reported MCI values≥2 standard deviations above the plate mean negative control values were considered "hit" compounds.

To validate the identified samples and decrease the number of potential false-positive compounds, the hit compounds were assayed in a high-throughput dose response assay. This assay set up 384-well plates with the same volumes of F-cAMP cells, cRPMI, and DMSO/compounds as in the HTS, with the plate formats containing 10-well dose responses for each hit compound, at final concentrations ranging 30 µM to 4 nM. These plates were also foil-sealed, and incubated inverted overnight. Post-incubation, the dose response plates were analyzed by high throughput flow cytometry, as above.

The dose response data was fitted by Prism software (GraphPad Software, Inc., La Jolla, Calif.) and normalized for percent response based on sample FL-1 MCI values in comparison to untreated control F-cAMP-loaded cells kept at 4° C. overnight. These analyses lead to the identification of 8 compounds with clear dose response curves and decent $EC_{50}$ values. An additional 3 compounds were identified for testing based on structural relatedness to these 8 key compounds.

Secondary Assays

Apoptosis: Six-well plates were set up with dose responses for each of the 11 hit compounds (artemisinin, artemether, artesunate, dihydroartemisinin, parthenolide, patulin, clioquinol, cryptotanshinone, pyrithione zinc, harmalol, quinalizarin). Each well contained 2.5×10$^6$ U937 cells in 5 mL cRPMI. To each well, 15 µL of compound in DMSO (or vehicle control) was fTadded, giving final concentrations of 0, 300 nM, and 1, 3, 10, and 30 µM. Plates were incubated overnight, at 37° C., 5% $CO_2$/95% air. The compound effects on apoptosis were assessed with an Annexin V-PE/7-aminoactinomycin D (7-AAD) kit (BD Pharmingen™ cat. no. 559763), according to manufacturer protocol, and data were collected with a BD Accuri™ C6 flow cytometer. A gate was set for live cells, and 10,000 gated events were collected per sample. FL-2 versus FL-3 channel dot plots were divided into quadrants and were used to determine percentages of gated cells that were Annexin V$^-$/7-AAD$^-$ (live, healthy cells), Annexin V$^+$/7-AAD$^-$ (early apoptosis), or Annexin V$^+$/7-AAD$^+$ (late, full apoptosis).

Cell cycle: The initial steps of the cell cycle assay were set up with the same U937 cell density, volume, compound addition, culture conditions, and incubation as described for the apoptosis assay above. After 24 hour incubation, the samples were centrifuged and fixed in 5 mL 70% ethanol at 4° C. for at least one week. After fixation, samples were washed with PBS and stained with propidium iodide (PI) staining solution (0.1% v/v Triton X-100, 10 µg/mL PI, 100 µg/mL DNase-free RNase A in PBS) for 30 min at room temperature, in the dark. Samples were then interrogated with a BD Accuri™ C6 flow cytometer, and FL-2 channel histograms were gated to determine percentages of cells that were in apoptotic (<2n DNA), $G_0/G_1$ (2n DNA), S (2n<DNA<4n), or $G_2/M$ (4n DNA) phases of the cell cycle.

Proliferation: To assess cell proliferation in the presence of compounds, the CellTrace™ CFSE (carboxyfluorescein diacetate succinimidyl ester) Cell Proliferation Kit (Molecular Probes®) was used. To incorporate CFSE into U937 cells, 10$^6$/mL cells were resuspended in 25 µM CFSE in PBS, and incubated 15 min in a 37° C. water bath. The cells were centrifuged, resuspended in cRPMI at 10$^5$ cells/mL, and incubated for 30 min in a 37° C. water bath. The cells were then washed once and resuspended in cRPMI at 10$^4$ cells/mL. These CFSE-labeled U937 cells were cultured as follows: 5 mL cells/well in a 6-well tissue culture plate. Each 6-well plate contained a DMSO-only negative/0 µM control. For this assay, only artesunate, dihydroartemisinin, patulin, pyrithione zinc, cryptotanshinone, and parthenolide were tested, at final concentrations of 3 and 10 µM. All plates were kept in a 37° C., 5% $CO_2$/95% air incubator. A small aliquot of freshly-labeled cells was retained and analyzed with a FACScan flow cytometer to determine the MFI for the initial staining. At 48 hr post-CFSE staining, 500 µL volumes were obtained from each sample and analyzed. This was repeated at 72 and 96 hr time points. CFSE MFI values were analyzed by one-way ANOVA with repeated measures, with a Dunnett post test to compare treated samples to DMSO control values.

Viability: Viability of cells in the presence of hit compounds was determined with the Cell TiterGlo® Luminescent Cell Viability Assay (Promega). Opaque, white 96-well tissue culture plates (Greiner Bio-One 655083) received 100 µL medium (cRPMI or 20% FBS cRPMI in the case of MHH Call 3 cells)+/−4×10$^4$ cells/well. Dose responses were 1:4 dilutions of 1 µL of compounds which ranged from final concentrations of 100 µM to 1.53 nM (final DMSO concentration=1%). Wells with DMSO only served as negative controls, while wells with final concentrations of 500 µM daunorubicin served as positive controls. Cells were incubated overnight under normal tissue culture conditions, in 37° C., 5% $CO_2$/95% air incubators. After incubation, the Promega Cell TiterGlo® Luminescent Cell Viability Assay was performed according to manufacturer's protocol.

PBMCs: Healthy human primary blood mononuclear cells (PBMCs) were obtained from volunteers. PBMCs were treated with the same compounds in dose response, and culture conditions, as in the viability assay described above.

Cross-cell line tests for cAMP efflux: These assays followed the methods described for the original cAMP efflux assay for the following B-lineage ALL cell lines: 697, Reh, MHH Call 3, RS4;11, Sup B15, and Nalm 6. Briefly, 15 million cells were loaded with F-cAMP via the osmotic process detailed above. Small volumes of cells were analyzed by flow cytometry post-staining to determine baseline fluorescence values based on MFI. Additional small quantities of cells were kept at 4° C. overnight to serve as controls for passive leakage of cAMP. The remaining cells were split in half, and one group was treated with a final concentration of 100 µM MK-571, while the other received DMSO-only at an equal volume. These two groups of cells were incubated ~24 hr according to standard tissue culture conditions (37° C., 5% $CO_2$/95% air). After incubation, cells were analyzed with flow cytometry for FL-1 MFI.

Cross-cell line high throughput tests of hit compound inhibition of cAMP efflux: This assay was conducted the same as the high throughput hit validation assay described above, with the exception that cell densities were 5,000 per well. Briefly, each B-lineage ALL cell line (697, Reh, MHH Call 3, RS4;11, Sup B15, or Nalm 6) was incorporated with F-cAMP, and cells were loaded into 384-well plates in the presence of the top 8 hit compounds, in dose response, with final concentrations ranging in 1:4 dilutions from 100 µM to 1.53 nM. Plates were sealed with foil and incubated inverted overnight (37° C., 5% $CO_2$/95% air). Post-incubation, plates were vortexed and analyzed by high throughput flow cytometry for residual F-cAMP via FL-1 MFI.

Cross-cell line tests for viability with hit compounds: The B-lineage ALL cell lines 697, Reh, MHH Call 3, RS4;11, Sup B15, and Nalm 6, were run through the Cell TiterGlo® Luminescent Cell Viability Assay with the same compounds, cell densities, and conditions as described above. The top 8 hit compounds were tested: artesunate, dihydroartemisinin, parthenolide, patulin, MK-571, pyrithione zinc, clioquinol, and cryptotanshinone. The same was repeated with a frozen patient AML sample (with the exception that the cell density used was 3,000 cells per well).

Cross-cell line analysis for presence of MRP4 (ABCC4): Two million cells each of 697, Reh, MHH Call 3, RS4;11, Sup B15, and Nalm 6 cell lines were fixed with 80% methanol/$diH_2O$ for 5 min at room temperature. The cells were centrifuged and resuspended in 1 mL 0.3M glycine in a 10% FBS in PBS solution. The samples were divided into 500 µL portions, one each for MRP4 antibody labeling, and IgG isotype control. MRP4 samples were labeled with 1 µg/µL primary MRP4 antibodies (goat, anti-human). Control samples were labeled with 2 µg/µL primary IgG antibodies (goat, anti-human). All primary antibody-labeled samples were incubated for 30 min at room temperature, then washed once with PBS, and resuspended in 500 µL 0.3M glycine in 10% FBS in PBS. Then, 1 µL of FITC x anti-goat secondary antibody was added to all samples, followed by 30 min room temperature incubation. Additionally, one sample was made consisting of a set of Quantum™ Simply Cellular® calibration beads (Bangs Laboratories, Inc.), and this was subjected to the same protocol as with the MRP4 samples. Post-labeling, all samples were run on a BD Accuri™ C6 flow cytometer with 488 nm laser excitation for analysis of FITC (FL-1) MFI. The calibration beads were gated individually, and the median channel fluorescence of these was plotted against known antibody binding complexes (ABCs) per bead, and a linear regression was applied. The derived equation was used to calculate the number of ABCs per sample. Then, for each cell type, the ABC value for IgG isotype control samples was subtracted from that of the MRP4 samples to determine the number of MRP4-specific binding sites.

cAMP accumulation in the presence of hit compounds: This method utilized the Promega cAMP-Glo™ assay kit, and the cell lines U937, 697, Reh, MHH Call 3, RS4;11, Sup B15, and Nalm 6 were tested, along with a sample of healthy PBMCs. Cells were centrifuged 10 min and resuspended in cRPMI supplemented with 500 µM 3-isobutyl-1-methylxanthine (IBMX), 100 µM 4-(3-butoxy-4-methoxy-benzyl)imidazolidone (Ro 20-1724), and 25 mM $MgCl_2$ (cRPMI-IRM) at a density of $2.5 \times 10^6$/mL. The subsequent setup of these plates was the same as occurred in the high throughput cAMP efflux inhibition assay described above, with the exception that there were 12,500 cells/well, and 10 µM forskolin served as positive control. After overnight incubation, 4 µL (5,000 cells) from each well was transferred to opaque white shallow 384-well plates (Greiner Bio-One 784080) for the completion of the cAMP-Glo™ assay. The remainder of the assay was followed according to the manufacturer's protocol, including the usage of a separate assay plate containing known concentrations of cAMP in dose response to generate a standard curve. Briefly, 1 µL of cAMP Detection Solution was added to each well and incubated 20 min at room temperature. Then, 5 µL Kinase-Glo® reagent was added, and plates were incubated a minimum of 10 min at room temperature. A plate reader was used to measure relative luminescence units (RLU) of each well at 1 sec/well. To analyze data, the ΔRLU ((RLU 0 nM cAMP)−(RLU (X nM)) for the standard cAMP concentrations was generated, plotted, and fit with a linear regression analysis. Then, for assay samples, the ΔRLU (RLU (neg. control)−RLU (sample) was calculated and utilized in the linear equation derived from the cAMP standard curve to determine cAMP concentration.

Results

A Fluorescent cAMP Analog can be Used to Measure cAMP Efflux with a High Throughput Screen for Inhibitors by Using Flow Cytometry Earlier studies in U937 cells, an established model for AML, had shown that these cells efflux cAMP. Therefore, we sought to create an assay to assess cAMP efflux in U937 cells. This method is derivative of Okada, 1982[19], in which large molecules were incorporated into cells via induced osmotic lysis of pinocytic vesicles. A fluorescent cAMP analog, Alexa 488-conjugated cAMP (F-cAMP), was loaded into cells, and MFI was assessed after overnight incubation under normal conditions; a sample kept at 4° C. served as a high fluorescence control (data not shown). This strategy is based on the premise that active removal of F-cAMP will cause a decrease in the signal, while those cells retaining F-cAMP would maintain green fluorescence comparable to the control. It has been noted that the compound MK-571 is known to inhibit cAMP efflux[11], and its effectiveness was tested in this assay by adding the compound to cells a few hours after they were loaded with F-cAMP. As shown in FIG. 2, MK-571 down-modulated cAMP efflux in a dose-dependent manner.

These preliminary experiments served as the basis for development of a high throughput screening (HTS) assay to identify drugs and compounds which may potentially block cAMP efflux in leukemic cells. The assay was miniaturized and optimized to work at small volume in 384-well plates. Briefly, bulk amounts of cells were loaded with F-cAMP and allowed to equilibrate for a few hours. Medium, F-cAMP-loaded cells, and test compounds from the Prestwick Chemical Library (~1200 previously FDA-approved drugs) and the SPECTRUM Collection (2320 compounds—60% drugs, 25% natural products, 15% bioactive components) were added to wells in 384-well plates and incubated overnight. DMSO served as a negative control, while 100 µM MK-571, well above the 31 µM $EC_{50}$ calculated in assay development, was the positive control.

Potential "hit" compounds were identified as having MFI's>2 standard deviations above the negative control MFI. This analysis identified 51 hits, and these were tested in dose response to validate their activities in the assay (data not shown). These dose responses yielded 8 potentially useful molecules.

The Identified cAMP Efflux Inhibitors Increased Cancer Cell Apoptosis

The effect of cAMP efflux inhibitors on U937 apoptosis was detected via flow cytometry with the Annexin V-PE/7-amino-actinomycin D (7-AAD) assay to discriminate dead and dying cells. Samples were cultured overnight in the presence of each of the 11 hit compounds, in dose responses ranging 30 µM to 300 nM. The samples were plotted as Annexin V vs 7-AAD and quadrant-gated. Annexin V+, 7-AAD− events are indicative of early apoptosis, in which phosphatidyl serine has flipped to the outer leaflet of the cell membrane. Annexin V+, 7-AAD+ (double positive) events indicate cell and nuclear membrane permeabilization, marking late apoptotic events or complete cell death. The double positive events were the primary focus for this assay, and this is shown in FIG. 4.

Many of the compounds induced apoptosis in U937 cells in a dose-dependent manner, with some compounds producing populations which nearly entirely consisted of double positive events. Line graphs of the dose responses of the most efficacious compounds were plotted, and their $EC_{50}$ values were determined to range from 3.29 μM to 283.14 μM (FIG. 4b). The compounds with the best $EC_{50}$ values, in order from lowest to highest, were patulin, pyrithione zinc, parthenolide, cryptotanshinone, and dihydroartemisinin.

cAMP Efflux Inhibitors Caused Cell Cycle Arrest

To assess the effects of the hit compounds on U937 cell cycle, a propidium iodide (PI) staining assay was conducted. The 11 hit compounds were tested in dose response, under the same conditions as the apoptosis experiments. Samples were analyzed with flow cytometry for PI MFI (see example in FIG. 4A a), and the percentages of the populations within gates for each phase of the cell cycle are plotted in FIG. 4A b. This was relevant, as increased intracellular cAMP is known to arrest cells at $G_1$[5,6]. The most active compounds (artesunate, parthenolide, dihydroartemisinin, and cryptotanshinone) increased percentages of cells in $G_1$ or apoptosis in a dose-dependent manner (FIG. 4A c).

cAMP Efflux Inhibitors Decreased Cell Proliferation

Figure 6A:
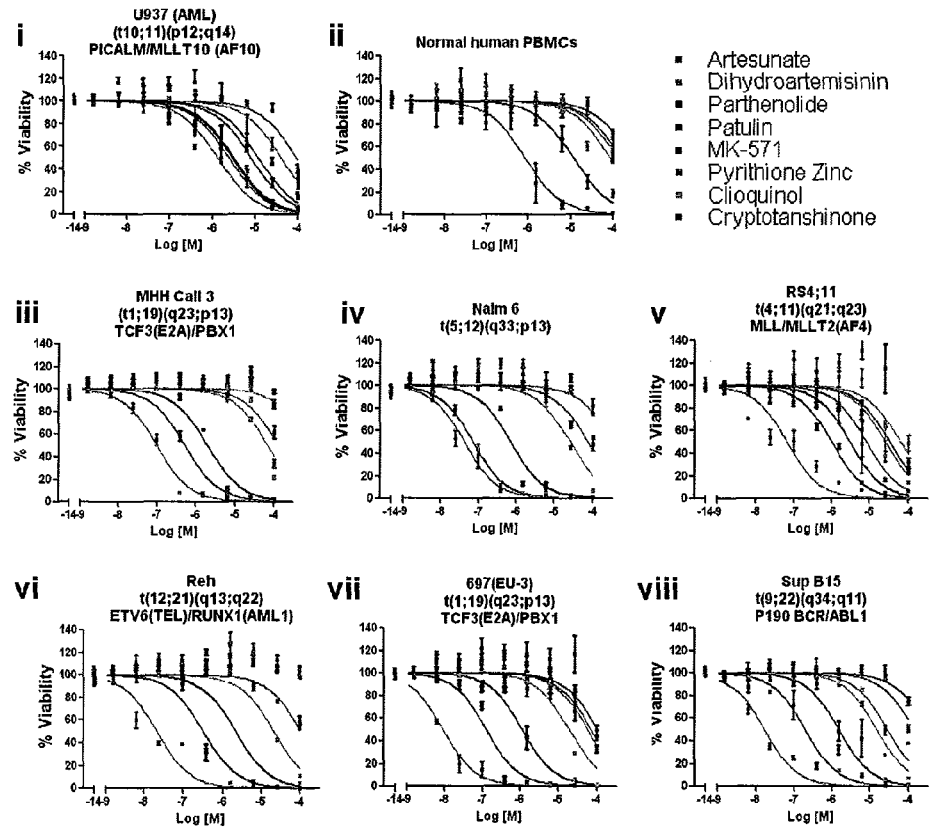
FIG. 6A. Effects of identified cAMP efflux inhibitors on cell viability of U937, normal human PBMCs, and the B-lineage ALL cell lines 697, Reh, MHH Call 3, RS4;11, Sup B15, and Nalm 6. Data were normalized such that 1% DMSO negative control was equal to 100% viability. Data for U937 and PBMCs were fit using variable slope log (agonist) vs response nonlinear regressions with the following constraints: top=100, bottom=0. Data for B-ALL cell lines were fit using variable slope sigmoidal dose response fits with the following constraints: top=100, bottom=0, hill slope=1. B) EC50 values determined from fits described in (A) for tested compounds with each cell type.

Because there was a possibility that the hit compounds may have additional debilitating effects on U937 cells, their influences on proliferation were investigated as well. To accomplish this, carboxyfluorescein diacetate succinimidyl ester (CFSE) was loaded into cells to bind to intracellular proteins and serve as a fluorescent marker for cellular generation. Lower remaining CFSE values indicate high proliferative capacity. Post-staining, cells were grown in the presence of compound, and samples were collected after 2, 3, and 4 day incubations. Samples were measured for remaining CFSE fluorescence by flow cytometry. Analysis revealed decreased cell fluorescence, indicating cell division. Some compounds (patulin, parthenolide, dihydroartemisinin) showed arrest of cell division within 48 hr, at concentrations of 3 μM, while control condition cells continued to proliferate (FIG. 5A).

cAMP Efflux Inhibitors Decreased Cell Viability and Showed Cancer Cell Specificity To validate increased intracellular cAMP as a target for inducing leukemic cell death, the hit compound effects on cell viability were measured with Cell TiterGlo®. The hit compounds were tested with U937 cells, and several showed more potency than the positive control MK-571 (FIG. 6A a, i). This assay was repeated with the top 7 compounds (ART, DHA, PTH, PLN, PZ, CQ, CTS) in 6 B-lineage ALL cell lines (see Table 1). These cell lines showed more sensitivity than the U937 cells to several of the selected compounds (FIG. 6Aa, iii-viii), but showed decreased sensitivity to the artemisinin derivatives, artesunate and dihydroartemisinin. The $EC_{50}$ values for the hit compounds with each cell line ranged from low nanomolar to ~200 μM (FIG. 6A b). It can be noted, however, that the compounds which consistently decreased viability the best were "ranked" the same across the 6 B-ALL lines: pyrithione zinc, patulin, parthenolide, clioquinol, cryptotanshinone.

These results led to the examination of potential selectivity of the hit compounds for decreasing viability in leukemic cells over healthy cells. Therefore, the same viability assay was repeated with healthy human peripheral blood mononuclear cells (PBMCs). Comparison of the compounds with all 8 cell types tested show PBMC responses at higher concentrations than the tested cell lines, indicating compound selectivity for the cancer cells (FIG. 6A a, ii). Calculated $EC_{50}$ values indicate that for most of the tested compounds, leukemic cells required concentrations an order of magnitude or lower than was necessary for the PBMCs to be efficacious (FIG. 6A b). This is expected, because normal PBMCs would not have an established system for cAMP efflux, and therefore would not be as sensitive to our identified efflux-inhibiting compounds. The exception was pyrithione zinc, which is a known biocidal compound that in fungi inhibits membrane transport and decreases cellular ATP[20], and in human skin cells, decreases ATP via poly(ADP-ribose) polymerase involvement as well as DNA damage and upregulation of heat shock proteins[21].

Leukemic Cell Lines have Different Abilities to Efflux cAMP

Figure 7A:
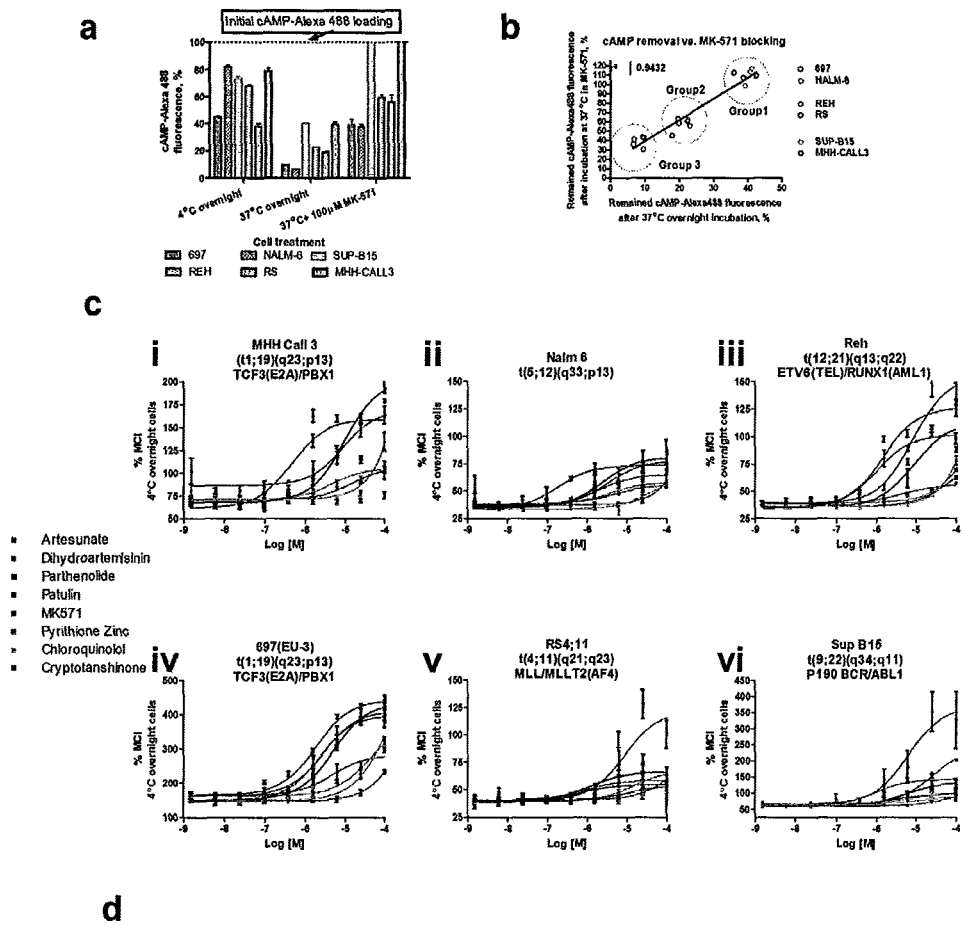
FIG. 7A. Retention of a fluorescent cAMP analog (F-cAMP) in hematopoietic cell lines after overnight incubation. A) F-cAMP leakage from B-lineage ALL cell lines after overnight incubation at 4° C., or 37° C., and in the presence of the HTS positive control/known cAMP efflux inhibitor, MK-571. Cell autofluorescence was subtracted, and the data were normalized to the cAMP-fluorescence value after initial staining. The graph depicts F-cAMP remaining within cells, and therefore, lower values correspond to higher probe removal activity. B) A negative correlation occurred between cAMP-Alexa 488 fluorescence which remained in cells incubated at 37° C. alone and in the presence of cAMP efflux inhibitor MK-571. Simply, cell lines which poorly removed cAMP were best inhibited by MK-571, and those cell lines which actively removed most of the incorporated cAMP were less inhibited by MK-571. Each cell line is represented by three independently processed samples for each treatment variant. C) F-cAMP retention after overnight incubation with HTS-identified compounds in dose response, as measured by flow cytometry for mean channel intensity (MCI). Percentage values are relative to fluorescence values of negative control cells incubated at 4° C. Note that there are different scales on the y-axes of the graphs. Lines indicate variable slope sigmoidal dose response fits with the following constraints: top=100, bottom=0, hill slope=1. D) Calculated EC50 concentrations of tested compounds with each cell line based on fits from (B). Data for the U937 cell line were collected at the time of HTS hit compound validation, and analyzed in the same manner.

To study differences in leukemic cell cAMP efflux, human cell lines representing different B-lineage ALL phenotypes (see Table 1 for information on genetic rearrangements for each line) were loaded with F-cAMP, and its efflux from the cells was studied. The cells were incubated overnight: 1) at 4° C. to estimate the passive F-cAMP probe "leakage", 2) at 37° C. to assess active removal of the probe, and 3) at 37° C. in the presence of the positive control 100 μM MK-571, a previously reported inhibitor of cAMP efflux to estimate the "pump-dependent" component of the process. Because cells loaded with F-cAMP were washed, the resulting concentration gradient could have caused a "passive leak" of the probe. All 6 cell lines appeared to efflux F-cAMP, although to different extents (FIG. 7A a). After incubation at 4° C., the cells lost 20-60% of their fluorescence from the initial F-cAMP loading. Incubation at 37° C. resulted in F-cAMP removal that ranged from ~60% for Sup B15 and MHH Call 3 cells, to ~90% for 697 and Nalm-6 cells, with no apparent correlation between 4° C. and 37° C. samples. For example, Nalm 6 cells showed the smallest "passive leak" with the highest active probe removal, and 697 cells exhibited a very significant "leakage", with high active probe removal comparable to Nalm 6 cells.

The cell lines also exhibited varied sensitivity to the effect of MK-571. The responses ranged from 0-60%, wherein "0" corresponds to the absence of F-cAMP efflux. For two cell lines, Sup B15 and MHH Call 3, the inhibitor completely blocked F-cAMP removal. For these cell lines, MK-571 blocked not only active probe removal at 37° C., but also efflux at 4° C., and therefore the fluorescent signal was equal to the initial cAMP probe loading value (FIG. 7A a). One possible explanation for this phenomenon could be that the inhibitor is interfering mechanically with the cAMP probe fluxes, for example, by blocking a "cAMP-specific channel". For 697 cells, MK-571 blocked F-cAMP removal close to the level of the "passive" 4° C. leakage, and for other cell lines the effect was different.

Because the results appeared so diverse, the fluorescence values after incubation with and without MK-571 were plotted against one another. We found a strong relationship between levels of the probe remaining in the cells at 37° C. alone and in the presence of the MK-571. Based on these data, the cell lines could be stratified into three groups which indicated correlations between ability to actively efflux cAMP and ability to block cAMP removal with MK-571 (FIG. 7A b). Group 1: Sup B15 and MHH Call 3 removed only ~60% of the probe without the inhibitor, and the F-cAMP efflux was blocked completely by MK-571. Group 2: Reh and RS4;11 cells removed 75-80% of the probe at 37° C., and ~30-40% in the presence of MK-571. Group 3: 697 and Nalm 6 cells removed more than 90% of the probe without MK-571, and 60-70% in the presence of MK-571 (FIG. 7A b). Essentially, those cell lines which poorly effluxed cAMP were best inhibited by MK-571, and those cell lines which actively removed most of the incorporated F-cAMP were less inhibited by MK-571.

These variations indicate the possibility that in different cell lines, the cAMP removal system which is sensitive to MK-571 represents a different fraction of the overall cAMP-pumping machinery. For Sup B15 and MHH Call 3, it represents a large portion of it, and therefore, the addition of MK-571 was sufficient to fully block probe efflux. For the other cell lines, additional MK-571-insensitive mechanisms participated in the removal of the probe, with the biggest fraction in Group 3. Thus, cell lines exhibited a large heterogeneity of the cellular machinery responsible for the removal of the fluorescent cAMP analog.

We then tested our identified hit compounds with the 6 cell lines in dose response under the same conditions as the HTS. FIG. 7A c shows the results of the assay, and it is apparent that the abilities of the compounds to inhibit cAMP efflux from the B-lineage cell lines varied.

This is underscored by the calculated $EC_{50}$ values determined from the assay (FIG. 7A d). However, these results were expected, considering that the B-lineage ALL cell lines had shown differing abilities to remove F-cAMP under normal conditions.

The Primary cAMP Transporter, ABCC4, is Differentially Expressed by Different Leukemic Cell Lines cAMP is typically released by cells via ATP-binding cassette (ABC) transporters (also known as multidrug resistance proteins (MDRs or MRPs)). According to the FDA Transporter Database, two ABC transporters have been reported to transfer cAMP out of a cell: ABCC4 (MRP4) and ABCC5 (MRP5)[22]. It should be noted that the affinity of ABCC4 for cAMP is ~100× greater than that of ABCC5 ($k_m$ values of 44.5 μM and 379 μM, respectively)[22,23]. Furthermore, while ABCC4 is expressed on the plasma membranes of CD34+ leukocytes, its expression decreases significantly upon cell differentiation[12]. Therefore, we hypothesized that the presence of MRP4 on leukemic cells would correlate with the ability to remove cAMP from the cells, as a mechanism for apoptotic escape.

ABCC4 phenotypes were determined for the B-lineage ALL cell lines (Table 1). Primary anti-human ABCC4 antibodies and isotype controls were bound to fixed cells in matched samples. The calculated number of MRP4-specific binding sites ranged from ~100 ABCC4 sites on MHH Call 3 cells to ~$10^4$ binding sites on RS4;11 cells (FIG. 8). It is possible that other transporters and/or mechanisms may play additional roles in leukemic cell removal of cAMP.

Figure 9:
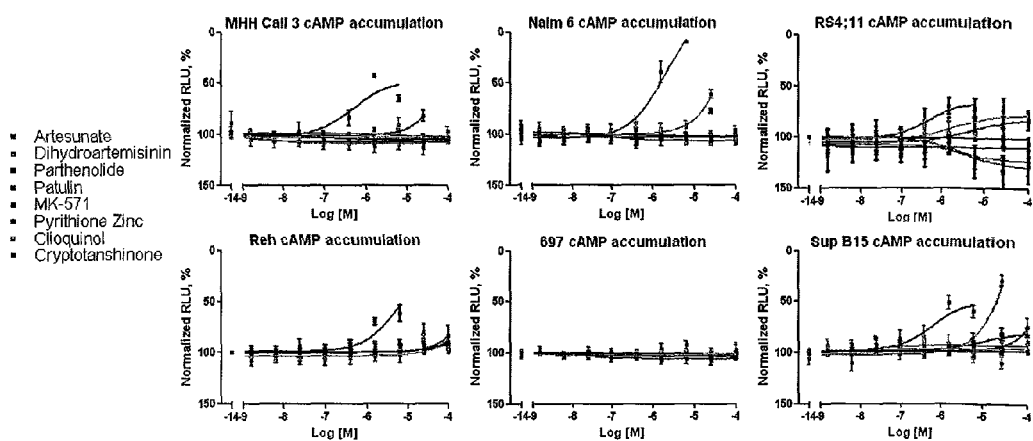
FIG. 9. Accumulation of intracellular cAMP after overnight treatment with identified cAMP efflux inhibiting compounds. A) Dose-dependent effects of hit compounds on intracellular cAMP concentrations in B-lineage ALL cell lines, as measured by the cAMP-Glo luminescence assay. Relative luminescence values (RLU) were normalized based on 1% DMSO control and 1.53 nM concentration wells for each cell line and treatment. Lines indicate variable slope sigmoidal dose response fits with constraint of hill slope=1. B The relationship between increased intracellular cAMP (i) and decreased cell viability (ii), as evidenced with the Reh cell line after overnight treatment with HTS-identified cAMP efflux inihibitors. iii) Comparison of compound EC50 values from both the viability and cAMP accumulation assays in Reh cells; $r^2$=0.9776.
Figure 9:
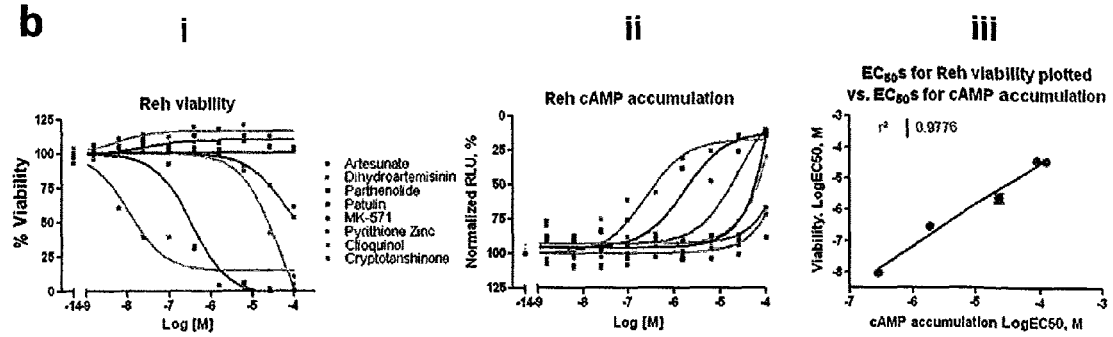

The cAMP Efflux Inhibitors Increase Intracellular cAMP Accumulation and Decrease ATP The results of the viability assay described above confirmed that the identified hit compounds decreased intracellular ATP. To reaffirm that the decreases in leukemic cell viability were due to the hit compound effects on increasing cAMP, the Promega cAMP-Glo™ assay was performed to measure cAMP accumulation within the cells. The 6 aforementioned B-lineage ALL cell lines (Table 1), U937 cells, and PBMCs were each incubated ~24 hours with the hit compounds, in dose response, and then luminescence was measured; in this assay, there is an inverse correlation between cAMP levels and luminescence. These luminescence values were then transformed into cAMP concentrations for each sample (FIG. 9a).

These results indicated a correlation between a decrease in cell viability and cAMP accumulation in some B-lineage ALL cell lines. The efficacy of the compounds also "ranked" in the same order as they did with the aforementioned assays, with pyrithione zinc, patulin, parthenolide, clioquinol, and cryptotanshinone resulting in the lowest $EC_{50}$ values. This relationship is further supported by the fact that when the $EC_{50}$ values for both cell viability and cAMP accumulation were plotted against one another, there were high coefficients of determination ($r^2$ values) and slopes approximately equal to 1 (FIG. 9b). Therefore, the identification of compounds based on their abilities to inhibit cAMP efflux as a means to selectively treat leukemic cells has been validated.

Discussion

Targeting cAMP Efflux

The HTS was an efficient, unbiased method to find compounds targeted to a cancer cell-specific functional, rather than physical, trait: cAMP efflux. The libraries screened contained off-patent, FDA-approved drugs, and can allow for faster turnaround time for potential translation to clinical therapeutic use of these compounds for patients with hematological malignancies. Our screen resulted in the identification of several active compounds which caused inhibition of cAMP efflux and resulted in increased intracellular cAMP. These compounds when used alone inhibited proliferation and viability, and induced apoptosis and cell cycle arrest in the U937 AML cell line. Moreover, these compounds decreased viability in B-lineage ALL cell lines, and the $EC_{50}$s of the most efficacious compounds ranked in the same order across cell lines: pyrithione zinc, patulin, parthenolide, clioquinol, cryptotanshinone. Importantly, when the hit compounds were tested on healthy human PBMCs, the measured $EC_{50}$ was much higher, indicating higher sensitivity of leukemic vs. normal cells. These findings support our hypothesis, and give validation to cAMP efflux as a cancer cell functional target.

Classically, cyclic nucleotide analogs or other cAMP-elevating agents such as all-trans retinoic acid have been used in treatment of hematological malignancies to slow cell growth and differentiate cancer cells. While modestly effective, these compounds had toxicity in non-cancerous tissues[24]. Our approach also seeks to use a cyclic nucleotide to inhibit blood cancers, however, this is achieved by increasing intracellular cAMP by preventing its efflux, which itself is a protective mechanism developed by malignant cells to evade typical apoptotic signals. Because increased cAMP production and efflux is not a typical trait of healthy cells, the cAMP efflux inhibitors that we have identified have some selectivity for cancerous cells.

Of the potentially active compounds identified in our screen for cAMP efflux inhibitors, the majority of them were sesquiterpene lactones: parthenolide is derived from the feverfew (*Tanacetum parthenium*) plant; artemisinin and dihydroartemisinin are from *Artemisia annua*. Artesunate and artemether are semi-synthetic artemisinin derivatives. Several identified compounds were previously reported to exhibit anticancer activity in a number of model systems (Table 2).

Parthenolide has been shown to prevent activation of the NF-κB pathway[27], and it is suspected that this occurs via inhibition of the IκB kinase[28-30]. Additionally, parthenolide inhibits the transcription factor AP-1 and ERK by preventing phosphorylation[29,31]. In studies with AML cells, parthenolide was shown to potentiate cell death when used in combination with histone deacetylase inhibitors (HDACIs)[32]. Parthenolide's ability to inhibit the NF-κB pathway has also been shown to more strongly inhibit cancer stem-like cells than non-stem cell counterparts[33,34]. Because cAMP also has these effects on the NF-κB pathway, this may reassert that parthenolide is indeed increasing intracellular cAMP. When in vitro B-lineage CLL cells were treated with parthenolide, in addition to inhibition of NF-κB, reactive oxygen species were generated, thus adding to its apoptotic effects[35]. These effects likewise occurred when parthenolide was administered to melanoma cells. Interestingly, parthenolide treatment also resulted in a reduction of ABCB5-positive cells and those malignant cells which remained had decreased proliferative ability[36].

Dihydroartemisinin is an antimalarial drug which has previously been shown to selectively induce apoptosis in a myriad of cancer cell lines[37-42] (see also Table 2). This cell death may occur by intrinsic[38,42-45] and/or[46-48] extrinsic[37,40,49] apoptotic pathways. Additionally, dihydroartemisinin can decrease cell proliferation[43,46,48,50,51], and cause cell cycle arrest at either $G_1$[43] or $G_2/M$[42,45,46,52]. One major mechanism by which dihydroartemisinin may achieve these effects is through its binding to iron[47], which results in generation of reactive oxygen species (ROS)[38,39,41,44,48-50] and downregulation of the transferrin receptor[50,52,53]. This drug also inhibits NFκB[43,46,54] and MAPK/ERK signaling[40,47,55]. Furthermore, dihydroartemisinin inhibits VEGF and decreases angiogenesis[51,52,56-59].

In lung adenocarcinoma, DHA causes ER stress and translocation of Bim to the ER, but induced apoptosis is not dependent on these factors[60].

DHA inhibits MEK/ERK pathway and causes downregulation of Mcl-1, but only apoptosis is caspase-dependent[55].

DHA shows selectivity for prostate cancer vs normal cells, inhibits PI3K/Akt and MAPK/ERK pathways, causes apoptosis via extrinsic (upregulated expression of death receptor 5) mechanisms[40].

DHA is selectively cytotoxic to glioma vs normal cells, by inhibiting HIF-1α (thereby decreasing survival factors like VEGF) and increasing ROS production due to interactions with iron[41].

DHA is selective for ovarian cancer cells in induction of $G_2$ cell cycle arrest and apoptosis by decreasing expression of anti-apoptotic proteins (Bcl-2 and Bcl-$x_L$) and increasing expression of pro-apoptotic proteins (Bax and Bad)[42].

In hepatocellular carcinoma DHA induces G2/M arrest via inhibition of cyclin B and CDC25C, depolarization of mitochondrial membranes, decrease in Mcl-1, increase in Noxa and Bak, apoptosis involved p53 and caspases 3 and 9 (intrinsic pathway)[45].

Artesunate is a phytoconstituent obtained from the Chinese medicinal herb *Artemisia annua*. It has a sesquiterpene lactone structure with an internal peroxide bridge, which provides a different structural prototype compared to classical antimalaria drugs such as e.g. chloroquine, quinine, proguanil or sulfadoxine. Semisynthetic derivatives of artemisinin; artesunate, artemether, and arteether; have been developed. After oral administration of artemisinin, deoxyartemisinin, deoxydihydroartemisinin, 9,10-dihydrodeoxyartemisinin and a metabolite named 'crystal 7' were identified in human urine. All four metabolites are inactive due to the lack of the endoperoxide bridge. Artesunate is hydrolyzed within minutes to its active metabolite, dihydroartemisinin, which is considered to be responsible for the antimalarial activity.

Patulin is a mycotoxin which is produced by *Aspergillus* or *Penicillium*, and is most often found in moldy fruit, particularly apples, and this molecule binds to and forms adducts with sulfhydryl groups[61].

In vivo (healthy male mice), induces apoptosis via DNA damage, lipid peroxidation, and a decrease in amount of glutathione (GSH)[62]. Showed selectivity for brain, liver, kidney over bladder.

Increases DNA damage, ERK1/2 phosphorylation (associated with extracellular signaling) and increases expression of early growth response gene-1 in MDCK (canine kidney), HEK293, and PBMCs[63]. Sustained ERK activation can cause cell differentiation.

It has been described that cAMP efflux via ABCC4 is dependent on intracellular glutathione (GSH), and that decreased GSH leads to decreased cellular export of cAMP[64]. Therefore, it makes sense that cell exposure to patulin, has been shown to decrease GSH in other studies[62] would be identified as a cAMP efflux inhibitor in our HTS.

CHO-K1 cell cytotoxicity was induced by ROS, which led to lipid peroxidation; also increased production of malondialdehyde[65].

Induces unfolded protein response signaling, including the PERK/eIF2α/CHOP apoptotic and IRE1/XBP1 adaptive arms of the response, and also caused activation of BH3-only genes and apoptosis[66].

In Caco-2 colon cancer cells, patulin disrupted tight junctions by downregulating ZO-1 (via increased phosphorylation→degradation) and claudin-4[67].

In human keratinocytes, patulin decreased autophagosome degradation, leading to increased p62 in a pro-survival role: ROS generation, UPR, ERK1/2 phosphorylation, and inhibition of BAD[68].

In colorectal cells, patulin caused cell cycle and growth arrest at $G_2/M$, and ROS generation caused by the compound was responsible for ATF3 expression and apoptosis[69].

In HEK293 and HL-60 cells, patulin caused lipid peroxidation and ROS generation. This ROS generation influenced ERK1/2 signaling, and vice versa[70].

Cryptotanshinone is a plant-derived (*Salvia miotiorrhiza*) compound which exhibited cAMP efflux inhibition and coincided with decreased blood cancer cell viability. While there is evidence that this compound may be selective for treatment-resistant malignant cells[71,72], it should be noted that in our experiments, the $EC_{50}$ for decreased PBMC viability with cryptotanshinone was only ~12 μM, which is a lower concentrations that were determined for some of the tested B-lineage ALL cell lines (Sup B15, Reh, Nalm 6, MHH Call 3). However, cryptotanshinone has been shown to induce cell cycle arrest, decrease proliferation, and induce apoptosis in a myriad of cancer types; the efficacy of these effects seem to vary based on metastatic capacity and type of cancer[73,74]. It is hypothesized that cryptotanshinone can prevent the expression of vital cell components such as cyclin D1[71,75,76] and Bcl-2[71,77]. It can also stimulate the extrinsic pathway of apoptosis by upregulating expression of TRAIL receptor 2[72], and activate caspase 3 and Bax[77]. Some of the antiproliferative effects of cryptotanshinone may be due to inhibition of mTOR signaling, resulting in decreased expression of cyclin D1 and eukaryotic initiation factor 4E, and decreased phosphorylation of retinoblastoma (Rb) protein phosphorylation[75]. In melanoma cells, cryptotanshinone caused increased expression of p53, Chk1, and Chk2[73]. Cryptotanshinone is also known to have antitumor effects by inhibition of the STAT3 pathway[76,78]. It is interesting to note that studies to determine the bioavailability of cryptotanshinone in the gut found that the drug may be a substrate of the P-glycoprotein (ABCB1) transporter[79].

Clioquinol is an antimicrobial drug that has recently been tested as a potential anticancer therapeutic. It is binds to divalent metal ions, and can serve as a chelator or ionophore. Consequently, there are multiple potential mechanisms of action in terms of clioquinol's anti-blood cancer effects. As a zinc chelator, clioquinol has been noted to fit into the binding pockets of histone deacetylases, thereby inhibiting their activities[80]. This has resulted in upregulation of tumor suppressor genes, such as p21, p27, p53, and additionally, in cessation of proliferation and apoptosis[80]. As a transition metal ionophore, clioquinol increases intracellular zinc concentrations and leads to apoptosis[81], and it is suspected that this may be due to down regulation of NF-κB signaling[81-83], and increasing lysosomal [zinc][82]. Further support for its ability to inhibit NF-κB may be inferred from the fact that cyclin D1, a downstream gene targeted by NF-κB, and major player in the regulation of the cell cycle, is decreased after exposure to the clioquinol[84]. Clioquinol is also able to bind with copper, and therefore can inhibit proteasome activity and induce apoptosis[85-87]; these effects may produce signals to activate macrophages to release TNF-α, further increasing cancer-cell specific activity[88]. Currently, clioquinol is being tested in a Phase I clinical trial for potential translation into a treatment for hematological malignancies[89].

8-quinolinol, a compound closely related to clioquinol has been shown to be especially effective in decreasing the proliferation of breast cancer stem cells over regular breast cancer tumor cells, and it is thought that its mechanism of action is through inhibition of NF-κB activation[90].

cAMP Regulation cAMP plays several significant regulatory roles within cells. Therefore, it is very plausible that cancer cells, especially those resistant to treatment, have developed adaptations to supersede conditions by which intracellular cAMP would result in differentiation or apoptosis. cAMP has been shown to impede tumor suppressor p53 from accumulating, thus cells have less response to DNA[91]. Also, cAMP can inhibit and promote NF-κB activity[92]. Constitutive activation of NF-κB is an important trait in leukemic stem cells[90,93]. NF-κB is pro-survival (hence often associated with cancer), inhibition is pro-apoptotic. cAMP inhibits p53, so prevents apoptosis[94]. It has been documented that increased intracellular cAMP inhibits the ability of NF-κB to facilitate transcription[95].

In some studies with cancer cell lines, increased cAMP has been shown to inhibit proliferation and increase c-KIT expression[96]. These effects seem paradoxical, as c-KIT is known to positively regulate cell growth. Elevated c-KIT had no effect on cell growth[96]. cAMP stimulation or inhibition of MAP kinase/ERK is cell type-specific[97]. In most tumor and hematological cells, cAMP inhibits ERK, and results in cell cycle arrest and ablation of proliferation[98,99].

GPCRs, Adenylyl Cyclase (AC), PDEs as Targets for cAMP Level Modulation

Targeting cancer and specifically hematological malignancies through a "pathway-dependent approach" that consists of different means of elevating cAMP is considered a valuable option for novel therapeutic development[100]. Starting with the increasing of AC activity using GPCR ligands, antagonists for $G_i$-coupled receptors or agonists for $G_s$-coupled receptors, direct AC activators, PDE inhibitors and drugs modifying cAMP downstream signaling, all represent various approaches to the stimulation of cAMP accumulation. It appears that every potential step of cAMP synthesis, degradation, and downstream signaling was taken into a consideration[100-102]. However, if efflux of cAMP from the cell is the major mechanism of decreasing the cAMP concentration, therapies based on other pathway steps will be obsolete[11,100].

Our data suggest that targeting cAMP efflux could be an efficient way to raise cAMP in certain types of cancer. The relative efficiency of this approach would directly depend on the expression and the activity of the target pumps that is anticipated to be cell- or patient-specific.

cAMP Efflux Mechanism

The two cAMP efflux proteins, ABCC4 and ABCC5[22], are unique among the ABC transporters, and lack much structural similarity to other multidrug resistance proteins and one another[64]. ABCC4 is non-vital for survival, as evidenced by normal phenotypes of MRP4−/− mice. However, this protein is especially important in nucleotide sensitivity of the bone marrow, thymus, spleen, and intestine[103]. In comparison to normal hematopoietic cells, blood cancer cells express more ABCC4[104]. However, xenografts of these cancer cell lines in the spleen and thymus are particularly sensitive to inhibition of ABCC4 substrate (mitoxantrone) efflux by MK-571[104]. The fact that ABC transporters are upregulated in stem-like cells may suggest that these cells require the removal of cAMP or other structurally-related compounds from the cytoplasm in order to remain in a pluripotent state. The other possibility is that the metabolic specificity of these cells requires active pumping of certain metabolites[105].

The results of our ABCC4-labeling assay did not determine any clear correlations between the cAMP efflux ability and ABCC4 expression in the cell lines. It is possible that other ABC transporters capable of cAMP efflux are present. ABCC5 or ABCC11 are good candidates for this role[23,106]. A difference in the pump activity is the other possible explanation. The increased concentrations of cAMP in urine of leukemia patients may be explained by efflux from ABCC4[107].

However, known substrates/inhibitors of ABCC4 (sulindac, diclofenac, topotecan) were also in the libraries used for the preliminary screen (sometimes in duplicate), yet did not come out as hits. This may mean that inhibition of the pumps may potentially be substrate- or condition-dependent. Future studies will need to focus more on these transporters to implicate their roles in cAMP efflux.

Additionally, cancer cells with stem cell-like characteristics potentially express higher levels of other ABC transporters, e.g. ABCG2, which represent an inherent "molecular determinant" of the "side-population" analysis that is commonly used to identify stem cells[13,108]. These cancer stem cells are associated with higher resistance to typical cancer therapeutics[109]. We anticipate that identification of drugs that could inhibit these transporters would allow for more selective targeting of resistant cancers and better patient outcomes. For example sildenafil, a PDE 5-specific inhibitor, decreases ABCG2- and ABCB1-mediated drug efflux[110]. This merits investigation into the effect of identified compounds on other ABC transporters.

TABLE 2

Most active identified cAMP-efflux inhibiting compounds

| Compound | Cancers(s) treated |
| --- | --- |
| Patulin | kidney[53], oral squamous cell carcinoma[55], glioblastoma[111], colon[67], colorectal[59], hematological[70] |
| Parthenolide | melanoma[27,35], cervical[29,30], hematological[32,34,35], breast[33], (cystic fibrosis[28,31]) |
| Artesunate | ovarian[37], cervical[39] |
| Dihydroartemisinin | ovarian[37,42], breast[50], liver[45,50], melanoma[38], pancreatic[43,49,54,57,112], lung[48,59,60], cervical[39], hematological[44,47,51,52,55,58], prostate[40], glioma[41], osteosarcoma[46] |

TABLE 2-continued

Most active identified cAMP-efflux inhibiting compounds

| Compound | Cancers(s) treated |
|---|---|
| Clioquinol | hematological[80,81,86,89], breast[84,85], HeLa[88], prostate[82,83,87] |
| Cryptotanshinone | hematological[71,75], prostate[74,75,78], breast[75,77], melanoma[72,73], lung[72], rhabodomyosarcoma[75] |

REFERENCES

1. Hanahan, D. & Weinberg, R. A. Hallmarks of cancer: the next generation. *Cell* 144, 646-74 (2011).
2. Dou, A. & Wang, X. Cyclic adenosine monophosphate signal pathway in targeted therapy of lymphoma. *Chin. Med. J. (Engl)*. 123, 95-99 (2010).
3. Francis, S. H., Blount, M. A. & Corbin, J. D. Mammalian Cyclic Nucleotide Phosphodiesterases□: Molecular Mechanisms and Physiological Functions. *Physiol. Rev.* 91, 651-690 (2011).
4. Cheepala, S. et al. Cyclic nucleotide compartmentalization: contributions of phosphodiesterases and ATP-binding cassette transporters. *Annu. Rev. Pharmacol. Toxicol.* 53, 231-53 (2013).
5. Zambon, A. C., Wilderman, A., Ho, A. & Insel, P. a. Increased expression of the pro-apoptotic protein BIM, a mechanism for cAMP/protein kinase A (PKA)-induced apoptosis of immature T cells. *J. Biol. Chem.* 286, 33260-7 (2011).
6. Coffino, P., Bourne, H. R. & Tomkins, G. M. Mechanism of Lymphoma Cell Death Induced by Cyclic AMP. *Am. J. Pathol.* 81, 199-204 (1975).
7. Follin-Arbelet, V. et al. Cyclic AMP induces apoptosis in multiple myeloma cells and inhibits tumor development in a mouse myeloma model. *BMC Cancer* 11, 301 (2011).
8. Carlson, C. C., Chinery, R., Burnham, L. L. & Dransfield, D. T. 8-Cl-adenosine-induced inhibition of colorectal cancer growth in vitro and in vivo. *Neoplasia* 2, 441-8 (2000).
9. Insel, P., Zhang, L., Murray, F., Yokouchi, H. & Zambon, A. Cyclic AMP is both a pro-apoptotic and anti-apoptotic second messenger. *Acta Physiol. (Oxf)*. 204, 277-87 (2012).
10. Shayo, C. et al. The time-course of cyclic AMP signaling is critical for leukemia U-937 cell differentiation. *Biochem. Biophys. Res. Commun.* 314, 798-804 (2004).
11. Copsel, S. et al. Multidrug resistance protein 4 (MRP4/ABCC4) regulates cAMP cellular levels and controls human leukemia cell proliferation and differentiation. *J. Biol. Chem,* 286, 6979-88 (2011).
12. Oevermann, L. et al. Hematopoietic stem cell differentiation affects expression and function of MRP4 (ABCC4), a transport protein for signaling molecules and drugs. *Int. J. Cancer* 124, 2303-11 (2009).
13. Zhou, S. et al. The ABC transporter Bcrp1/ABCG2 is expressed in a wide variety of stem cells and is a molecular determinant of the side-population phenotype. *Nat. Med.* 7, 1028-34 (2001).
14. Conley, J. M. et al. Development of a high-throughput screening paradigm for the discovery of small-molecule modulators of adenylyl cyclase: identification of an adenylyl cyclase 2 inhibitor. *J. Pharmacol. Exp. Ther.* 347, 276-87 (2013).
15. Lerner, A. & Epstein, P. M. Cyclic nucleotide phosphodiesterases as targets for treatment of haematological malignancies. *Biochem. J.* 393, 21-41 (2006).
16. Meyers, J. a, Su, D. W. & Lerner, A. Chronic lymphocytic leukemia and B and T cells differ in their response to cyclic nucleotide phosphodiesterase inhibitors. *J. Immunol.* 182, 5400-11 (2009).
17. Scavennec, J., Carcassonne, Y., Gastaut, J. & Scavennec, J. Relationship between the Levels of Cyclic cytidine 3'□: 5' Cyclic Adenosine 3'□5'-Monophosphate in Urines and Leukocytes and the Type of Human Leukemias. *Cancer Res.* 41, 3222-3227 (1981).
18. Peracchi, M. et al. Plasma and urine cyclic nucleotide levels in patients with acute and chronic leukemia. *Blood* 61, 429-34 (1983).
19. Okada, C. Y. & Rechsteiner, M. Introduction of macromolecules into cultured mammalian cells by osmotic lysis of pinocytic vesicles. *Cell* 29, 33-41 (1982).
20. Chandler, C. J. & Segel, I. H. Mechanism of the Antimicrobial Action of Pyrithione: Effects on Membrane Transport, ATP Levels, and Protein Synthesis. *Antimicrob. Agents Chemother.* 14, 60-68 (1978).
21. Lamore, S. D., Cabello, C. M. & Wondrak, G. T. The topical antimicrobial zinc pyrithione is a heat shock response inducer that causes DNA damage and PARP-dependent energy crisis in human skin cells. *Cell Stress Chaperones* 15, 309-22 (2010).
22. Morrissey, K. M. et al. The UCSF-FDA TransPortal: a public drug transporter database. *Clin. Pharmacol. Ther.* 92, 545-6 (2012).
23. Borst, P., de Wolf, C. & van de Wetering, K. Multidrug resistance-associated proteins 3, 4, and 5. *Pflugers Arch.* 453, 661-73 (2007).
24. Guillemin, M.-C. et al. In Vivo Activation of cAMP Signaling Induces Growth Arrest and Differentiation in Acute Promyelocytic Leukemia. *J. Exp. Med.* 196, 1373-1380 (2002).
25. Kumar, S., Kostin, S., Flacke, J.-P., Reusch, H. P. & Ladilov, Y. Soluble adenylyl cyclase controls mitochondria-dependent apoptosis in coronary endothelial cells. *J. Biol. Chem.* 284, 14760-8 (2009).
26. Xie, J. et al. cAMP inhibits mammalian target of rapamycin complex-1 and -2 (mTORC1 and 2) by promoting complex dissociation and inhibiting mTOR kinase activity. *Cell. Signal.* 23, 1927-35 (2011).
27. Czyz, M., Lesiak-Mieczkowska, K., Koprowska, K., Szulawska-Mroczek, a & Wozniak, M. Cell context-dependent activities of parthenolide in primary and metastatic melanoma cells. *Br. J. Pharmacol.* 160, 1144-57 (2010).
28. Saadane, A., Masters, S., DiDonato, J., Li, J. & Berger, M. Parthenolide inhibits IkappaB kinase, NF-kappaB activation, and inflammatory response in cystic fibrosis cells and mice. *Am. J. Respir. Cell Mol. Biol.* 36, 728-36 (2007).
29. Hehner, S. P., Hofmann, T. G., Dröge, W. & Schmitz, M. L. The antiinflammatory sesquiterpene lactone parthenolide inhibits NF-kappa B by targeting the I kappa B kinase complex. *J. Immunol.* 163, 5617-23 (1999).
30. Kwok, B. H. B., Koh, B., Ndubuisi, M. I., Elofsson, M. & Crews, C. M. The anti-inflammatory natural product parthenolide from the medicinal herb Feverfew directly binds to and inhibits IkB kinase. *Chem. Biol.* 8, 759-766 (2001).
31. Saadane, A., Eastman, J., Berger, M. & Bonfield, T. L. Parthenolide inhibits ERK and AP-1 which are dysregulated and contribute to excessive IL-8 expression and secretion in cystic fibrosis cells. *J. Inflamm. (Lond)*. 8, 26 (2011).
32. Dai, Y. et al. The NF (Nuclear factor)-κB inhibitor parthenolide interacts with histone deacetylase inhibitors to 33. Zhou, J. et al. NF-kappaB pathway inhibitors preferentially inhibit breast cancer stem-like cells. *Breast Cancer Res. Treat.* 111, 419-27 (2008).
34. Guzman, M. L. et al. An orally bioavailable parthenolide analog selectively eradicates acute myelogenous leukemia stem and progenitor cells. *Blood* 110, 4427-35 (2007).
35. Steele, A. J. et al. The sesquiterpene lactone parthenolide induces selective apoptosis of B-chronic lymphocytic leukemia cells in vitro. *Leukemia* 20, 1073-9 (2006).
36. Czyz, M., Koprowska, K. & Sztiller-Sikorska, M. Parthenolide reduces the frequency of ABCB5-positive cells and clonogenic capacity of melanoma cells from anchorage independent melanospheres. *Cancer Biol. Ther.* 14, 135-45 (2013).
37. Chen, T., Li, M., Zhang, R. & Wang, H. Dihydroartemisinin induces apoptosis and sensitizes human ovarian cancer cells to carboplatin therapy. *J. Cell. Mol. Med.* 13, 1358-70 (2009).
38. Cabello, C. M. et al. The redox antimalarial dihydroartemisinin targets human metastatic melanoma cells but not primary melanocytes with induction of NOXA-dependent apoptosis. *Invest. New Drugs* 30, 1289-301 (2012).
39. Disbrow, G. L. et al. Dihydroartemisinin is cytotoxic to papillomavirus-expressing epithelial cells in vitro and in vivo. *Cancer Res.* 65, 10854-61 (2005).
40. He, Q. et al. Dihydroartemisinin upregulates death receptor 5 expression and cooperates with TRAIL to induce apoptosis in human prostate cancer cells. *Cancer Biol. Ther.* 9, 819-24 (2010).
41. Huang, X.-J., Ma, Z.-Q., Zhang, W.-P., Lu, Y.-B. & Wei, E.-Q. Dihydroartemisinin exerts cytotoxic effects and inhibits hypoxia inducible factor-1 alpha activation in C6 glioma cells. *J. Pharm. Pharmacol.* 59, 849-56 (2007).
42. Jiao, Y. et al. Dihydroartemisinin is an inhibitor of ovarian cancer cell growth. *Acta Pharmacol. Sin.* 28, 1045-56 (2007).
43. Chen, H. et al. Growth inhibitory effects of dihydroartemisinin on pancreatic cancer cells: involvement of cell cycle arrest and inactivation of nuclear factor-kappaB. *J. Cancer Res. Clin. Oncol.* 136, 897-903 (2010).
44. Handrick, R. et al. Dihydroartemisinin induces apoptosis by a Bak-dependent intrinsic pathway. *Mol. Cancer Ther.* 9, 2497-510 (2010).
45. Zhang, C. Z., Zhang, H., Yun, J., Chen, G. G. & Lai, P. B. S. Dihydroartemisinin exhibits antitumor activity toward hepatocellular carcinoma in vitro and in vivo. *Biochem. Pharmacol.* 83, 1278-89 (2012).
46. Ji, Y. et al. Anti-tumor effects of dihydroartemisinin on human osteosarcoma. *Mol. Cell. Biochem.* 351, 99-108 (2011).
47. Lu, J. et al. Dihydroartemisinin induces apoptosis in HL-60 leukemia cells dependent of iron and p38 mitogen-activated protein kinase activation but independent of reactive oxygen species. *Cancer Biol. Ther.* 7, 1017-1023 (2008).
48. Lu, Y.-Y., Chen, T.-S., Wang, X.-P. & Li, L. Single-cell analysis of dihydroartemisinin-induced apoptosis through reactive oxygen species-mediated caspase-8 activation and mitochondrial pathway in ASTC-a-1 cells using fluorescence imaging techniques. *J. Biomed. Opt.* 15, 046028 (2010).
49. Kong, R. et al. Dihydroartemisinin enhances Apo2L/TRAIL-mediated apoptosis in pancreatic cancer cells via ROS-mediated up-regulation of death receptor 5. *PLoS One* 7, e37222 (2012).
50. Ba, Q. et al. Dihydroartemisinin exerts its anticancer activity through depleting cellular iron via transferrin receptor-1. *PLoS One* 7, e42703 (2012).
51. Lee, J., Zhou, H.-J. & Wu, X.-H. Dihydroartemisinin downregulates vascular endothelial growth factor expression and induces apoptosis in chronic myeloid leukemia K562 cells. *Cancer Chemother. Pharmacol.* 57, 213-20 (2006).
52. Wang, Z., Hu, W., Zhang, J.-L., Wu, X.-H. & Zhou, H.-J. Dihydroartemisinin induces autophagy and inhibits the growth of iron-loaded human myeloid leukemia K562 cells via ROS toxicity. *FEBS Open Bio* 2, 103-12 (2012).
53. Zhou, H.-J., Wang, Z. & Li, A. Dihydroartemisinin induces apoptosis in human leukemia cells HL60 via downregulation of transferrin receptor expression. *Anticancer. Drugs* 19, 247-55 (2008).
54. Wang, S.-J. et al. Dihydroartemisinin inactivates NF-kappaB and potentiates the anti-tumor effect of gemcitabine on pancreatic cancer both in vitro and in vivo. *Cancer Lett,* 293, 99-108 (2010).
55. Gao, N. et al. Interruption of the MEK/ERK signaling cascade promotes dihydroartemisinin-induced apoptosis in vitro and in vivo. *Apoptosis* 16, 511-23 (2011).
56. Chen, H.-H., Zhou, H.-J., Wang, W.-Q. & Wu, G.-D. Antimalarial dihydroartemisinin also inhibits angiogenesis. *Cancer Chemother. Pharmacol.* 53, 423-32 (2004).
57. Wang, S.-J. et al. Dihydroartemisinin inhibits angiogenesis in pancreatic cancer by targeting the NF-κB pathway. *Cancer Chemother. Pharmacol.* 68, 1421-30 (2011).
58. Wu, X.-H., Zhou, H.-J. & Lee, J. Dihydroartemisinin inhibits angiogenesis induced by multiple myeloma RPMI8226 cells under hypoxic conditions via downregulation of vascular endothelial growth factor expression and suppression of vascular endothelial growth factor secretion. *Anticancer. Drugs* 17, 839-48 (2006).
59. Zhou, H.-J., Zhang, J.-L., Li, A., Wang, Z. & Lou, X.-E. Dihydroartemisinin improves the efficiency of chemotherapeutics in lung carcinomas in vivo and inhibits murine Lewis lung carcinoma cell line growth in vitro. *Cancer Chemother. Pharmacol.* 66, 21-9 (2010).
60. Chen, M., Chen, T., Lu, Y., Liu, C. & Qu, J. Dihydroarteminsin-induced apoptosis is not dependent on the translocation of Bim to the endoplasmic reticulum in human lung adenocarcinoma cells. *Pathol. Oncol. Res.* 18, 809-16 (2012).
61. Puel, O., Galtier, P. & Oswald, I. P. Biosynthesis and toxicological effects of patulin. *Toxins (Basel).* 2, 613-31 (2010).
62. De Melo, F. T. et al. DNA damage in organs of mice treated acutely with patulin, a known mycotoxin. *Food Chem. Toxicol.* 50, 3548-55 (2012).
63. Wu, T.-S. et al. Activation of ERK mitogen-activated protein kinase in human cells by the mycotoxin patulin. *Toxicol. Appl. Pharmacol.* 207, 103-11 (2005).
64. Lai, L. & Tan, T. M. C. Role of glutathione in the multidrug resistance protein 4 (MRP4/ABCC4)-mediated efflux of cAMP and resistance to purine analogues. *Biochem. J.* 361, 497-503 (2002).
65. Ferrer, E., Juan-Garcia, a, Font, G. & Ruiz, M. J. Reactive oxygen species induced by beauvericin, patulin and zearalenone in CHO-K1 cells. *Toxicol. In Vitro* 23, 1504-9 (2009).

66. Fribley, A. M. et al. Complementary cell-based high-throughput screens identify novel modulators of the unfolded protein response. *J. Biomol. Screen.* 16, 825-35 (2011).
67. Kawauchiya, T. et al. Correlation between the destruction of tight junction by patulin treatment and increase of phosphorylation of ZO-1 in Caco-2 human colon cancer cells. *Toxicol. Lett.* 205, 196-202 (2011).
68. Guo, X. et al. Patulin induces pro-survival functions via autophagy inhibition and p62 accumulation. *Cell Death Dis.* 4, e822 (2013).
69. Kwon, O. et al. Patulin induces colorectal cancer cells apoptosis through EGR-1 dependent ATF3 up-regulation. *Cell. Signal.* 24, 943-50 (2012).
70. Liu, B.-H., Wu, T.-S., Yu, F.-Y. & Su, C.-C. Induction of oxidative stress response by the mycotoxin patulin in mammalian cells. *Toxicol. Sci.* 95, 340-7 (2007).
71. Ge, Y. et al. Cryptotanshinone induces cell cycle arrest and apoptosis of multidrug resistant human chronic myeloid leukemia cells by inhibiting the activity of eukaryotic initiation factor 4E. *Mol. Cell. Biochem.* 368, 17-25 (2012).
72. Tse, A. K.-W. et al. The herbal compound cryptotanshinone restores sensitivity in cancer cells that are resistant to the tumor necrosis factor-related apoptosis-inducing ligand. *J. Biol. Chem.* 288, 29923-33 (2013).
73. Chen, L. et al. Cryptotanshinone has diverse effects on cell cycle events in melanoma cell lines with different metastatic capacity. *Cancer Chemother. Pharmacol.* 68, 17-27 (2011).
74. Wu, C.-Y., Hsieh, C.-Y., Huang, K.-E., Chang, C. & Kang, H.-Y. Cryptotanshinone down-regulates androgen receptor signaling by modulating lysine-specific demethylase 1 function. *Int. J. Cancer* 131, 1423-34 (2012).
75. Chen, W. et al. Cryptotanshinone inhibits cancer cell proliferation by suppressing Mammalian target of rapamycin-mediated cyclin D1 expression and Rb phosphorylation. *Cancer Prev. Res.* 3, 1015-25 (2010).
76. Jung, J. H. et al. Apoptosis Induced by Tanshinone IIA and Cryptotanshinone Is Mediated by Distinct JAK/STAT3/5 and SHP1/2 Signaling in Chronic Myeloid Leukemia K562 Cells. *Evid. Based. Complement. Alternat. Med.* 2013, 805639 (2013).
77. Nizamutdinova, I. T. et al. Tanshinone I effectively induces apoptosis in estrogen receptor-positive (MCF-7) and estrogen receptor-negative (MDA-MB-231) breast cancer cells. *Int. J. Oncol.* 33, 485-491 (2008).
78. Shin, D.-S. et al. Cryptotanshinone inhibits constitutive signal transducer and activator of transcription 3 function through blocking the dimerization in DU145 prostate cancer cells. *Cancer Res.* 69, 193-202 (2009).
79. Dai, H. et al. Coexisted components of *Salvia miltiorrhiza* enhance intestinal absorption of cryptotanshinone via inhibition of the intestinal P-gp. *Phytomedicine* 19, 1256-62 (2012).
80. Cao, B. et al. The antiparasitic clioquinol induces apoptosis in leukemia and myeloma cells by inhibiting histone deacetylase activity. J. Biol. Chem. 288, 34181-9 (2013).
81. Ding, W., Liu, B., Vaught, J. L., Yamauchi, H. & Lind, S. E. Anticancer Activity of the Antibiotic Clioquinol Anticancer Activity of the Antibiotic Clioquinol. *Cancer Res.* 65, 3389-3395 (2005).
82. Yu, H., Zhou, Y., Lind, S. E. & Ding, W.-Q. Clioquinol targets zinc to lysosomes in human cancer cells. *Biochem. J.* 417, 133-9 (2009).
83. Yu, H., Lou, J. R. & Ding, W.-Q. Clioquinol independently targets NF-kappaB and lysosome pathways in human cancer cells. *Anticancer Res.* 30, 2087-92 (2010).
84. Zheng, J., Benbrook, D. M., Yu, H. & Ding, W.-Q. Clioquinol suppresses cyclin D1 gene expression through transcriptional and post-transcriptional mechanisms. *Anticancer Res.* 31, 2739-47 (2011).
85. Daniel, K. G. et al. Clioquinol and pyrrolidine dithiocarbamate complex with copper to form proteasome inhibitors and apoptosis inducers in human breast cancer cells. *Breast Cancer Res.* 7, R897-908 (2005).
86. Mao, X. et al. Clioquinol inhibits the proteasome and displays preclinical activity in leukemia and myeloma. *Leukemia* 23, 585-90 (2009).
87. Chen, D. et al. Clioquinol, a therapeutic agent for Alzheimer's disease, has proteasome-inhibitory, androgen receptor-suppressing, apoptosis-inducing, and antitumor activities in human prostate cancer cells and xenografts. *Cancer Res.* 67, 1636-44 (2007).
88. Du, T., Filiz, G., Caragounis, A., Crouch, P. J. & White, A. R. Clioquinol Promotes Cancer Cell Toxicity through Tumor Necrosis Factor alpha Release from Macrophages. *J. Pharmacol. Exp. Ther.* 324, 360-367 (2008).
89. Schimmer, A. D. et al. A phase I study of the metal ionophore clioquinol in patients with advanced hematologic malignancies. *Clin. Lymphoma. Myeloma Leuk.* 12, 330-6 (2012).
90. Zhou, J. et al. Cancer stem/progenitor cell active compound 8-quinolinol in combination with paclitaxel achieves an improved cure of breast cancer in the mouse model. *Breast Cancer Res. Treat.* 115, 269-77 (2009).
91. Naderi, E. H., Jochemsen, A. G., Blomhoff, H. K. & Naderi, S. Activation of cAMP Signaling Interferes with Stress-Induced p53 Accumulation in ALL-Derived Cells by Promoting the Interaction. 13, 653-663 (2011).
92. Gerlo, S. et al. Cyclic AMP: a selective modulator of NF-κB action. *Cell. Mol. Life Sci.* 68, 3823-41 (2011).
93. Guzman, M. L. et al. Nuclear factor-kappaB is constitutively activated in primitive human acute myelogenous leukemia cells. *Blood* 98, 2301-2307 (2001).
94. Kloster, M. M., Naderi, E. H., Carlsen, H., Blomhoff, H. K. & Naderi, S. Hyperactivation of NF-κB via the MEK signaling is indispensable for the inhibitory effect of cAMP on DNA damage-induced cell death. *Mol. Cancer* 10, 45 (2011).
95. Olivier, V., Parry, G. C. N., Cobb, R. R., de Prost, D. & Mackman, N. Elevated Cyclic AMP Inhibits NF-kappa B-mediated Transcription in Human Monocytic Cells and Endothelial Cells. *J. Biol. Chem.* 271, 20828-20835 (1996).
96. Shaw, T. J., Keszthelyi, E. J., Tonary, A. M., Cada, M. & Vanderhyden, B. C. Cyclic AMP in ovarian cancer cells both inhibits proliferation and increases c-KIT expression. *Exp. Cell Res.* 273, 95-106 (2002).
97. Stork, P. J. S. & Schmitt, J. M. Crosstalk between cAMP and MAP kinase signaling in the regulation of cell proliferation. *Trends Cell Biol.* 12, 258-66 (2002).
98. Alers, S., Löffler, A. S., Wesselborg, S. & Stork, B. Role of AMPK-mTOR-Ulk1/2 in the regulation of autophagy: cross talk, shortcuts, and feedbacks. *Mol. Cell. Biol.* 32, 2.-11 (2012).
99. Rocha, A. S. et al. Cyclic AMP Inhibits the Proliferation of Thyroid Carcinoma Cell Lines through Regulation of CDK4 Phosphorylation. *Mol. Biol. Cell* 19, 4814-4825 (2008).
100. Murray, F. & Insel, P. a. Targeting cAMP in chronic lymphocytic leukemia: a pathway-dependent approach for the treatment of leukemia and lymphoma. *Expert Opin. Ther. Targets* 17, 937-49 (2013).

101. Naviglio, S. et al. Protein kinase A as a biological target in cancer therapy. *Expert Opin. Ther. Targets* 13, 83-92 (2009).
102. Savai, R. et al. Targeting cancer with phosphodiesterase inhibitors. *Expert Opin. Investig. Drugs* 19, 117-31 (2010).
103. Belinsky, M. G. et al. Multidrug resistance protein 4 protects bone marrow, thymus, spleen, and intestine from nucleotide analogue-induced damage. *Cancer Res.* 67, 262-8 (2007).
104. Takeuchi, K., Shibata, M., Kashiyama, E. & Umehara, K. Expression levels of multidrug resistance-associated protein 4 (MRP4) in human leukemia and lymphoma cell lines, and the inhibitory effects of the MRP-specific inhibitor MK-571 on methotrexate distribution in rats. *Exp. Ther. Med.* 4, 524-532 (2012).
105. Baumann, K. Stem cells: A metabolic switch. *Nat. Rev. Mol. Cell Biol.* 14, 64-5 (2013).
106. Chen, Z.-S. & Tiwari, A. K. Multidrug resistance proteins (MRPs/ABCCs) in cancer chemotherapy and genetic diseases. *FEBS J.* 278, 3226-45 (2011).
107. Van Aubel, R. a M. H., Smeets, P. H. E., Peters, J. G. P., Bindels, R. J. M. & Russel, F. G. M. The MRP4/ABCC4 gene encodes a novel apical organic anion transporter in human kidney proximal tubules: putative efflux pump for urinary cAMP and cGMP. *J. Am. Soc. Nephrol.* 13, 595-603 (2002).
108. Ding, X., Wu, J. & Jiang, C. ABCG2: a potential marker of stem cells and novel target in stem cell and cancer therapy. *Life Sci.* 86, 631-7 (2010).
109. Felipe Rico, J., Hassane, D. C. & Guzman, M. L. Acute myelogenous leukemia stem cells: from Bench to Bedside. *Cancer Lett.* 338, 4-9 (2013).
110. Shi, Z., Tiwari, A. K., Patel, A. S., Fu, L.-W. & Chen, Z.-S. Roles of sildenafil in enhancing drug sensitivity in cancer. *Cancer Res.* 71, 3735-8 (2011).
111. Hothi, P. et al. High-Throughput Chemical Screens Identify Disulfiram as an Inhibitor of Human Glioblastoma Stem Cells. *Oncotarget* 3, 1124-1136 (2012).
112. Chen, H., Sun, B., Pan, S., Jiang, H. & Sun, X. Dihydroartemisinin inhibits growth of pancreatic cancer cells in vitro and in vivo. *Anticancer. Drugs* 20, 131-40 (2009).
113. Andersson, A. et al. Gene expression profiling of leukemic cell lines reveals conserved molecular signatures among subtypes with specific genetic aberrations. *Leukemia* 19, 1042-50 (2005).

REFERENCE LIST FOR BACKGROUND OF THE INVENTION AND EXAMPLES 1 AND 2

1. Akiyama T, Dass C R and Choong P F. Bim-targeted cancer therapy: a link between drug action and underlying molecular changes. *Mol Cancer Ther* 8: 3173-3180, 2009.
2. Amin H M, Yang Y, Shen Y, Estey E H, Giles F J, Pierce S A, Kantarjian H M, O'Brien S M, Jilani I and Albitar M. Having a higher blast percentage in circulation than bone marrow: clinical implications in myelodysplastic syndrome and acute lymphoid and myeloid leukemias. *Leukemia* 19: 1567-1572, 2005.
3. Chigaev A, Smagley Y and Sklar L A. Nitric oxide/cGMP pathway signaling actively down-regulates alpha4beta1-integrin affinity: an unexpected mechanism for inducing cell de-adhesion. *BMC Immunol* 12: 28, 2011.
4. Chigaev A, Waller A, Amit O and Sklar L A. Galphas-coupled receptor signaling actively down-regulates alpha4beta1-integrin affinity: a possible mechanism for cell de-adhesion. *BMC Immunol* 9: 26, 2008.
5. Gausdal G, Wergeland A, Skavland J, Nguyen E, Pendino F, Rouhee N, McCormack E, Herfindal L, Kleppe R, Havemann U, Schwede F, Bruserud O, Gjertsen B T, Lanotte M, Segal-Bendirdjian E and Doskeland S O. Cyclic AMP can promote APL progression and protect myeloid leukemia cells against anthracycline-induced apoptosis. *Cell Death Dis* 4: e516, 2013.
6. Insel P A, Zhang L, Murray F, Yokouchi H and Zambon A C. Cyclic AMP is both a pro-apoptotic and anti-apoptotic second messenger. *Acta Physiol (Oxf)* 204: 277-287, 2012.
7. Jiao B, Ren Z H, Liu P, Chen L J, Shi J Y, Dong Y, Ablain J, Shi L, Gao L, Hu J P, Ren R B, De The H, Chen Z and Chen S J. 8-CPT-cAMP/all-trans retinoic acid targets t(11;17) acute promyelocytic leukemia through enhanced cell differentiation and PLZF/RARalpha degradation. *Proc Natl Acad Sci USA* 110: 3495-3500, 2013.
8. Kato J Y, Matsuoka M, Polyak K, Massague J and Sherr C J. Cyclic AMP-induced G1 phase arrest mediated by an inhibitor (p27Kip1) of cyclin-dependent kinase 4 activation. *Cell* 79: 487-496, 1994.
9. Lapidot T, Dar A and Kollet O. How do stem cells find their way home? *Blood* 106: 1901-1910, 2005.
10. Lerner A and Epstein P M. Cyclic nucleotide phosphodiesterases as targets for treatment of haematological malignancies. *Biochem J* 393: 21-41, 2006.
11. Moon E Y and Lerner A. PDE4 inhibitors activate a mitochondrial apoptotic pathway in chronic lymphocytic leukemia cells that is regulated by protein phosphatase 2A. *Blood* 101: 4122-4130, 2003.
12. Naviglio S, Caraglia M, Abbruzzese A, Chiosi E, Di Gesto D, Marra M, Romano M, Sorrentino A, Sorvillo L, Spina A and Illiano G. Protein kinase A as a biological target in cancer therapy. *Expert Opin Ther Targets* 13: 83-92, 2009.
13. Nguyen E, Gausdal G, Varennes J, Pendino F, Lanotte M, Doskeland S and Segal-Bendirdjian E. Activation of Both Protein Kinase A (PKA) Type I and PKA Type II Isozymes Is Required for Retinoid-Induced Maturation of Acute Promyelocytic Leukemia Cells. *Mol Pharmacol* 2013.
14. Oevermann L, Scheitz J, Starke K, Kock K, Kiefer T, Dolken G, Niessen J, Greinacher A, Siegmund W, Zygmunt M, Kroemer H K, Jedlitschky G and Ritter C A. Hematopoietic stem cell differentiation affects expression and function of MRP4 (ABCC4), a transport protein for signaling molecules and drugs. *Int J Cancer* 124: 2303-2311, 2009.
15. Okada C Y and Rechsteiner M. Introduction of macromolecules into cultured mammalian cells by osmotic lysis of pinocytic vesicles. *Cell* 29: 33-41, 1982.
16. Peracchi M, Maiolo A T, Lombardi L, Catena F B and Polli E E. Patterns of cyclic nucleotides in normal and leukaemic human leucocytes. *Br J Cancer* 41: 360-371, 1980.
17. Peracchi M, Toschi V, Bamonti-Catena F, Lombardi L, Bareggi B, Cortelezzi A, Colombi M, Maiolo A T and Polli E E. Plasma cyclic nucleotide levels in acute leukemia patients. *Blood* 69: 1613-1616, 1987.
18. Petrie K, Zelent A and Waxman S. Differentiation therapy of acute myeloid leukemia: past, present and future. *Curr Opin Hematol* 16: 84-91, 2009.
19. Quenech'Du N, Ruchaud S, Khelef N, Guiso N and Lanotte M. A sustained increase in the endogenous level of cAMP reduces the retinoid concentration required for APL cell maturation to near physiological levels. *Leukemia* 12: 1829-1833, 1998.
20. Ruchaud S, Duprez E, Gendron M C, Houge G, Genieser H G, Jastorff B, Doskeland S O and Lanotte M. Two distinctly regulated events, priming and triggering, during retinoid-induced maturation and resistance of NB4 promyelocytic leukemia cell line. *Proc Natl Acad Sci USA* 91: 8428-8432, 1994.
21. Savai R, Pullamsetti S S, Banat G A, Weissmann N, Ghofrani H A, Grimminger F and Schermuly R T. Targeting cancer with phosphodiesterase inhibitors. *Expert Opin Investig Drugs* 19: 117-131, 2010.
22. Scavennec J, Carcassonne Y, Gastaut J A, Blanc A and Cailla H L. Relationship between the levels of cyclic cytidine 3':5'-monophosphate, cyclic guanosine 3':5'-monophosphate, and cyclic adenosine 3':5'-monophosphate in urines and leukocytes and the type of human leukemias. *Cancer Res* 41: 3222-3227, 1981.
23. Shayo C, Davio C, Brodsky A, Mladovan A G, Legnazzi B L, Rivera E and Baldi A. Histamine modulates the expression of c-fos through cyclic AMP production via the H2 receptor in the human promonocytic cell line U937. *Mol Pharmacol* 51: 983-990, 1997.
24. Shayo C, Legnazzi B L, Monczor F, Fernandez N, Riveiro M E, Baldi A and Davio C. The time-course of cyclic AMP signaling is critical for leukemia U-937 cell differentiation. *Biochem Biophys Res Commun* 314: 798-804, 2004.
25. Shen Z X, Shi Z Z, Fang J, Gu B W, Li J M, Zhu Y M, Shi J Y, Zheng P Z, Yan H, Liu Y F, Chen Y, Shen Y, Wu W, Tang W, Waxman S, De The H, Wang Z Y, Chen S J and Chen Z. All-trans retinoic acid/As2O3 combination yields a high quality remission and survival in newly diagnosed acute promyelocytic leukemia. *Proc Natl Acad Sci USA* 101: 5328-5335, 2004.
26. Wang Z Y and Chen Z. Acute promyelocytic leukemia: from highly fatal to highly curable. *Blood* 111: 2505-2515, 2008.
27. Zambon A C, Wilderman A, Ho A and Insel P A. Increased expression of the pro-apoptotic protein BIM, a mechanism for cAMP/protein kinase A (PKA)-induced apoptosis of immature T cells. *J Biol Chem* 286: 33260-33267, 2011.
28. Zhao Q, Tao J, Zhu Q, Jia P M, Dou A X, Li X, Cheng F, Waxman S, Chen G Q, Chen S J, Lanotte M, Chen Z and Tong J H. Rapid induction of cAMP/PKA pathway during retinoic acid-induced acute promyelocytic leukemia cell differentiation. *Leukemia* 18: 285-292, 2004.
29. Zhu Q, Zhang J W, Zhu H Q, Shen Y L, Flexor M, Jia P M, Yu Y, Cai X, Waxman S, Lanotte M, Chen S J, Chen Z and Tong J H. Synergic effects of arsenic trioxide and cAMP during acute promyelocytic leukemia cell maturation subtends a novel signaling cross-talk. *Blood* 99: 1014-1022, 2002.

What is claimed is:

1. A method of determining whether a composition of unknown activity against a cancer is effective in the treatment of said cancer, the method comprising contacting a test eukaryotic cancer cell sample with the composition, measuring cellular cAMP efflux, and comparing measured cellular cAMP efflux of said test cancer cell sample with levels of cAMP efflux in a control eukaryotic cancer cell sample, wherein reduced expression levels of cAMP efflux of said test sample when compared to control expression levels indicates that the composition is effective in the treatment of said cancer.

2. The method according to claim 1 wherein said cancer is a carcinoma, a leukemia, a malignant lymphoma, a malignant melanoma, a myeloproliferative disease, a sarcoma, a tumor of the central nervous system or a germ-line tumor.

3. The method according to claim 2 wherein said carcinoma is a carcinoma of the bladder, bowel, breast, cervix, colon, esophagus, head, kidney, liver, lung, neck, ovary, pancreas, prostate, or stomach, said lymphoma is Burkitt's lymphoma or Non-Hodgkin's lymphoma, said sarcoma is Ewing's sarcoma, hemangiosarcoma, Kaposi's sarcoma, liposarcoma, myosarcomas, peripheral neuroepithelioma or synovial sarcoma, and said tumor of the central nervous system is a glioma, astrocytoma, oligodendroglioma, ependymoma, gliobastoma, neuroblastoma, ganglioneuroma, ganglioglioma, medulloblastoma, pineal cell tumor, meningioma, meningeal sarcoma, neurofibroma or Schwannoma.

4. The method according to claim 1 wherein said cancer is bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancel, melanoma, carcinosarcoma, Hodgkin's disease, Wilms' tumor or teratocarcinoma.

5. A method of determining the effectiveness of cancer therapy in a patient in need with an anti-cancer composition, the method comprising administering said composition to said patient and measuring cAMP in the urine of said patient at least once during a course of therapy, wherein a decrease in measured c-AMP over the course of therapy evidences effectiveness of the therapy in the treatment of said patient's cancer.

6. The method according to claim 5 wherein said urine cAMP from said patient is compared to a standard.

7. The method according to claim 6 wherein said standard is determined by measuring cAMP in the urine of the patient before commencing therapy.

8. The method according to claim 6 wherein said standard is determined by measuring cAMP in the urine of a population of cancer patients before commencing.

9. The method according to claim 6 wherein said composition comprises an anticancer agent selected from the group consisting of microtubule-stabilizing agents, microtubule-disruptor agents, alkylating agents, epidophyllotoxins, antineoplastic enzymes, topoisomerase inhibitors, inhibitors of cell cycle progression, platinum coordination complexes and mixtures thereof.

10. The method according to claim 6 wherein said composition comprises an anticancer agent selected from the group consisting of a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody or a mixture thereof.

11. The method according to claim 6 wherein said composition comprises an anticancer agent selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-disodium salt heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258, 3-[5-(methylsulfonylpiperadinemethyl)-indolylj-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, Clioquinol and mixtures thereof.

12. A method of determining whether a composition of unknown activity against a cancer is effective in the treatment of said cancer, the method comprising contacting a test eukaryotic cancer cell sample with the composition, measuring cellular F-cAMP efflux in said test cancer cell sample, and comparing measured cellular F-cAMP efflux in said test cancer cell sample with levels of F-cAMP efflux in a control eukaryotic cancer cell sample, wherein reduced expression levels of F-cAMP efflux when compared to control or standard expression levels indicates that the composition is effective in the treatment of said cancer.

13. The method according to claim 12 wherein said cancer is a carcinoma, a leukemia, a malignant lymphoma, a malignant melanoma, a myeloproliferative disease, a sarcoma, a tumor of the central nervous system or a germ-line tumor.

14. The method according to claim 13 wherein said carcinoma is a carcinoma of the bladder, bowel, breast, cervix, colon, esophagus, head, kidney, liver, lung, neck, ovary, pancreas, prostate, or stomach, said lymphoma is Burkitt's lymphoma or Non-Hodgkin's lymphoma, said sarcoma is Ewing's sarcoma, hemangiosarcoma, Kaposi's sarcoma, liposarcoma, myosarcomas, peripheral neuroepithelioma or synovial sarcoma, and said tumor of the central nervous system is a glioma, astrocytoma, oligodendroglioma, ependymoma, gliobastoma, neuroblastoma, ganglioneuroma, ganglioglioma, medulloblastoma, pineal cell tumor, meningioma, meningeal sarcoma, neurofibroma or Schwannoma.

15. The method according to claim 12 wherein said cancer is bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma, carcinosarcoma, Hodgkin's disease, Wilms' tumor or teratocarcinoma.

16. A method of determining whether a patient with cancer is a candidate for cancer therapy comprising obtaining cancer tissue, including cancer cells from said patient, exposing said tissue and/or cells to said cancer therapy and measuring F-cAMP efflux from said cells wherein a reduction of F-cAMP efflux from said cells compared to a standard evidences that the patient will respond to said proposed treatment.

17. The method according to claim 16 wherein said cancer therapy comprises at least one anticancer agent selected from the group consisting of microtubule-stabilizing agents, microtubule-disruptor agents, alkylating agents, epidophyllotoxins, antineoplastic enzymes, topoisomerase inhibitors, inhibitors of cell cycle progression and platinum coordination complexes.

18. The method according to claim 16 wherein said cancer therapy comprises at least one anticancer agent is selected from the group consisting of a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor and a VEGF trap antibody.

19. The method according to claim 16 wherein said cancer therapy comprises at least one anticancer agent selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilfene, oblimersen, ticilimumab, ipilimumab, gossypol, Bio 111, 131-I-TM-601, ALT-110, BIO 140, CC 8490, cilengitide, gimatecan, IL13-PE38QQR, NO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl) ethyl]benzoyl]-disodium salt heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258, 3-[5-(methylsulfonylpiperadinemethyl)-indolylj-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and Clioquinol.

20. The method according to claim 16 wherein said standard is a measurement of F-cAMP taken from said cancer cells before being exposed to said therapy.

21. The method according to claim 17 wherein said standard is a measurement of F-cAMP taken from said cancer cells before being exposed to said therapy.

22. The method according to claim 18 wherein said standard is a measurement of F-cAMP taken from said cancer cells before being exposed to said therapy.

23. The method according to claim 19 wherein said standard is a measurement of F-cAMP taken from said cancer cells before being exposed to said therapy.

24. The method according to claim 16 wherein said standard is a measurement of F-cAMP taken from said patient or a population of cancer patients prior to therapy.

25. The method according to claim 16 wherein said cancer is a carcinoma, a leukemia, a malignant lymphoma, a malignant melanoma, a myeloproliferative disease, a sarcoma, a tumor of the central nervous system or a germ-line tumor.

26. The method according to claim 25 wherein said carcinoma is a carcinoma of the bladder, bowel, breast, cervix, colon, esophagus, head, kidney, liver, lung, neck, ovary, pancreas, prostate, or stomach, said lymphoma is Burkitt's lymphoma or Non-Hodgkin's lymphoma, said sarcoma is Ewing's sarcoma, hemangiosarcoma, Kaposi's sarcoma, liposarcoma, myosarcomas, peripheral neuroepithelioma or synovial sarcoma and said tumor of the central nervous system is a glioma, astrocytoma, oligodendroglioma, ependymoma, gliobastoma, neuroblastoma, ganglioneuroma, ganglioglioma, medulloblastoma, pineal cell tumor, meningioma, meningeal sarcoma, neurofibroma or Schwannoma.

27. The method according to claim 16 wherein said cancer is bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma, carcinosarcoma, Hodgkin's disease, Wilms' tumor or teratocarcinoma.

\* \* \* \* \*